United States Patent
Nagase et al.

(10) Patent No.: US 10,751,421 B2
(45) Date of Patent: Aug. 25, 2020

(54) ALKYLATING AGENT FOR ALKYLATING TARGET WITH DRIVER ONCOGENE MUTATION

(71) Applicant: Chiba Prefecture, Chiba-shi, Chiba (JP)

(72) Inventors: Hiroki Nagase, Chiba (JP); Hiroshi Sugiyama, Kyoto (JP); Toshikazu Bando, Kyoto (JP); Atsushi Takatori, Chiba (JP)

(73) Assignee: CHIBA PREFECTURE, Chiba-Shi (JP)

( * ) Notice: Subject to any disclaimer, the term of this patent is extended or adjusted under 35 U.S.C. 154(b) by 0 days.

(21) Appl. No.: 16/377,867

(22) Filed: Apr. 8, 2019

(65) Prior Publication Data

US 2019/0290773 A1 Sep. 26, 2019

Related U.S. Application Data

(62) Division of application No. 15/027,877, filed as application No. PCT/JP2014/077766 on Oct. 14, 2014, now Pat. No. 10,350,300.

(30) Foreign Application Priority Data

Oct. 11, 2013 (JP) ................. 2013-214044

(51) Int. Cl.
C07D 403/14 (2006.01)
A61K 47/64 (2017.01)
C08G 73/06 (2006.01)

(52) U.S. Cl.
CPC ............ *A61K 47/64* (2017.08); *C07D 403/14* (2013.01); *C08G 73/0611* (2013.01); *C08G 73/0616* (2013.01)

(58) Field of Classification Search
CPC .................................................. C07D 403/14
See application file for complete search history.

(56) References Cited

U.S. PATENT DOCUMENTS

2007/0191260 A1 8/2007 Sugiyama et al.
2011/0160399 A1 6/2011 Nagase et al.

FOREIGN PATENT DOCUMENTS

| EP | 2311494 A1 | 4/2011 |
|---|---|---|
| WO | WO 2005/087762 A1 | 9/2005 |
| WO | WO 2010/001933 A1 | 1/2010 |
| WO | WO 2013/151638 A1 | 10/2013 |

OTHER PUBLICATIONS

Bando et al., "Pyrrole-Imidazole Polyamide no Koritsuteki na Alkyl-ka ga Motarasu Seibutsu Kassei," Abstracts of Annual Meeting of Pharmaceutical Society of Japan, vol. 124, No. 2, 2004, p. 54.
Bando et al., "The Chemical Biology That Controls DNA Function and Structure," Journal of Synthetic Organic Chemistry, Japan, vol. 63, No. 10, 2005, pp. 1016-1027, with English abstract.
Bando et al., "The Possibility of Sequence-specific DNA Alkylation toward Therapeutic Drugs," Pharmaceutical Regulatory Science (Study of Medical Supplies), vol. 36, No. 1, 2005, pp. 1-12.
English translation of Bando et al., "Pyrrole-Imidazole Polyamide no Koritsuteki na Alkyl-ka ga Motarasu Seibutsu Kassei," Abstracts of Annual Meeting of Pharmaceutical Society of Japan, vol. 124, No. 2, 2004, p. 54.
English translation of Bando et al., "The Chemical Biology That Controls DNA Function and Structure," Journal of Synthetic Organic Chemistry, Japan, vol. 63, No. 10, 2005, pp. 1016-1027.
English translation of Bando et al., "The Possibility of Sequence-specific DNA Alkylation toward Therapeutic Drugs," Pharmaceutical Regulatory Science (Study of Medical Supplies), vol. 36, No. 1, 2005, pp. 1-12.
English translation of Iida et al., "Recognition of DNA Sequences by Pyrrole-Imidazole Polyamide: Rational Drug Design in the Post-Genome Era," Journal of Synthetic Organic Chemistry, Japan, vol. 58, No. 10, 2000, pp. 975-987.
English translation of Kashiwazaki et al., "Evaluation of biological activities of alkylating PI polyamide conjugates," CSJ: The Chemical Society of Japan Koen Yokoshu, vol. 91, No. 3, 2011, p. 735 (4 pages total).
English translation of Kawakami et al., "Regulation of Gene Expression by Sequence-Specific Alkylating Polyamide," CSJ: The Chemical Society of Japan Koen Yokoshu, vol. 81, No. 2, 2002, p. 945.
English translation of Kumamoto et al., "Application for the Gene Regulation of Bcr-abl Expression by Sequence-Specific DNA Alkylation," CSJ: The Chemical Society of Japan Koen Yokoshu, vol. 90, No. 3, p. 750.
English translation of Minoshima et al., "Sequence-specific DNA alkylation and biochemical application," CSJ: The Chemical Society of Japan Koen Yokoshu, vol. 89, No. 2, 2009, p. 1391.
English translation of Narita et al., "Sequence Specific DNA Alkylation and in vivo Gene Silencing by Alkylating Pyrrole-Imidazole Polyamides," CSJ: The Chemical Society of Japan Koen Yokoshu, vol. 84, No. 2, 2004, p. 1063.
English translation of Oyoshi et al., "Regulation of Gene Expression by Sequence-Specific Alkylating Polyamide," CSJ: The Chemical Society of Japan Koen Yokoshu, vol. 83, No. 2, 2003, p. 1127.
English translation of Saito et al., "Hito Genome Saizensen 21 Seiki wa Idenshi no Jidai II Bu Post Genome no Yukue Post Genome no Seibutsu Yuki Kagaku Idenshi o Target to suru Drug Design," Chemistry Separate Volume, vol. 2001, 2001, pp. 89-110.

(Continued)

*Primary Examiner* — Shawquia Jackson
(74) *Attorney, Agent, or Firm* — Birch, Stewart, Kolasch & Birch, LLP

(57) ABSTRACT

The present invention provides a novel alkylating agent specifically binding to the genetic mutation site of a driver oncogene. There are provided are a complex formed by binding an alkylating agent to a pyrrole imidazole polyamide specifically binding to the genetic mutation site of a driver oncogene, a driver oncogene mutation-specific alkylating agent comprising the aforementioned complex, and a pharmaceutical composition comprising the aforementioned complex.

17 Claims, 34 Drawing Sheets

Specification includes a Sequence Listing.

(56) References Cited

OTHER PUBLICATIONS

English translation of Sasaki et al., "New Design of Alkylating Pyrrole-Imidazole Polyamides Possessing DNA Sequence Specificities," Abstracts, Symposium on Biofunctional Chemistry, vol. 22, 2007, pp. 92-93.

English translation of Sasaki et al., "New Molecular Design of Hairpin Imidazole-Pyrrole Polyamides Possessing DNA Alkylation Activity," CSJ: The Chemical Society of Japan Koen Yokoshu, vol. 84, No. 2, 2004, p. 1049.

English translation of Sugiyama, "Aiming at development of tailor-made anticancer drug, Tan'itsu Bunshi Genshi Level no Hanno Seigyo," Dai 6 Kai Symposium 2 Ki Team (Heisei 8 Nendo Saitaku) Kenkyu Seika Hokoku Koen Yoshishu Heisei 14 Nen, 2002, pp. 67-70.

English translation of Sugiyama, "Control of Specific Gene Expression by Pyrrole-Imidazole Polyamides," Saishin Igaku, vol. 56, No. 3, Mar. 2001, pp. 376-383.

English translation of Sugiyama, "DDS Targeting DNA Specific Sequence," Saishin Igaku, vol. 61, No. 6, Jun. 2006, pp. 1067-1074.

English translation of Sugiyama, "Rational Design of Tailor-made Antitumor Agent," Kagaku Kogyo, vol. 55, No. 4, Apr. 2004, pp. 291-296.

English translation of Sugiyama, "Sequence-Specific DNA Alkylatlon toward Tailor-Made Antitumor Agent," Polymer Preprints, Japan, vol. 52, No. 13, 2003, pp. 3708-3709.

Extended European Search Report issued in European Application No. 14851833.5, dated May 11, 2017.

Iida et al., "Recognition of DNA Sequences by Pyrrole-Imidazole Polyamide: Rational Drug Design in the Post-Genome Era," Journal of Synthetic Organic Chemistry, Japan, vol. 58, No. 10, 2000, pp. 975-987, with English abstract.

International Search Report (Form PCT/ISA/210) issued in International Application No. PCT/JP2014/077766, dated Nov. 11, 2014, together with an English translation.

Kashiwazaki et al., "Evaluation of biological activities of alkylating PI polyamide conjugates," CSJ: The Chemical Society of Japan Koen Yokoshu, vol. 91, No. 3, 2011, p. 735 (4 pages total), with English abstract.

Kawakami et al., "Regulation of Gene Expression by Sequence-Specific Alkylating Polyamide," CSJ: The Chemical Society of Japan Koen Yokoshu, vol. 81, No. 2, 2002, p. 945.

Kumamoto et al., "Application for the Gene Regulation of Bcr-abl Expression by Sequence-Specific DNA Alkylation," CSJ: The Chemical Society of Japan Koen Yokoshu, vol. 90, No. 3, p. 750, with English abstract.

Minoshima et al., "Sequence-specific DNA alkylation and biochemical application," CSJ: The Chemical Society of Japan Koen Yokoshu, vol. 89, No. 2, 2009, p. 1391, with English abstract.

Narita et al., "Sequence Specific DNA Alkylation and in vivo Gene Silencing by Alkylating Pyrrole-Imidazole Polyamides," CSJ: The Chemical Society of Japan Koen Yokoshu, vol. 84, No. 2, 2004, p. 1063.

Oyoshi et al., "Regulation of Gene Expression by Sequence-Specific Alkylating Polyamide," CSJ: The Chemical Society of Japan Koen Yokoshu, vol. 83, No. 2, 2003, p. 1127.

Saito et al., "Hito Genome Saizensen 21 Seiki wa Idenshi no Jidai II Bu Post Genome no Yukue Post Genome no Seibutsu Yuki Kagaku Idenshi o Target to suru Drug Design," Chemistry Separate Volume, vol. 2001, 2001, pp. 89-110.

Sasaki et al., "New Design of Alkylating Pyrrole-Imidazole Polyamides Possessing DNA Sequence Specificities," Abstracts, Symposium on Biofunctional Chemistry, vol. 22, 2007, pp. 92-93, with English abstract.

Sasaki et al., "New Molecular Design of Hairpin Imidazole-Pyrrole Polyamides Possessing DNA Alkylation Activity," CSJ: The Chemical Society of Japan Koen Yokoshu, vol. 84, No. 2, 2004, p. 1049.

Sugiyama, "Aiming at development of tailor-made anticancer drug, Tan'itsu Bunshi Genshi Level no Hanno Seigyo," Dai 6 Kai Symposium 2 Ki Team (Heisei 8 Nendo Saitaku) Kenkyu Seika Hokoku Koen Yoshishu Heisei 14 Nen, 2002, pp. 67-70.

Sugiyama, "Control of Specific Gene Expression by Pyrrole-Imidazole Polyamides," Saishin Igaku, vol. 56, No. 3, Mar. 2001, pp. 376-383.

Sugiyama, "DDS Targeting DNA Specific Sequence," Saishin Igaku, vol. 61, No. 6, Jun. 2006, pp. 1067-1074.

Sugiyama, "Rational Design of Tailor-made Antitumor Agent," Kagaku Kogyo, vol. 55, No. 4, Apr. 2004, pp. 291-296.

Sugiyama, "Sequence-Specific DNA Alkylatlon toward Tailor-Made Antitumor Agent," Polymer Preprints, Japan, vol. 52, No. 13, 2003, pp. 3708-3709.

F1174L (3522C > A)

3511 ATC AGC AAA TTC AAC CAC CAG 3531
1171  I   S   K   F   N   H   Q  1177

5'- ATC AGC AAA TTA AAC CAC CAG -3'

3'- TAG TCG TTT AAT TTG GTG GTC-5'
                  └─── 10 bp ───┘

ALK-FL-1

SEQUENCE LISTING

```
<160> NUMBER OF SEQ ID NOS: 13

<210> SEQ ID NO 1
<211> LENGTH: 31
<212> TYPE: DNA
<213> ORGANISM: Artificial
<220> FEATURE:
<223> OTHER INFORMATION: Synthetic DNA

<400> SEQUENCE: 1
gcctacgcca tcagcgctgt tggcgtaggc a                                        31

<210> SEQ ID NO 2
<211> LENGTH: 31
<212> TYPE: DNA
<213> ORGANISM: Artificial
<220> FEATURE:
<223> OTHER INFORMATION: Synthetic DNA

<400> SEQUENCE: 2
acggatgcgg tagtcgcgac aaccgcatcc g                                        31

<210> SEQ ID NO 3
<211> LENGTH: 19
<212> TYPE: DNA
<213> ORGANISM: Artificial
<220> FEATURE:
<223> OTHER INFORMATION: Synthetic DNA

<400> SEQUENCE: 3
taatacgact cactatagg                                                      19

<210> SEQ ID NO 4
<211> LENGTH: 24
<212> TYPE: DNA
<213> ORGANISM: Artificial
<220> FEATURE:
<223> OTHER INFORMATION: Synthetic DNA

<400> SEQUENCE: 4
catacgattt aggtgacact atag                                                24

<210> SEQ ID NO 5
<211> LENGTH: 18
```

```
<212> TYPE: DNA
<213> ORGANISM: Artificial
<220> FEATURE:
<223> OTHER INFORMATION: Synthetic DNA

<400> SEQUENCE: 5
atttaggtga cactatag                                                 18

<210> SEQ ID NO 6
<211> LENGTH: 20
<212> TYPE: DNA
<213> ORGANISM: Artificial
<220> FEATURE:
<223> OTHER INFORMATION: Synthetic DNA

<400> SEQUENCE: 6
taatacgact cactataggg                                               20

<210> SEQ ID NO 7
<211> LENGTH: 18
<212> TYPE: DNA
<213> ORGANISM: Artificial
<220> FEATURE:
<223> OTHER INFORMATION: Synthetic DNA

<400> SEQUENCE: 7
ggagagaggc ctgctgaa                                                 18

<210> SEQ ID NO 8
<211> LENGTH: 20
<212> TYPE: DNA
<213> ORGANISM: Artificial
<220> FEATURE:
<223> OTHER INFORMATION: Synthetic DNA

<400> SEQUENCE: 8
tgacctgctg tgtcgagaat                                               20

<210> SEQ ID NO 9
<211> LENGTH: 20
<212> TYPE: DNA
<213> ORGANISM: Artificial
<220> FEATURE:
<223> OTHER INFORMATION: Synthetic DNA

<400> SEQUENCE: 9
gaggatgagg tggaacgtgt                                               20

<210> SEQ ID NO 10
<211> LENGTH: 20
<212> TYPE: DNA
<213> ORGANISM: Artificial
<220> FEATURE:
<223> OTHER INFORMATION: Synthetic DNA

<400> SEQUENCE: 10
tcttcagtcg ctccaggtct                                               20

<210> SEQ ID NO 11
<211> LENGTH: 18
<212> TYPE: DNA
<213> ORGANISM: Artificial
<220> FEATURE:
<223> OTHER INFORMATION: Synthetic DNA

<400> SEQUENCE: 11
```

```
ggagagaggc ctgctgaa                                              18

<210> SEQ ID NO 12
<211> LENGTH: 19
<212> TYPE: DNA
<213> ORGANISM: Artificial
<220> FEATURE:
<223> OTHER INFORMATION: Synthetic DNA

<400> SEQUENCE: 12
aaagaaagcc ctccccagt                                             19

<210> SEQ ID NO 13
<211> LENGTH: 24
<212> TYPE: DNA
<213> ORGANISM: Artificial
<220> FEATURE:
<223> OTHER INFORMATION: Synthetic DNA

<400> SEQUENCE: 13
cgccagggtt ttcccagtca cgac                                       24
```

ALKYLATING AGENT FOR ALKYLATING TARGET WITH DRIVER ONCOGENE MUTATION

CROSS REFERENCE TO RELATED APPLICATIONS

This application is a Divisional of copending application Ser. No. 15/027,877 filed on Jul. 12, 2016, which is the U.S. National Phase of PCT/JP2014/077766, filed Oct. 14, 2014, and which claims priority under 35 U.S.C. § 119(a) to Application No. 2013-214044 filed in Japan, on Oct. 11, 2013, the entire contents of all of which are expressly incorporated by reference into the present application.

TECHNICAL FIELD

The present invention relates to a novel alkylating agent that alkylates the genetic mutation site of a driver(s) oncogene as a target.

BACKGROUND ART

At present, molecular targeted therapy has been widely developed, targeting driver oncogenes (essential proto-oncogenes). The driver oncogene is a proto-oncogene having a genetic mutation that is considered to cause a mutation (e.g., point mutation, small deletion, insertion or translocation, amplification, etc.) specific to cancer cells and to become a main cause of cancer development. Accordingly, a technique of developing a drug that targets such a driver oncogene and suppresses the function thereof has been demonstrated to be a method extremely effective for the development of a specific remedy for cancer patients. Examples of such a specific remedy include: Iressa exhibiting drastic effectiveness for lung cancer patients with mutated EGFR; Trastuzumab effective for patients with breast cancer derived from high expression of HER2; and Imatinib that is an activity inhibitor for the fusion protein BCR-ABL.

The genetic mutations of such driver oncogenes are divided into two types; namely, (1) changes in gene sequences (point mutation, chromosomal translocation, deletion and/or insertion) (or such deletion or translocation mutation includes a mutation, in which SNP (single nucleotide polymorphism) becomes monoallelic or homoallelic in tumor cells, although it becomes heteroallelic in normal cells); and (2) changes in gene copy numbers (i.e., increases in gene expressions). As driver oncogenes having the above mutation (1), RAS, KRAS, HRAS, NRAS, BCR-ABL, EGFR, c-KIT, BRAF, PI3K, ALK, PIK3CA, FLT3, MET, BCL2, EML4-ALK, APC, BRCA1/2, TP53, MSH2, MLH1, MSH6, PMS2, RB1, PTEN, VHL, P16, MEN1, RET, CDH1, STK11, and PTCH have been known. As driver oncogenes having the above mutation (2), Her2/neu, EGFR, MYC, MYCN, MET, etc. have been known. Other driver oncogenes have been registered in cancer gene mutation database (COSMIC [Catalogue of somatic mutations in cancer], etc.).

To date, the development of drugs that specifically target the mutated sites of driver oncogene products has been frequently carried out. However, such a drug may also suppress the function of a normal gene product needed by normal cells, and a drug of interest has not yet been developed under the current circumstances.

It has been reported that pyrrole-imidazole polyamide (PIP) is an artificial small molecule developed using the antibiotic distamycin as a motif, and that PIP sequence-specifically binds to a minor group of double-stranded DNA. There have been many reports on studies regarding suppression of the gene expression of a target sequence by PIP. Moreover, the use of PIP as a drug candidate used for renal impairment, an anticancer agent, or a therapeutic agent for corneal injury, hyperplastic scar, bone disease, etc. has been studied based on animal experiments using mice. Furthermore, in recent years, also in the study of iCeMs, which is an iPS cell project conducted by Kyoto University as a part of studies regarding iPS cells, induction of iPS cells by PIP has been studied. Thus, PIP is an organic small molecule, regarding which various successful study results are expected.

Examples of the characteristics of PIP include: (1) possible designing of PIP, targeting any given gene sequence; (2) the binding ability of PIP to DNA, which is stronger than that of a transcriptional factor; (3) incorporation of PIP into the nucleus of a cell, without using vectors or drug delivery systems (DDS); (4) PIP, which is not decomposed by nucleic acid-decomposing enzyme, is stable in cells or living bodies, and is discharged as an undecomposed product from urine and/or bile; and (5) the N- and C-termini of PIP, which can be easily modified, so that PIP is able to form a complex with various functional small molecules.

In PIP, the Py/Im pair recognizes CG, the Py/Py pair recognizes AT or TA, and the Im/Py pair recognizes GC, so that the PIP is able to sequence-specifically bind to various any given double-stranded DNAs. PIP that binds to a target gene has been studied as a gene switch that inhibits the binding of a transcription factor to DNA and suppresses a specific gene expression.

Utilizing a PIP structure having high sequence recognition specificity, the present inventor had synthesized a complex of an alkylating functional group and PIP, and had succeeded in completing an invention relating to an indole derivative alkylating a specific nucleotide sequence of DNA (Patent Literature 2), and also, the inventor had synthesized a complex of a histone modification regulator and PIP, and had succeeded in completing an invention relating to a target gene-specific histone modification regulator (Patent Literature 1). However, it has not yet been reported that a drug, which targets the driver mutation of a driver oncogene (i.e., a genetic mutation that becomes a main cause of inducing cancer), has been synthesized based on the concept that is the use of PIP, and that the tumor-suppressing effect of the synthesized drug has been actually confirmed.

CITATION LIST

Patent Literature 1: WO 2010/001933
Patent Literature 2: WO 2005/087762

SUMMARY OF INVENTION

Technical Problem

As described above, it has been desired to develop a therapeutic agent specifically acting on the genetic mutation site of a driver oncogene(s). Hence, it is an object of the present invention to provide a novel alkylating agent that alkylates the genetic mutation site of a driver oncogene as a target.

Solution to Problem

As a result of intensive studies directed towards achieving the aforementioned object, the present inventor has designed a pyrrole-imidazole polyamide (PIP) that specifically binds to the genetic mutation site of a driver oncogene, and has then synthesized a compound by binding an alkylation reaction site to the designed PIP, so that the inventor has succeeded in synthesizing a novel compound that specifically recognizes the genetic mutation site of a driver oncogene and then alkylates it. The present inventor has further confirmed that the novel compound is efficiently delivered to tumor cells or tumor stem cells, thereby completing the present invention.

Specifically, the present invention is as follows.

(1) A complex of an alkylating agent conjugated with a DNA-binding compound specifically binding to the genetic mutation site of a driver oncogene.

(2) The complex according to (1) above, wherein the genetic mutation site is a change in the gene sequence and/or a change in the gene copy number.

(3) The complex according to (1) or (2) above, wherein the driver oncogene is at least one selected from among KRAS, HRAS, NRAS, BCR-ABL, EGFR, c-KIT, BRAF, PI3K, ALK, PIK3CA, FLT3, MET, BCL2, EML4-ALK, APC, BRCA1/2, TP53, MSH2, MLH1, MSH6, PMS2, RB1, PTEN, VHL, P16, MEN1, RET, CDH1, STK11, PTCH, Her2/neu, EGFR, MYC, MYCN and MET, and also among genes registered in the database of cancer gene mutation.

(4) The complex according to any one of (1) to (3) above, wherein the DNA-binding compound is any one of bridged nucleic acid, locked nucleic acid (LNA), PNA, a DNA-binding protein complex, pyrrole-imidazole polyamide (PIP), a pyrrole-imidazole polyamide (PIP) modified product, or a DNA-binding protein or a complex thereof.

(5) The complex according to any one of (1) to (4) above, wherein the alkylating agent is a compound having a functional group with an alkylation ability on a specific nucleotide sequence of DNA.

(6) The complex according to (5) above, wherein the alkylating agent is secoCBI.

(7) A driver oncogene mutation-specific alkylating agent comprising the complex according to any one of (1) to (6) above.

(8) The complex according to (1) above, which is represented by the following formula:

[Formula 1]

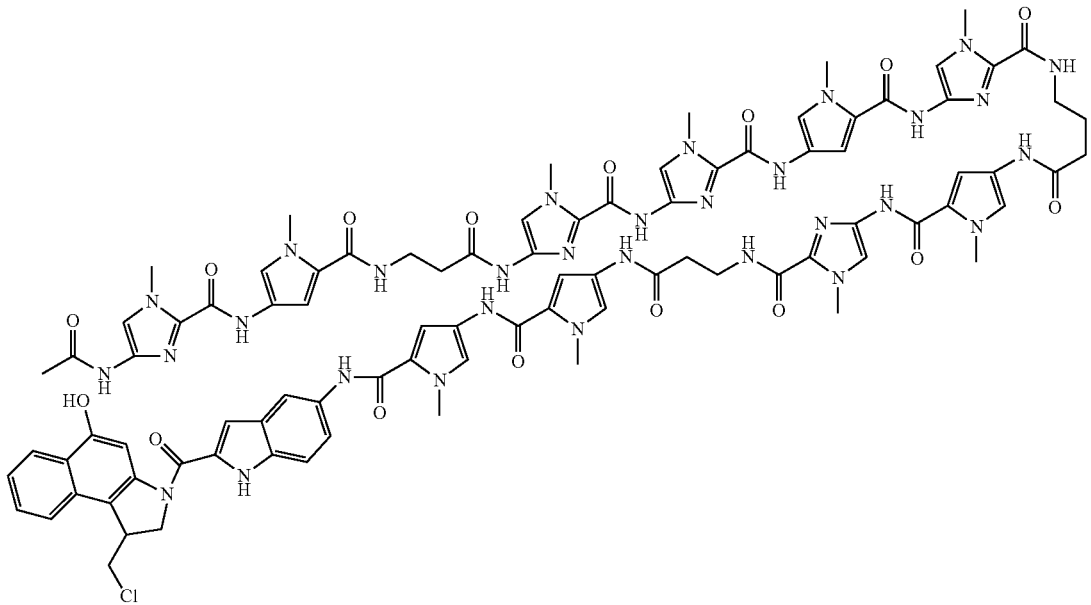

KR12

(9) The complex according to (1) above, which is represented by the following formula:
[Formula 2]
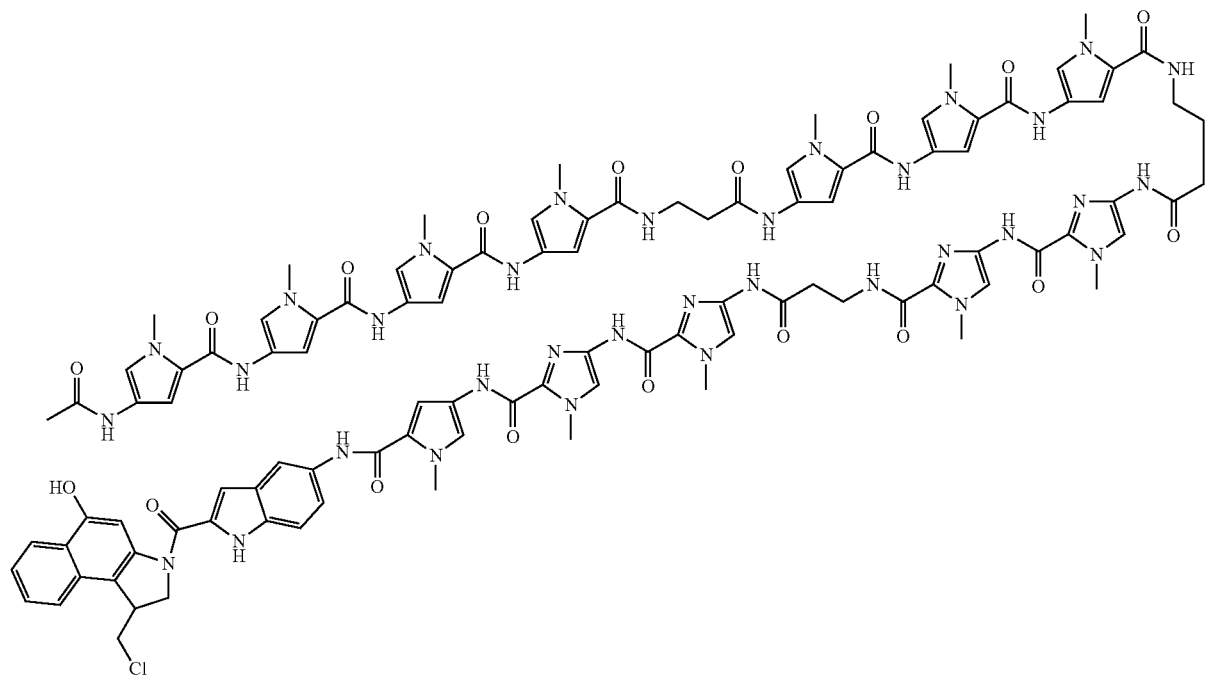
ALK-FL-1
(10) The complex according to (1) above, which is represented by the following formula:
[Formula 3]
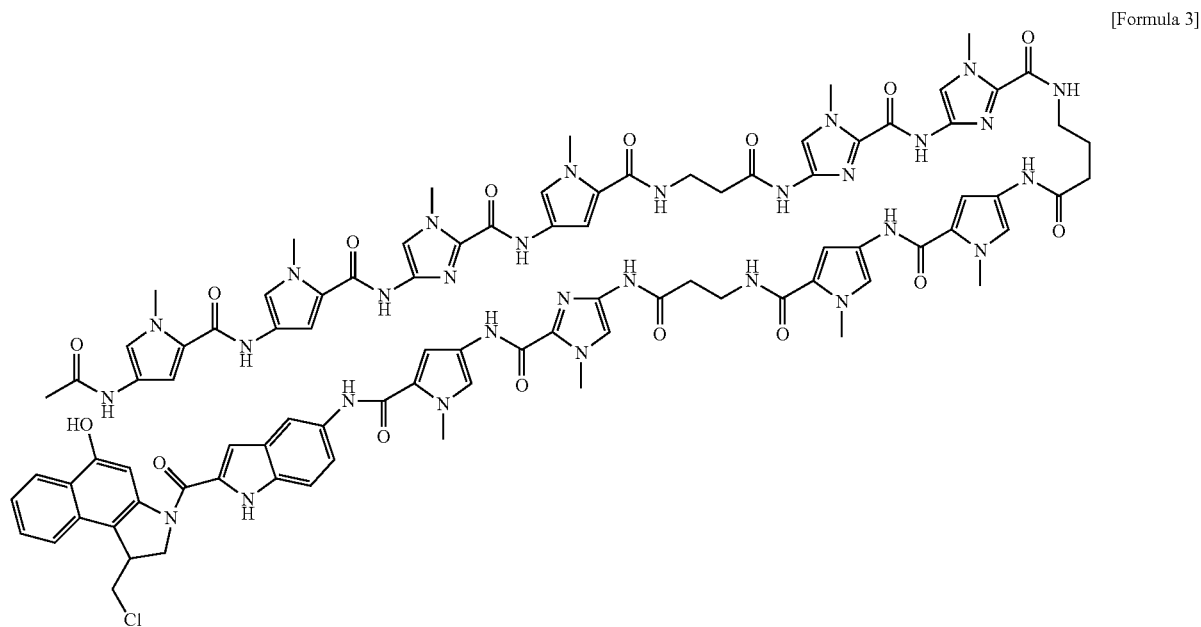
P3A-E5K-1

(11) The complex according to (1) above, which is represented by the following formula:
[Formula 4]
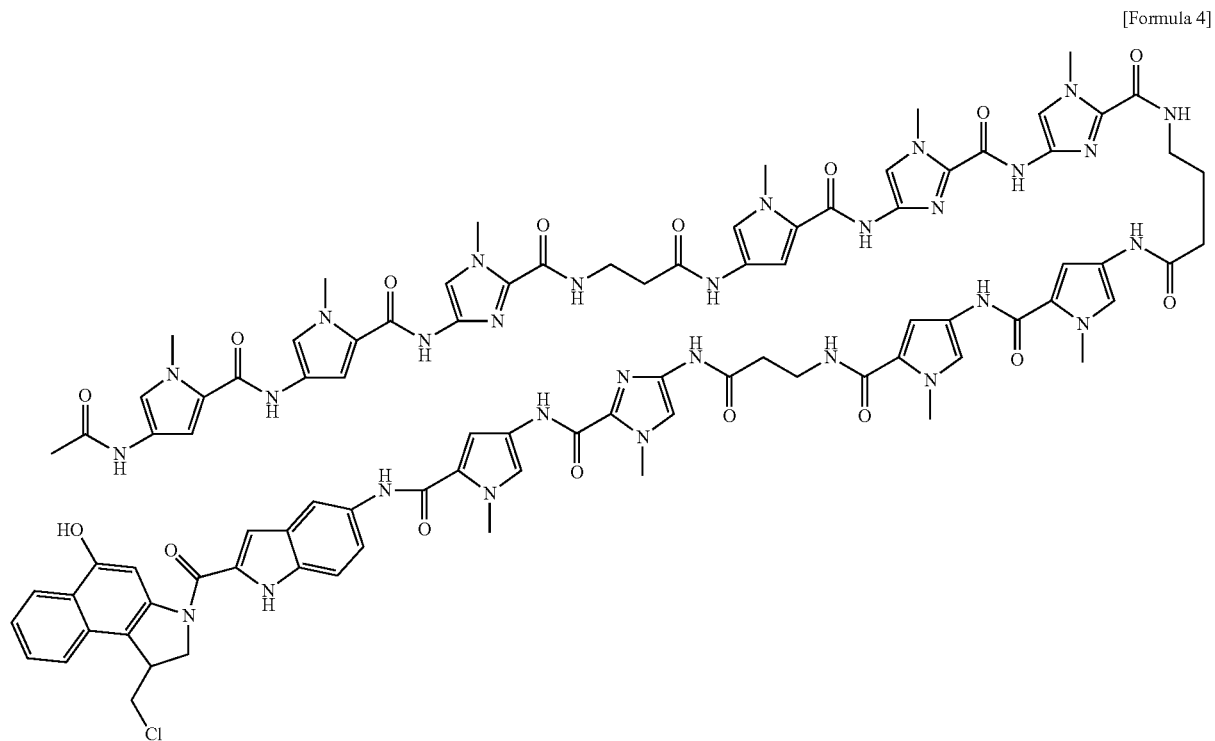
P3A-E5K-2
(12) The complex according to (1) above, which is represented by the following formula:
[Formula 5]
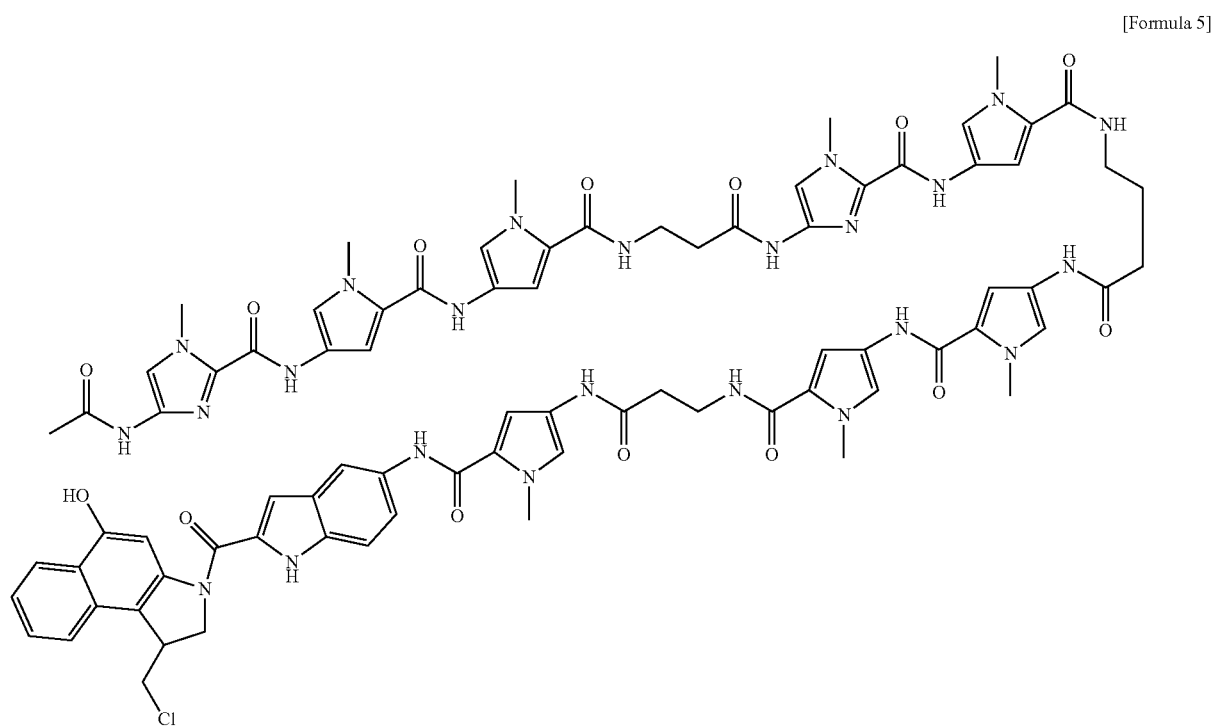
MYCNA1

(13) The complex according to (1) above, which is represented by the following formula:

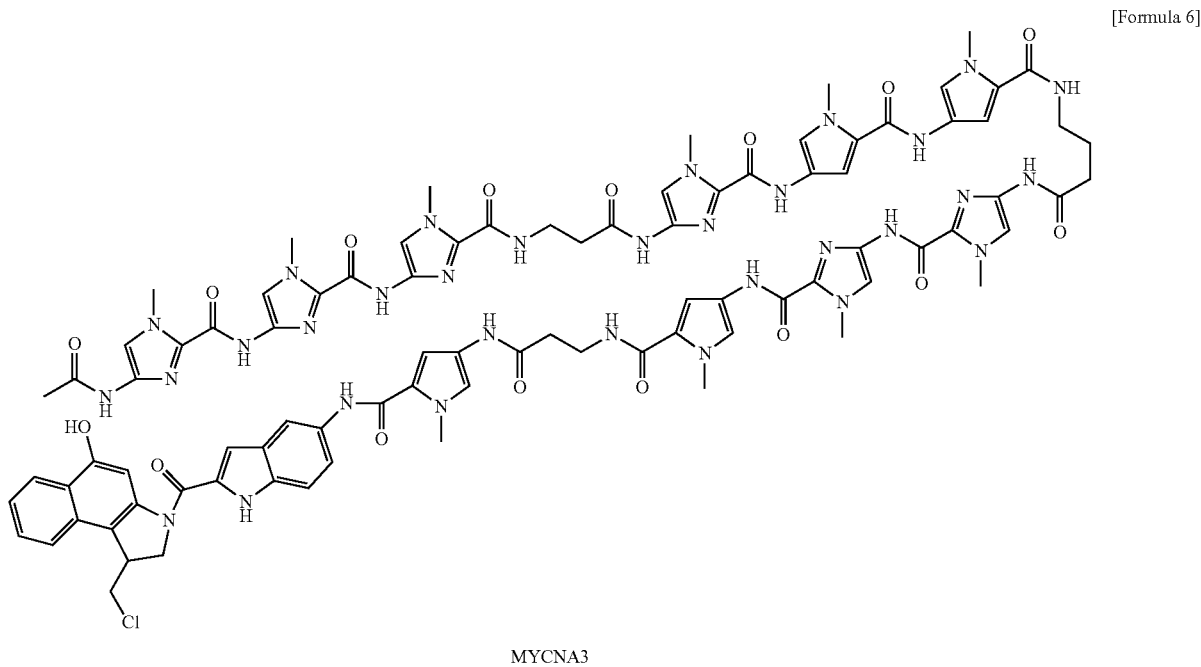

[Formula 6]

MYCNA3

(14) The KRAS gene codon 12 mutation-alkylating agent comprising the complex according to (8) above.
(15) The ALK gene F1174L mutation-alkylating agent comprising the complex according to (9) above.
(16) The PIK3CA gene E545K mutation-alkylating agent comprising the complex according to (10) or (11) above.
(17) The MYCN gene amplification mutation-alkylating agent comprising the complex according to (12) or (13) above.
(18) A pharmaceutical composition comprising the complex according to any one of (1) to (6) and (8) to (13) above.
(19) The pharmaceutical composition according to (18) above, which is an anticancer agent.
(20) A kit comprising the complex according to any one of (1) to (6) and (8) to (13) above.
(21) A research reagent kit comprising the complex according to any one of (1) to (6) and (8) to (13) above.
(22) A therapeutic kit comprising the complex according to any one of (1) to (6) and (8) to (13) above.
(23) A method for producing a complex that specifically alkylates the genetic mutation site of a driver oncogene, which comprises:
  (1) a step of designing a DNA-binding compound, such that it can specifically bind to the genetic mutation site of a driver oncogene; and
  (2) a step of binding the designed DNA-binding compound to an alkylating agent.
(24) The production method according to (23) above, wherein the genetic mutation site is a change in the gene sequence or a change in the gene copy number.
(25) The production method according to (23) or (24) above, wherein the driver oncogene is at least one selected from the group consisting of RAS, KRAS, HRAS, NRAS, BCR-ABL, EGFR, c-KIT, BRAF, PI3K, ALK, PIK3CA, FLT3, MET, BCL2, EML4-ALK, APC, BRCA1/2, TP53, MSH2, MLH1, MSH6, PMS2, RB1, PTEN, VHL, P16, MEN1, RET, CDH1, STK11, PTCH, Her2/neu, EGFR, MYC, MYCN and MET, and also, genes registered in the database of cancer gene mutation.
(26) The production method according to any one of (23) to (25) above, wherein the DNA-binding compound is any one of bridged nucleic acid, locked nucleic acid (LNA), PNA, a DNA-binding protein complex, pyrrole-imidazole polyamide (PIP), a pyrrole-imidazole polyamide (PIP) modified product, a DNA-binding protein, and a DNA-binding protein complex.
(27) The method for producing a complex according to any one of (23) to (26) above, wherein the alkylating agent is a compound having a functional group with an alkylation ability on a specific nucleotide sequence of DNA.
(28) The production method according to (27) above, wherein the alkylating agent is secoCBI.
(29) Use of a complex obtained by the production method according to any one of (23) to (28) above for the production of a pharmaceutical composition.
(30) Use of a complex obtained by the production method according to any one of (23) to (28) above for the production of an anticancer agent.

Effects of Invention

According to the present invention, a complex for specifically alkylating the target genetic mutation site of a driver oncogene in cancer cells is provided. According to a preferred aspect of the present invention, the complex of the present invention can be used as a pharmaceutical composition or an anticancer agent. According to another preferred aspect of the present invention, the complex of the present invention is a compound (KR12) that specifically alkylates the codon 12 mutation of a KRAS gene. According to a further preferred aspect of the present invention, the complexes of the present invention are compounds (MYCNA1, MYCNA2, and MYCNA3) that specifically alkylate MYCN genes whose genomic copy number has been increased. Moreover, according to a further preferred aspect of the present invention, the complexes of the present invention are ALK-FL-1 targeting the mutation of the ALK gene (F1174L), and P3A-E5K-1 and P3A-E5K-2 targeting the mutation of the PIK3CA gene (E545K).

According to the present invention, it has been revealed that a methodology of adding a polyamide specifically binding to the genetic mutation of a driver oncogene to an alkylating agent is an extremely effective approach for creating a novel anticancer agent that recognizes various tumor-specific mutations. Specifically, it has been revealed that an alkylating agent CBI is added to PIP that is a nucleotide sequence-specifically binding organic small molecule, so as to develop anti-mutated driver oncogene therapeutic agent that has a strong binding force with DNA and effectively suppresses gene expression even it is used in a small amount. It is considered that this effect can be obtained because DNA damage caused by alkylation induces cell death signals, and oncogenes suppressing such cell death are thereby suppressed, so that cells including cancer cells that do not generally cause cell death can be induced to cell death.

That is to say, the present invention provides a technique of delivering an alkylating agent to a specific genomic sequence, and by applying this technique, it becomes possible to successively design and/or synthesize therapeutic agents capable of specifically recognizing not only the sequence of a KRAS cancer gene, but also the mutated sequences of various driver cancer genes each having a cancer-specific mutation. Moreover, the same idea as the antibody-drug conjugate (ADC) technique can also be applied, and the synthesis can be easily carried out. Accordingly, the present technique can be applied to a wide range of intended uses.

The complex of the present invention, KR12, has excellent effects, such that it exhibits a strong anticancer activity specifically on cancer cells having a mutated RAS driver cancer gene, when it is used at a low concentration (which suppresses cell growth, when it is used at a picomole level), enables automatic synthesis, has a high accumulation/storage property in tumor, is localized in the nucleus, and has no side effects such as body weight reduction. Accordingly, the complex of the present invention, KR12, does not only provide a therapeutic agent for cancer bearing a RAS gene mutation that has become a clinical problem, but it also enables the development of a novel revolutionary therapeutic agent, with respect to a molecular target drug targeting to a mutant RAS, the development of which is considered to be difficult. In the future, it is anticipated that KR12 that is the complex of the present invention will be forwarded to developmental research directed towards the beginning of clinical trials (physical property test, stability test, pharmacokinetics, and mass synthesis at GMP). Moreover, if the method of the present invention were applied, it would be possible to develop further revolutionary therapeutic agents having the same effects as those of KR12.

MODE FOR CARRYING OUT THE INVENTION

Figure 1:
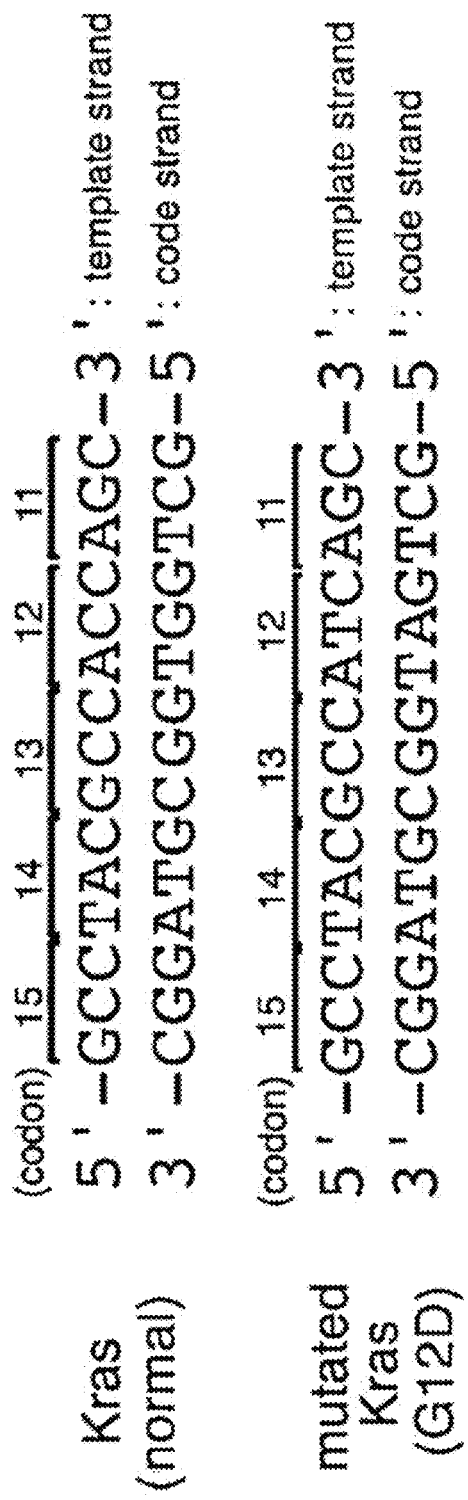
FIG. 1 is a view showing the codon 12 mutation (G12D) of the KRAS gene.

Hereinafter, the present invention will be described in detail. All publications cited in the present description, including prior art documents, and patent literatures such as published unexamined patent applications and patent publications, are incorporated herein by reference.

It has already been known that a gene sequence-specific alkylating agent can be synthesized using a PIP structure with high sequence recognition specificity. However, based on this concept, the applicability of such an alkylating agent as a drug for the treatment of disease has been unknown. In addition, it has been reported that the expression of a gene having a target sequence can be suppressed using a compound formed by conjugating an alkylating agent with PIP. However, the fact that a drug can be actually synthesized targeting the driver mutation of a driver oncogene and the synthesized drug is able to have a tumor-inhibitory effect has not yet been known. The present inventor has focused on the fact that an alkylating agent induces DNA damage, thereby inducing cell death, and that, in cancer, cancer cells become immortalized by a mechanism of suppressing the cell death due to DNA damage, and as a result, the cells continue to proliferate. It has been considered that a driver oncogene is deeply involved in immortalization of cancer cells, and it has been well known that cell death is suppressed, in particular, in KRAS gene mutation. Hence, the present inventor has hypothesized that if a drug capable of inducing DNA damage, while specifically suppressing codon 12 mutation, were synthesized, cell death could lead to cancer cells.

Based on this hypothesis, KR12 has been synthesized, and induction of cell death by KR12 has been compared between cancer cell lines having a codon 12 mutation that can be recognized by KR12 and cancer cell lines not having such a codon 12 mutation recognized by KR12. As a result, KR12 has induced the cancer cell lines having a codon 12 mutation that can be recognized by KR12 to cell death, even at an extremely low concentration. In addition, it has also been confirmed that KR12 specifically suppresses the transcription of the KRAS gene having a codon 12 mutation that can be recognized by KR12. Moreover, it has also been confirmed that KR12 can induce cell death, and that KR12 has a tumor growth-suppressing effect specifically on tumors having the mutation that can be recognized by the KR12, in human colon cancer xenografts that has been transplanted to a mouse, when the KR12 has been administered to the mouse. Based on these findings, the present inventors have discovered that KR12 suppresses the driver mutation of a target cancer gene, and also that KR12 is an anticancer agent capable of obtaining anticancer properties.

With regard to cancer cell lines having the ALK gene mutation (F1174L) and PIK3CA gene mutation (E545K), which are known as driver oncogene mutations, ALK-FL-1 targeting the ALK gene mutation (F1174L), and P3A-E5K-1 and P3A-E5K-2 targeting the PIK3CA gene mutation (E545K) have been synthesized, and have been then administered to the cancer cell lines each having the corresponding mutation. As a result, it has been confirmed that these complexes more effectively induce cell death and suppress cell growth.

Furthermore, the present inventors have considered that, as with KR12, when a compound alkylating a specific genomic sequence is produced, targeting a cancer gene with increased copy numbers as a result of amplification, the produced compound exhibits effects. Thus, the inventor has synthesized MYCN-alkylating PIPs (MYCNA1, MYCNA2, and MYCNA3), targeting MYCN that amplifies at a high frequency in infant neuroblastoma or the like and becomes a poor prognostic factor. The synthesized MYCNA1, MYCNA2 and MYCNA3 have suppressed the growth of neuroblastoma cells, in which the MYCN gene has been amplified. In particular, MYCNA3 more effectively has suppressed the cell growth of cells in which the MYCN gene amplification has strongly occurred, and it has had low effects on normal cells or other cancer cells.

From the aforementioned results, it has been revealed that a sequence-specific gene recognition polyamide compound can be synthesized, and further that anticancer agents targeting the driver mutations of various types of driver oncogenes can be synthesized by applying a method of synthesizing a complex conjugate of the aforementioned compound and a drug capable of inducing the alkylation of DNA.

Driver oncogene (essential proto-oncogene) means a proto-oncogene having a genetic mutation, which is considered to cause a mutation (e.g., point mutation, small deletion, insertion or translocation, amplification, etc.) specific to cancer cells, and to become a main cause of canceration. It is to be noted that deletion or translocation mutation includes a mutation, in which SNP (single nucleotide polymorphism) becomes heteroallelic in normal cells but becomes monoallelic or homoallelic in tumor cells. The driver oncogene of the present invention includes those registered in the database of cancer gene mutation. The cancer gene mutation database is, for example, COSMIC (Catalogue of somatic mutations in cancer), and the present cancer gene mutation database also includes other databases. The mutations of such a driver oncogene can be divided into two types, namely, (1) changes in gene sequences (e.g., point mutation, chromosomal translocation, deletion and/or insertion, wherein the deletion or translocation mutation includes a mutation, in which SNP (single nucleotide polymorphism) becomes monoallelic or homoallelic in tumor cells, although it becomes heteroallelic in normal cells), and (2) changes in gene copy numbers (i.e., increases in gene expressions). Examples of the driver oncogene having the above mutation (1) include KRAS, HRAS, NRAS, BCR-ABL, EGFR, c-KIT, BRAF, PI3K, ALK, PIK3CA, FLT3, MET, BCL2, EML4-ALK, APC, BRCA1/2, TP53, MSH2, MLH1, MSH6, PMS2, RB1, PTEN, VHL, P16, MEN1, RET, CDH1, STK11, and PTCH. Examples of the driver oncogene having the above mutation (2) include Her2/neu, EGFR, MYC, MYCN, and MET.

The RAS gene is a proto-oncogene belonging to the driver oncogene, which encodes a membrane-bound p21-ras protein with a molecular weight of approximately 21 kDa. The p21-ras protein is a low-molecular-weight guanylate pyrophosphatase (GTPase) that circulates between activated (RAS-GTP) and inactivated (RAS-GDP). The p21-ras protein is converted to an active type by guanine nucleotide exchange factor (GEF), and it is also converted to an inactive type by GTPase activating protein (GAP). Through such a conversion mechanism, the RAS gene regulates the activity of a signaling pathway associated with the growth and differentiation of cells, such as a MAP kinase pathway and a PI3 kinase pathway.

The RAS gene family includes three members, HRAS, KRAS and NRAS genes. The RAS gene is widely conserved among animal species. The RAS gene family includes proto-oncogenes. A mutated RAS gene family is observed in various cancers, and it is found in 20% to 30% of human carcinomas. In particular, KRAS gene mutation is a genetic mutation most commonly found in human carcinomas. KRAS gene mutation is identified at a high frequency in pancreatic cancer, colorectal cancer, thyroid cancer, lung cancer, head and neck cancer, and endometrial cancer, and further, it is also identified in precancerous states, such as myelodysplastic syndrome, adenoma of thyroid gland and colon, etc. Statistically, KRAS gene mutation is identified in approximately 35% to 40% of colon cancer, and in approximately 90% of pancreatic cancer.

As such a KRAS gene mutation, one base pair substitution (missense mutation) at codon 12, 13, 61 or 146 has been known. The frequencies are codon 12 (approximately 80%) and codon 13 (approximately 20%). If such a KRAS gene mutation occurring at a high frequency in cancer has actually occurred, a constantly activated p21-ras protein is expressed. Since this point mutant p21-ras protein does not become an inactivated type, it constantly activates a signaling pathway located downstream thereof. As a result, cells receive excessive growth signals, and cannot regulate their growth and differentiation, so that the cells are transformed into cancer cells.

The codon 12 mutation of the KRAS gene is a single nucleotide substitution mutation, such as GCT (Ala), GAT (Asp), CGT (Arg), TGT (Cys), AGT (Ser) or GTT (Val), to the codon 2 (wild type GGT, amino acid Gly) of exon 2 of the KRAS gene (Accession No.: NM 033360.2). If a mutation occurs in the codon 12 of the KRAS gene, a point mutation occurs in the P-loop of a p21-ras protein, and a constantly activated p21-ras protein is expressed. FIG. 1 shows a single nucleotide substitution mutation from GGT (Gly) to GAT (Asp).

Figure 2:
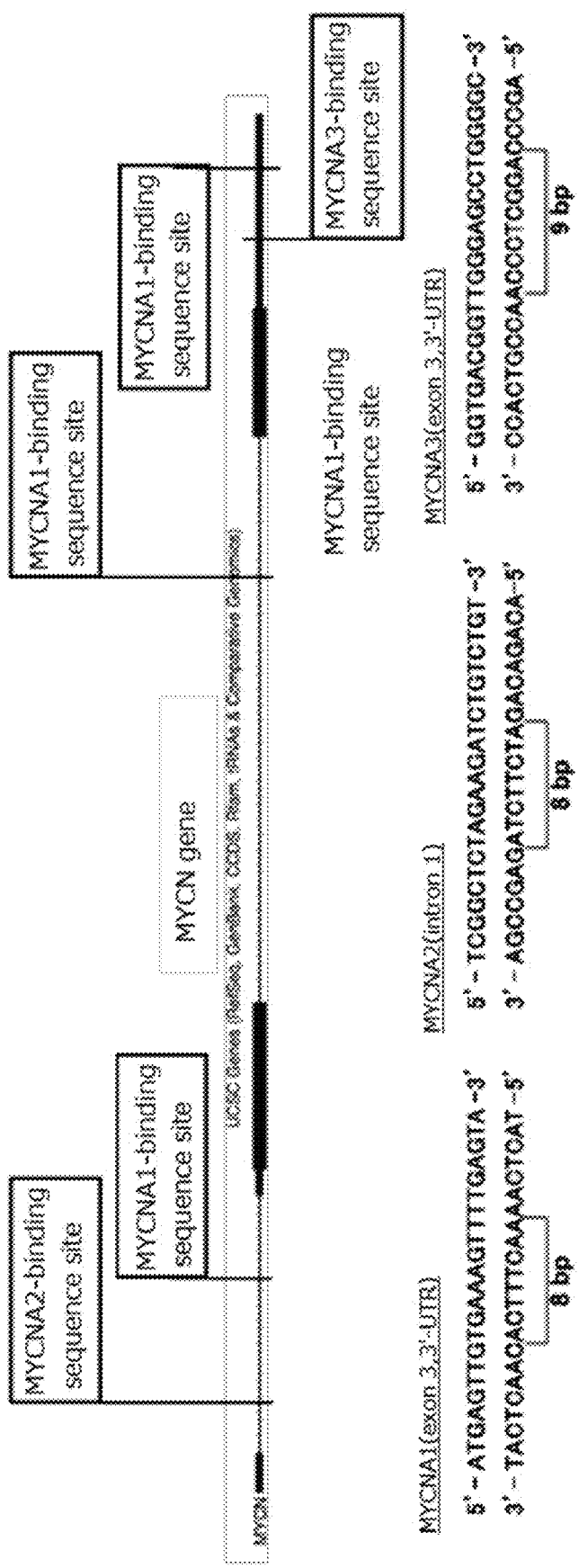
FIG. 2 is a view showing the binding positions of the MYCN gene with compounds.

The MYCN gene is a proto-oncogene belonging to the driver oncogene. Amplification of MYCN is found in 4% to 8% of early stages of neuroblastoma, and in approximately 30% of advanced stages thereof, and it has been known that such an amplification case has highly malignant phenotype. It has been known that the MYCN amplification is strongly associated with rapid progression of tumor and poor prognosis, and at present, the presence or absence of the MYCN amplification is considered to be an essential inspection item in therapeutic protocols based on the risk classification of neuroblastoma. FIG. 2 shows amplification portions of the MYCN gene.

Various diagnostic agents or therapeutic agents, which target the KRAS gene mutation and the MYCN gene amplification, have been developed so far. However, effective anticancer agents have not yet been developed under the current circumstance.

A driver oncogene mutation-recognizing polyamide, which is a constitutional element of a complex, is a polyamide designed to recognize the mutation of a driver oncogene. The phrase "to recognize a driver oncogene mutation" is used to mean that a driver oncogene mutation-recognizing polyamide binds to the mutated nucleotide sequence of a driver oncogene and/or a periphery thereof (for example, via a hydrogen bond or via a bond by crosslinking). Examples of a driver oncogene mutation-recognizing compound include pyrrole-imidazole polyamide (PIP) (a PIP compound having a cyclic structure, a hairpin structure, or a tandem structure in which such hairpin structures are connected), peptide nucleic acid (PNA), bridged nucleic acid, locked nucleic acid (LNA), a DNA-binding protein, such as a zinc finger, or a chimeric protein thereof, and DNA-binding compounds including complexes such as a DNA-binding protein complex or a guide RNA protein complex. Examples of such a driver oncogene mutation-recognizing compound further include modified products of PIP, which are formed by modifying PIP such that the binding ability of PIP to DNA can be maintained or improved. Examples of such a PIP modified product include a modified product formed by adding an amine to the position a or β of γ-aminobutyric acid of PIP, a modified product having a side chain comprising a substitution of N-α-N-γ-aminobutyric acid or N-β-N-γ-aminobutyric acid, modified products formed by modifying the aforementioned modified products with molecules such as FITC or biotin, a modified product formed by modifying the N-terminus of PIP with molecules such as FITC or biotin, and a modified product formed by modifying the C-terminus of PIP with molecules such as isophthalic acid. A pyrrole-imidazole polyamide (PIP) modified product.

Pyrrole-imidazole polyamide (PIP) is a polyamide comprising an N-methylpyrrole unit (Py), an N-methylimidazole unit (Im) and a γ-aminobutyric acid portion, in which Py, Im and the γ-aminobutyric acid portion are connected with one another via an amide bond (—C(═O)—NH—) (Trauger et al., Nature, 382, 559-61 (1996); White et al., Chem. Biol., 4, 569-78 (1997); and Dervan, Bioorg. Med. Chem., 9, 2215-35 (2001)). In such PIP, the γ-aminobutyric acid portion serves as a linker (a γ-linker), and the entire portion is folded to take a U-shaped conformation (a hairpin shape). In such a U-shaped conformation, across the linker, two strands comprising Py and Im are aligned in parallel. When a pair of Py and Im between the two strands has a specific combination (a Py/Im pair, an Im/Py pair, a Py/Py pair, or an Im/Im pair), such a pair can bind to a specific base pair in DNA with high affinity. For example, the Py/Im pair can bind to a C-G base pair, and the Im/Py pair can bind to a G-C base pair. In addition, the Py/Py pair can bind to both of an A-T base pair and a T-A base pair (White et al., Chem. Biol., 4, 569-78 (1997); Dervan: Bioorg. Med. Chem., 9, 2215-35 (2001)). Moreover, PIP may also comprise 3-hydroxypyrrole (Hp) or β alanine. Regarding Hp, a Hp/Py pair can bind to a T-A base pair (White et al., Nature, 391, 468-71 (1998)). Furthermore, the γ-linker has a side chain such as N-α-N-γ-aminobutyric acid and N-β-N-γ-aminobutyric acid having an amino group, and these may be modified with molecules such as FITC or biotin. Further, the N-terminus of PIP may be modified, not only with an acetyl group, but also with molecules such as FITC or biotin. The β alanine/β alanine can bind to a T-A base pair or an A-T base pair. As such, by changing the combination of the Py/Im pair depending on a target DNA sequence, PIP, which recognizes the control region of a target gene, can be designed. The method of designing PIP and the method of producing PIP are known (e.g., Japanese Patent No. 3045706, JP Patent Publication (Kokai) No. 2001-136974 A, and WO 03/000683).

Figure 7:
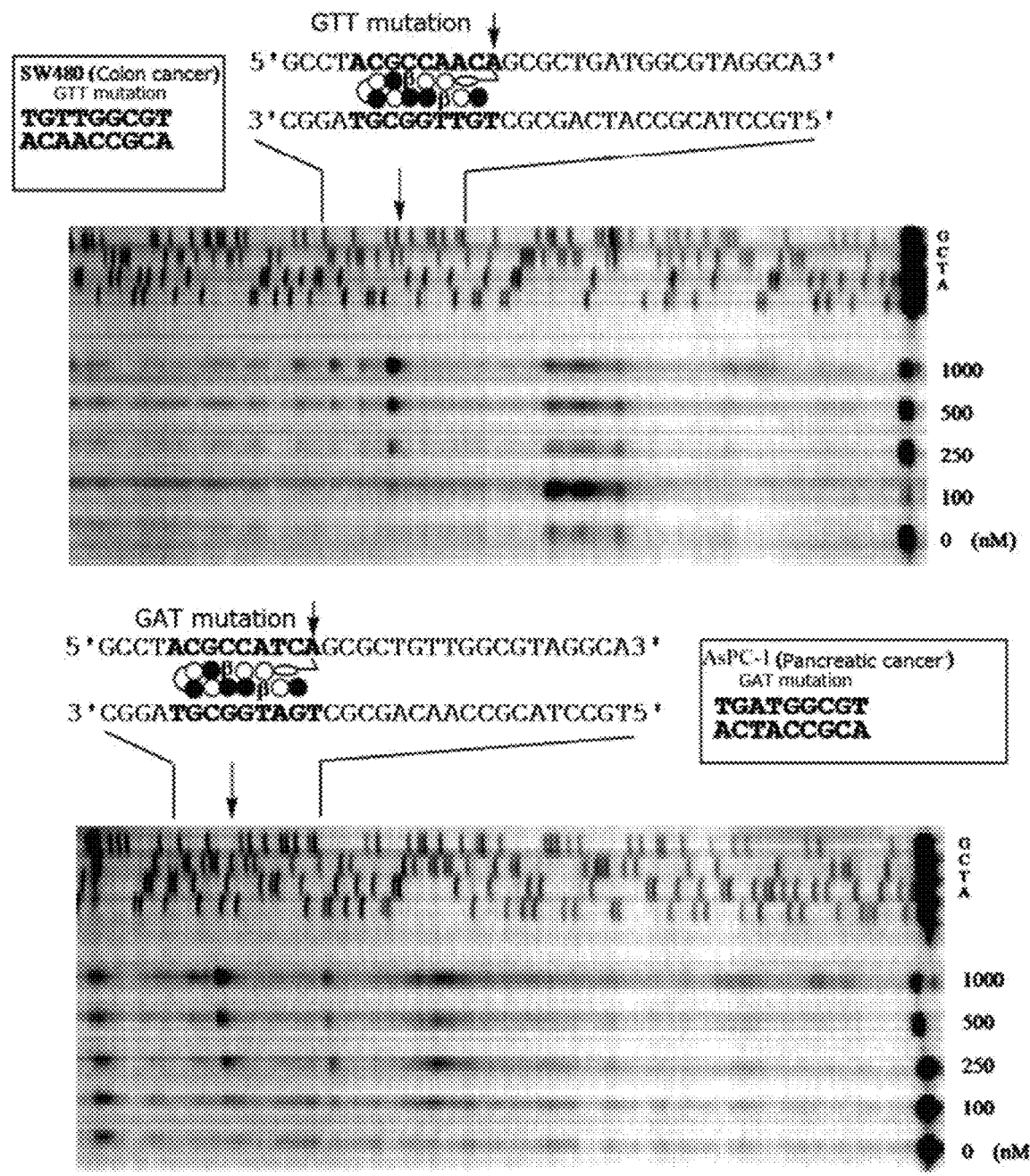
FIG. 7 is a view showing the results of an experiment for confirming alkylation of the nucleotide sequence of the codon 12 mutation of the KRAS gene.

PIP can recognize a gene sequence. Thus, in order to allow PIP to recognize, for example, the mutations G12D and G12V of the driver oncogene KRAS, in which GGT is converted to GAT or GTT, as shown in FIG. 1, a polyamide has been designed, not using a pair of imidazole and pyrrole recognizing guanine and cytosine, but using a pair of pyrrole and β alanine recognizing adenine and thymine. Moreover, by disposing an indole group between a pyrrole group and secoCBI, the polyamide has been synthesized such that an alkylation site is located close to the N3 of adenine on the basis of structure analysis, so as to obtain a good angle. Furthermore, considering that the transcription template DNA of KRAS can be alkylated, KR12 has been designed. As shown in FIG. 7, KR12 has been synthesized as a compound that recognizes the G12D mutation 5'-ACGC-CATCA-3' and the G12V mutation 5'-ACGCCAACA-3', and alkylates the N3 of the adenine at the 3' terminus. Thus, with regard to nucleotide substitution, by utilizing the nucleotide-recognizing ability of PIP or the adenine-recognizing ability of secoCBI, a compound, which is capable of recognizing various point mutations or SNP (single nucleotide polymorphism) that becomes monoallelic or homoallelic in tumor and becomes heteroallelic in normal cells, can be synthesized, and it can be anticipated that thus synthesized compound will have an antitumor effect.

Bridged nucleic acid or locked nucleic acid (LNA) can be synthesized as 2',4'-BNA, which is formed by allowing a compound to recognize the control region of a target gene and then bridging with an ethylene chain between the 2' oxygen atom and 4' carbon atom of RNA, or as 2',4'-ENA (ethylene-bridged nucleic acids), which is formed by allowing a compound to recognize the control region of a target gene and then bridging with an ethylene chain between the 2' oxygen atom and 4' carbon atom of RNA. LNA can also be purchased from Proligo.

An alkylating agent comprises a compound having a functional group that alkylates DNA. Such an alkylating agent is not particularly limited, as long as it comprises a compound having both an alkylation ability and a sequence-recognizing ability on a specific nucleotide sequence present in DNA. For example, the compound comprising a functional group described in WO 2010/001933 can be used. The alkylating agent introduces an alkyl group into the guanine N-7 position or adenine N-3 position of DNA and causes adduct formation or a crosslinking reaction between guanine residues, adenine residues or the like. A double-stranded DNA generating such a crosslinking reaction or a double-stranded DNA involving adduct formation is hardly repaired by a repair mechanism, and consequently, the transcription and replication of DNA become impossible. As a result, termination of cell growth or cell death caused by apoptosis is induced. The DNA-binding protein includes a binding protein such as zinc finger, a chimeric protein such as TALEN (TALE Nuclease), and a conjugated protein such as CRISPR utilizing a guide nucleic acid.

secoCBI (1-chloromethyl-5-hydroxy-1,2-dihydro-3H-benzo[e]indole) is a compound represented by the following formula 7. secoCBI is a known compound that alkylates DNA. secoCBI can be synthesized by methods described in known publications ((a) Boger, D. L.; Yun, W. Y.; Teegarden, B. R. J. Org. Chem. 1992, 57, 2873. (b) Boger, D. L.; McKie, J. A. J. Org. Chem. 1995, 60, 1271. (c) Boger, D. L.; Ishizaki, T.; Kitos, P. A.; Suntomwat, 0. J. Org. Chem. 1990, 55, 5823).

[Formula 7]

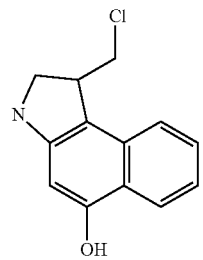

The complex of the present invention can be synthesized, for example, by binding the above-described polyamide with the above-described alkylating agent. The synthesis can be carried out according to a known method (J. Am. Chem. SOC. 1995, 117, 2479-2490). The "binding" may be carried out, directly or via a linker. The linker is not particularly limited, as long as it does not prevent the action of the alkylating agent and also does not prevent the polyamide from recognizing the genetic mutation site of a driver oncogene. Examples of the linker include an amide bond, a phosphodisulfide bond, an ester bond, a coordination bond, and an ether bond.

The alkylating agent comprising the complex of the present invention may also comprise a carrier or an additive, as well as the complex of the present invention, depending on intended use. Examples of such a carrier and an additive include water, acetic acid, an organic solvent, collagen, polyvinyl alcohol, polyvinyl pyrrolidone, a caroboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, agar, polyethylene glycol, diglycerin, glycerin, propylene glycol, Vaseline, paraffin, stearyl alcohol, stearic acid, human serum albumin, mannitol, sorbitol, lactose, and a surfactant. The use amount of the complex of the present invention can be regulated, as appropriate, depending on intended use.

Examples of the complex of the present invention include the following complexes.

[Formula 8]
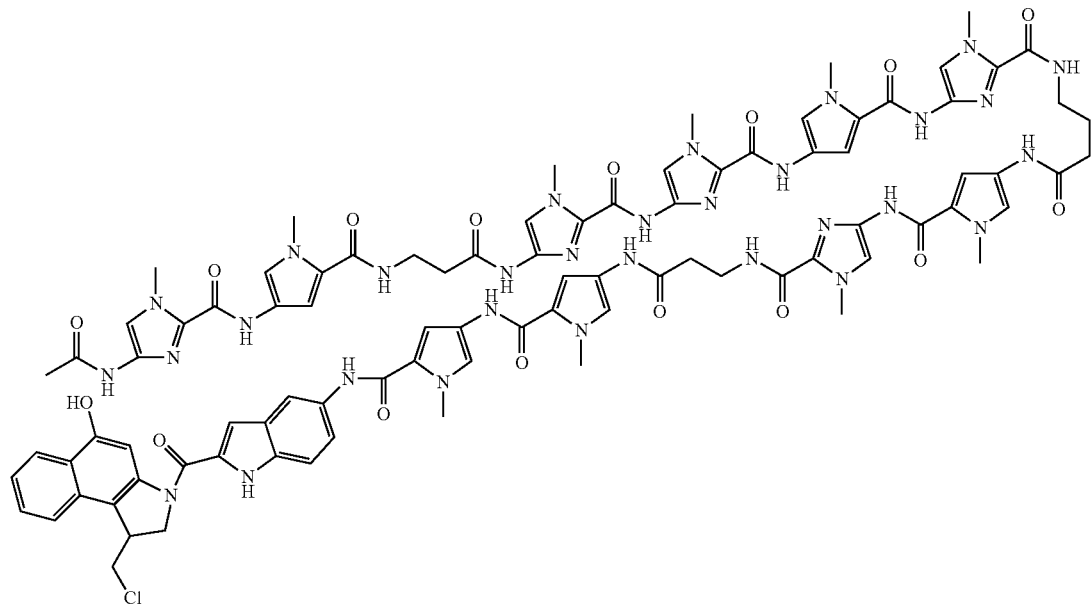
KR12
[Formula 9]
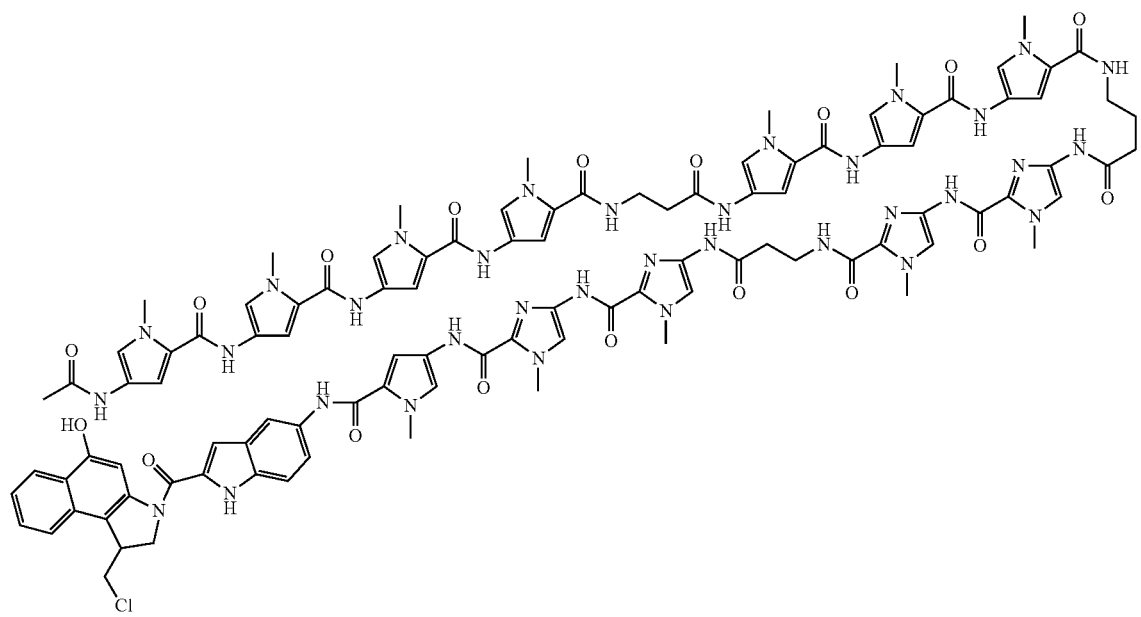
ALK-FL-1

[Formula 10]
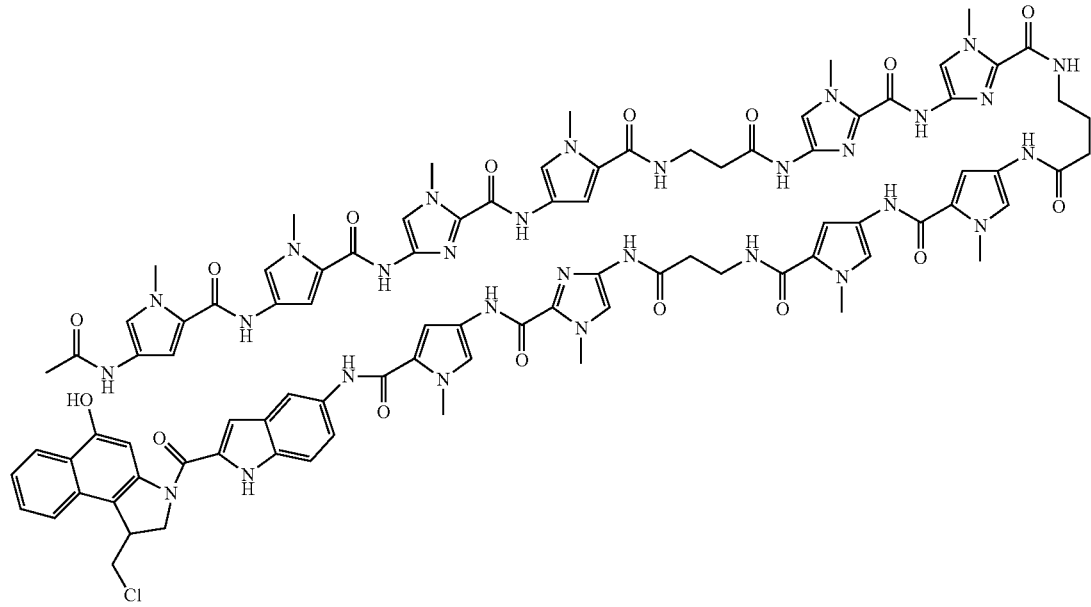
P3A-E5K-1
[Formula 11]
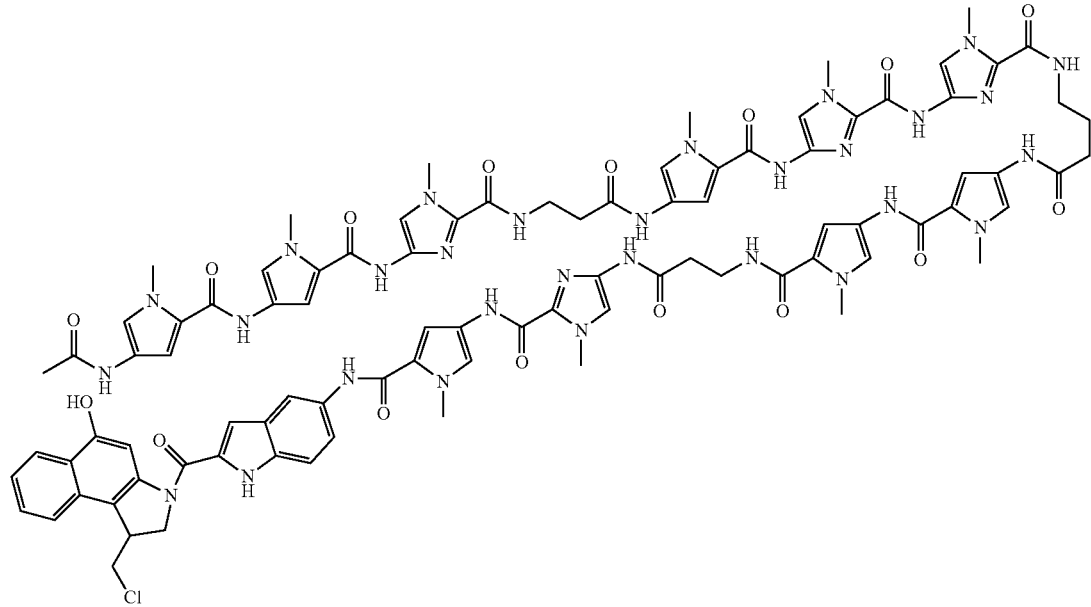
P3A-E5K-2

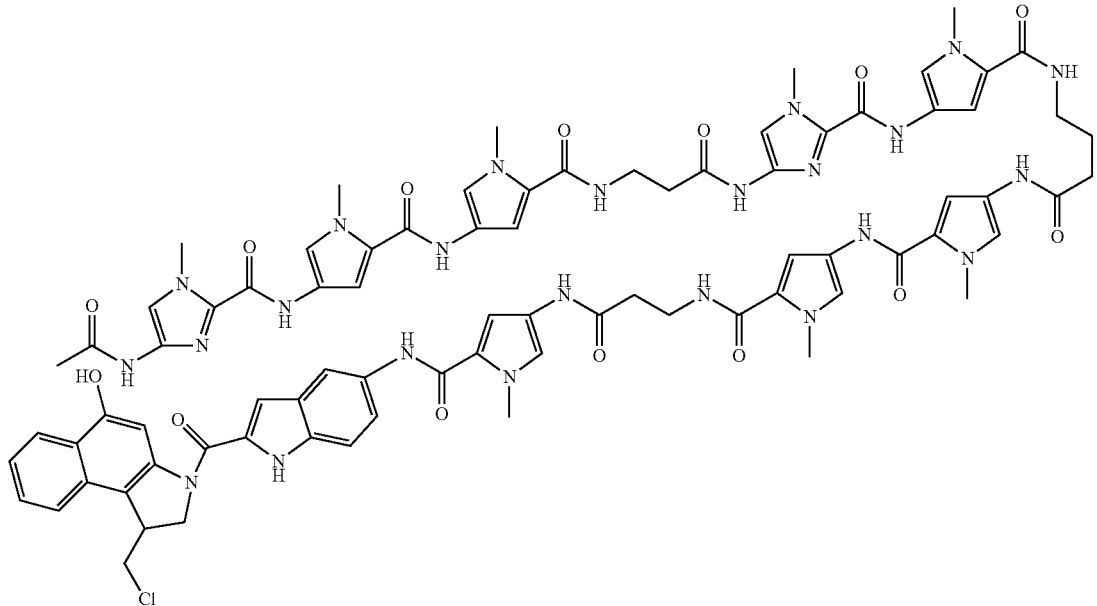

MYCNA1

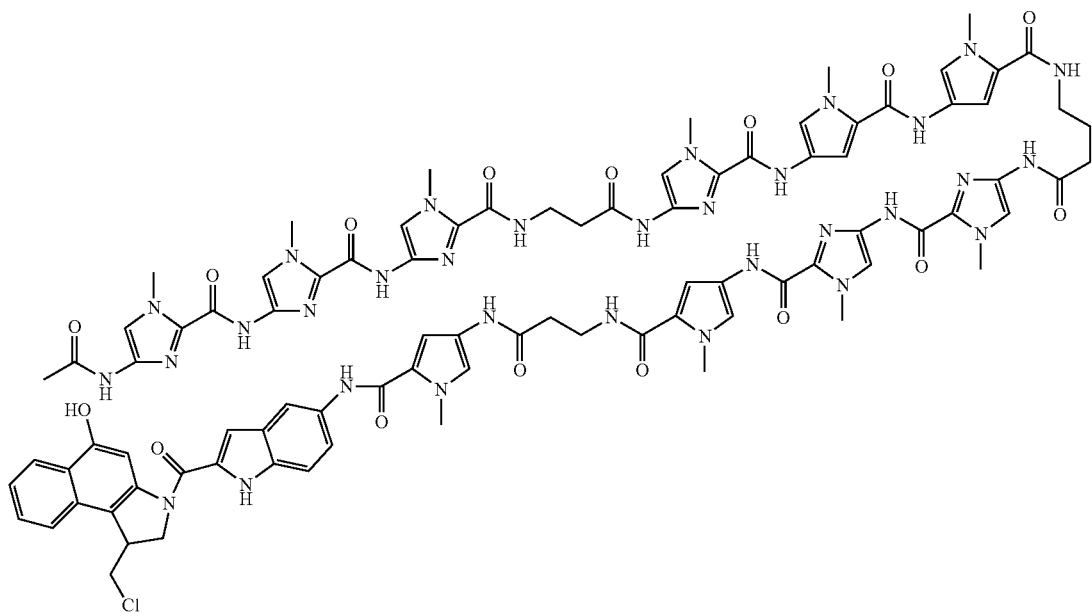

MYCNA3

The pharmaceutical composition of the present invention is a composition comprising the above-described complex. By administering this pharmaceutical composition into a living body, various diseases can be treated and prevented. The pharmaceutical composition of the present invention can target the diseases of all organisms, and particularly mammals (e.g., a human, a rat, a rabbit, a sheep, a swine, a bovine, a cat, a dog, a monkey, etc.), which utilize double-stranded DNA for biological control. Examples of the target disease of the pharmaceutical composition of the present invention include diseases involving genetic mutation, such as cancer, nervous disease/mental disease, lifestyle-related disease, sleep disorder, diseases having strong local symptoms in a dermatological, ophthalmological or otolaryngological region, infectious disease, allergic disease, disease associated with cellular senescence, thyroid hormone resistance, aging, cystic fibrosis, and digestive disease. Among such target diseases, examples of the cancer include brain tumor, neck cancer, esophageal cancer, tongue cancer, lung cancer, breast cancer, pancreatic cancer, stomach cancer, cancer of small intestine or duodenum, colon cancer (colon cancer, rectal cancer), bladder cancer, kidney cancer, liver cancer, prostate cancer, uterine cancer, ovary cancer, thyroid cancer, gallbladder cancer, pharyngeal cancer, sarcoma (e.g., osteosarcoma, chondrosarcoma, Kaposi's sarcoma, myosarcoma, angiosarcoma, fibrosarcoma, etc.), leukemia (e.g., chronic myelogenous leukemia (CML), acute myelogenous leukemia (AML), chronic lymphocytic leukemia (CLL) and acute lymphocytic leukemia (ALL), lymphoma, multiple myeloma (MM), etc.), childhood solid tumor (brain tumor, neuroblastoma, hepatoblastoma, nephroblastoma, Ewing tumor, etc.), retinoblastoma, and melanoma. The lifestyle-related disease is not particularly limited, and examples include hyper tension and diabetes. Examples of the disease having strong local symptoms in a dermatological, ophthalmological or otolaryngological region include psoriasis, chronic dermatitis, sinusitis, glaucoma, and retinal degeneration. Examples of the allergic disease include atopic dermatitis and hay fever. Examples of the disease associated with cellular senescence include skin wrinkling, sagging skin, and pigmentation. Examples of the nervous disease/mental disease include manic state, depression, schizophrenia, autism, bipolar disorder, Alzheimer's disease, sleep disorder, and dementia.

Preferred target diseases of the pharmaceutical composition of the present invention include all diseases derived from driver oncogene mutation. All diseases derived from KRAS gene codon 12 mutation, MYCN gene amplification, ALK gene mutation (F1174L) and PIK3CA gene mutation (E545K) are also included in the target diseases. Examples of such target diseases include colon cancer, pancreatic cancer, colorectal cancer, thyroid cancer, lung cancer, head and neck cancer, endometrial cancer, myelodysplastic syndrome, adenoma of thyroid gland and colon, and neuroblastoma. The pharmaceutical composition of the present invention more effectively acts on cells having a driver oncogene mutation, rather than on normal cells. The present pharmaceutical composition alkylates such cells to promote the crosslinking of DNA, and induces a cell death mechanism caused by DNA damage. The present pharmaceutical composition further suppresses the expression of a driver oncogene and inhibits cell growth, resulting in the death of disease-causing cells, so that it can treat or prevent the disease.

The pharmaceutical composition of the present invention may have a dosage form either for oral administration or for parenteral administration. These dosage forms can be formulated according to ordinary methods, and may comprise a pharmaceutically acceptable carrier or additive. Examples of such a carrier and an additive include water, acetic acid, a pharmaceutically acceptable organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, agar, polyethylene glycol, diglycerin, glycerin, propylene glycol, vaseline, paraffin, stearyl alcohol, stearic acid, human serum albumin, mannitol, sorbitol, lactose, and a surfactant acceptable as a pharmaceutical additive.

One additive or a combination of additives can be selected, as appropriate, from the above-described additives, depending on the dosage form of the pharmaceutical composition of the present invention. Examples of the dosage form applied in the case of oral administration include a tablet, a capsule, a fine granule, a powder agent, a granule, a liquid agent, syrup, a spray agent, an ointment, an eye drop and an external agent, and the present pharmaceutical composition can be administered in a suitable dosage form. An example of the dosage form in the case of parenteral administration is an injection-type agent. In the case of such an injection-type agent, the present pharmaceutical composition can be systemically or locally administered, for example, as an intravenous injection such as drip infusion, subcutaneous injection, intraperitoneal injection, or intratumor injection.

For example, in the case of using the pharmaceutical composition as an injection preparation, the pharmaceutical composition of the present invention is dissolved in a solvent (e.g., a normal saline, a buffer, a glucose solution, 0.1% acetic acid, etc.), and suitable additives (human serum albumin, PEG, a mannose-modified dendrimer, a cyclodextrin conjugate, etc.) are then added to the obtained solution. The obtained mixture can be used as an injection preparation. Otherwise, a dosage form that is freeze-dried and is then melted before use may also be applied. As excipients for freeze-drying, sugar alcohols such as mannitol or glucose, or sugars, can be used.

The applied dose of the pharmaceutical composition of the present invention or the compound of the present invention is different, depending on age, sex, symptoms, administration route, the number of doses, and dosage form. In the case of an adult (60 kg), the applied dose is, for example, 0.01 to 1000 mg, preferably 0.1 to 100 mg, and more preferably 1 to 30 mg, per day. The administration method is appropriately selected, depending on the age and symptoms of a patient. Administration may be carried out, for example, at intervals of several days, once or divided to 2 to 4 times per day.

The pharmaceutical composition of the present invention can be used as an anticancer agent. Examples of the type of a target cancer include, but are not limited to, colon cancer, pancreatic cancer, colorectal cancer, thyroid cancer, lung cancer, neck cancer, endometrial cancer, myelodysplastic syndrome, adenoma of thyroid gland and colon, and neuroblastoma. All cancers derived from driver oncogene mutation, and all cancers derived from KRAS gene codon 12 mutation or MYCN gene amplification, are targets. As in the case of the aforementioned pharmaceutical composition and alkylating agent, the anticancer agent of the present invention may comprise a carrier or a composition, depending on intended use.

The kit of the present invention comprises a pharmaceutically acceptable carrier or additive, a reagent, an auxiliary agent, a special container, other necessary accessories, an instruction manual, etc., as well as the compound of the present invention. The kit of the present invention can also be used as a cancer-treating kit or as a research reagent kit.

Hereinafter, the present invention will be more specifically described in the following examples. However, these examples are not intended to limit the scope of the present invention.

Example 1

1. Overview

The codon 12 mutations of the KRAS gene is genetic mutations, which are frequently observed in pancreatic cancer that has been recently most difficult to be treated, and also in patients suffering from colon cancer or lung cancer, which has metastasis and resistant to chemotherapy. At present, it has been desired to develop a therapeutic agent effective for the KRAS gene codon 12 mutations. In the present example, hairpin PIP (hPIP) targeting the mutated sequence of the codon 12 of a KRAS gene was conjugated with secoCBI that specifically alkylates adenine on the minor groove side of DNA nucleotides, so as to synthesize hPIP-secoCBI (KR12) that specifically recognizes the codon 12 mutation of the KRAS gene. Using the thus synthesized KR12, the following operations were carried out: (1) an experiment for confirming alkylation of the nucleotide sequence of the KRAS gene codon 12 mutation, (2) the measurement of a 50% inhibitory concentration to colon cancer cells, (3) observation of cell growth and cell morphology, (4) the analysis of a change in cell cycle, (5) semi-quantitative gene expression analysis, (6) colony sequencing, (7) the measurement of RAS activity, (8) an experiment for evaluating suppression of the xenograft tumor of nude mice, into which colon cancer cells have been transplanted, (9) an experiment for confirming incorporation of KR12 into cancer cells and sphere-forming cells and avoidance from a drug excretion mechanism, and (10) an experiment for confirming accumulation of the KR12 in the nucleus of a tumor cell.

KR12 had a sufficient tumor growth-suppressing ability on colon cancer cells having the KRAS gene codon 12 mutation, even when it is used at a low concentration, and exhibited statistically significant tumor growth-suppressing effects on nude mice, into which LS180 cells (derived from colon cancer) having the KRAS gene codon 12 mutation in a heteroallelic state have been subcutaneously transplanted. KR12 also exhibited tumor-reducing effects on a tumor formed by transplantation of SW480 cells (derived from colon cancer) having the KRAS codon 12 mutation in a homoallelic state. On the other hand, KR12 did not exhibit such suppressing effects on HT29 cells (derived from colon cancer) having a wild-type KRAS gene. From these results, it has been revealed that KR12 exhibits tumor growth-suppressing effects in vitro and in vivo on cancer cells having the KRAS gene codon 12 mutation.

From these results, it has been found that KR12 has the effect of specifically alkylating the nucleotide sequence of the codon 12 mutation of the KRAS gene, selectively inhibiting the expression of the KRAS gene having such codon 12 mutation, and specifically suppressing the growth of cancer cells caused by the codon 12 mutation of the KRAS gene. These results suggest that a methodology of conjugating PIP with an alkylation moiety would be an approach extremely effective for the discovery of novel anticancer agents recognizing various tumor-specific mutations.

2. Synthesis of Alkylating PIP Targeting the Codon 12 Mutation of the KRAS Gene (KR12)

Figure 3:
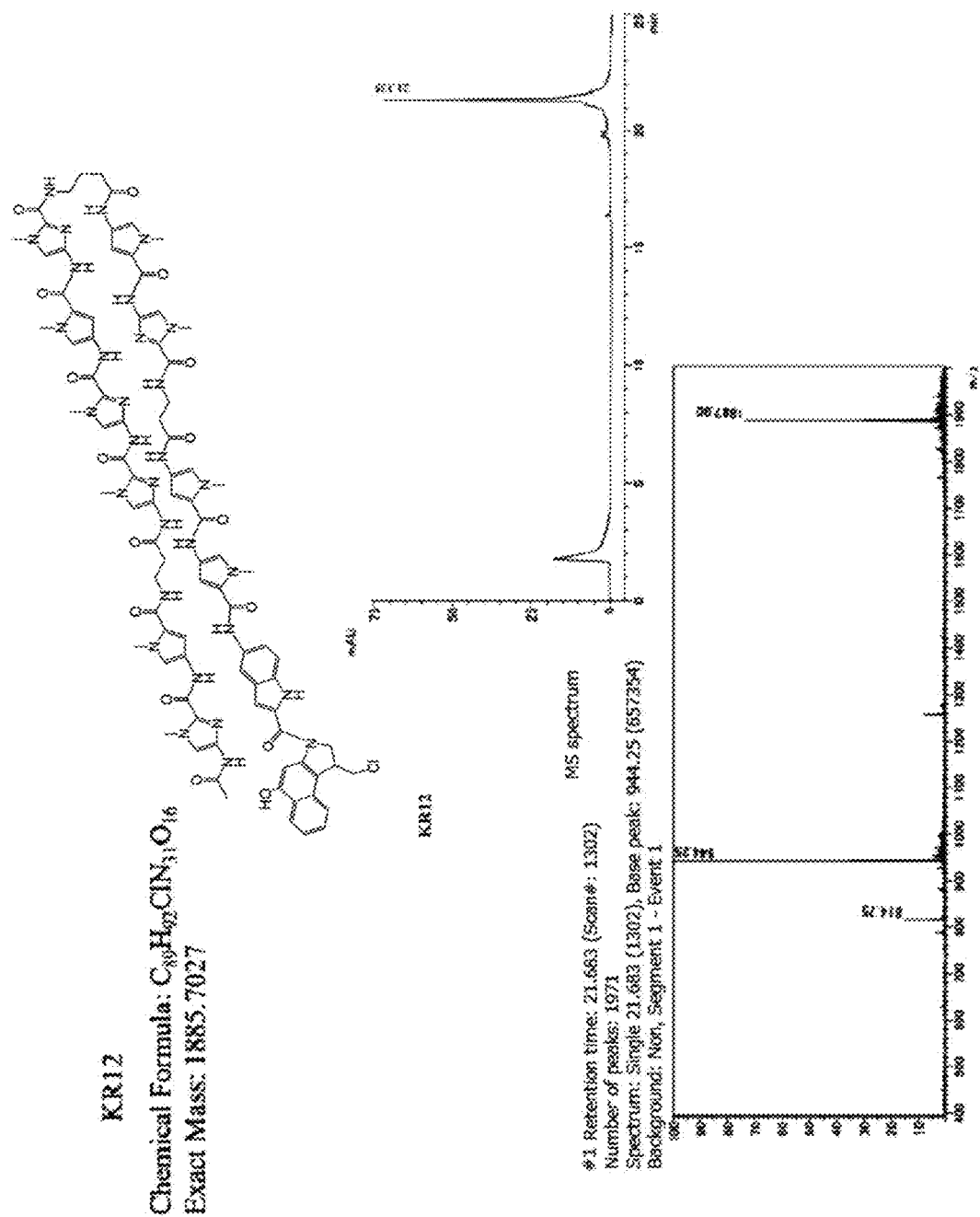
FIG. 3 is a view showing the chromatograms of HPLC and LC-MS, which are related to the synthesis of PIP (KR12) that alkylates the codon 12 mutation of the KRAS gene.

The chemical structure of alkylating PIP targeting the codon 12 mutation of a KRAS gene (KR12) is represented by a chemical formula 14 as shown below. A method for producing the compound of the present invention is as follows. PIP having a carboxylic acid terminus was dissolved in 100 μL of DMF, and thereafter, iPr2NEt (0.5 μL, 2.86 μmop and Py BOP (1.0 mg, 1.95 μmol) were added to the above solution. While stirring, the reaction solution was reacted at room temperature for 2 hours. Thereafter, formation of an active form of 1-hydroxybenzotriazole ester was confirmed by HPLC. After the formation had been confirmed, $NH_2$-indole seco-CBI (0.6 mg, 1.58 μmol) was added to the reaction vessel, and the mixture was then stirred at room temperature in a nitrogen atmosphere overnight. Thereafter, DMF used as a solvent was removed, and the residue was subjected to liquid separation using dichloromethane and diethyl ether. The layer of reaction product was purified by HPLC (0.1% TFA/CH3CN, 30%-75% linear gradient, 0 to 30 minutes), and was then freeze-dried, so as to obtain a compound of interest, alkylating PI polyimide (KR12) targeting the codon 12 mutation of the KRAS gene, in the form of white powders (LC-MSm/e $C_{89}H_{94}ClN_{31}O_{16}$ [M+2H]2+; calculated value: 943.86; measured value: 944.25; FIG. 3).

Figure 4:
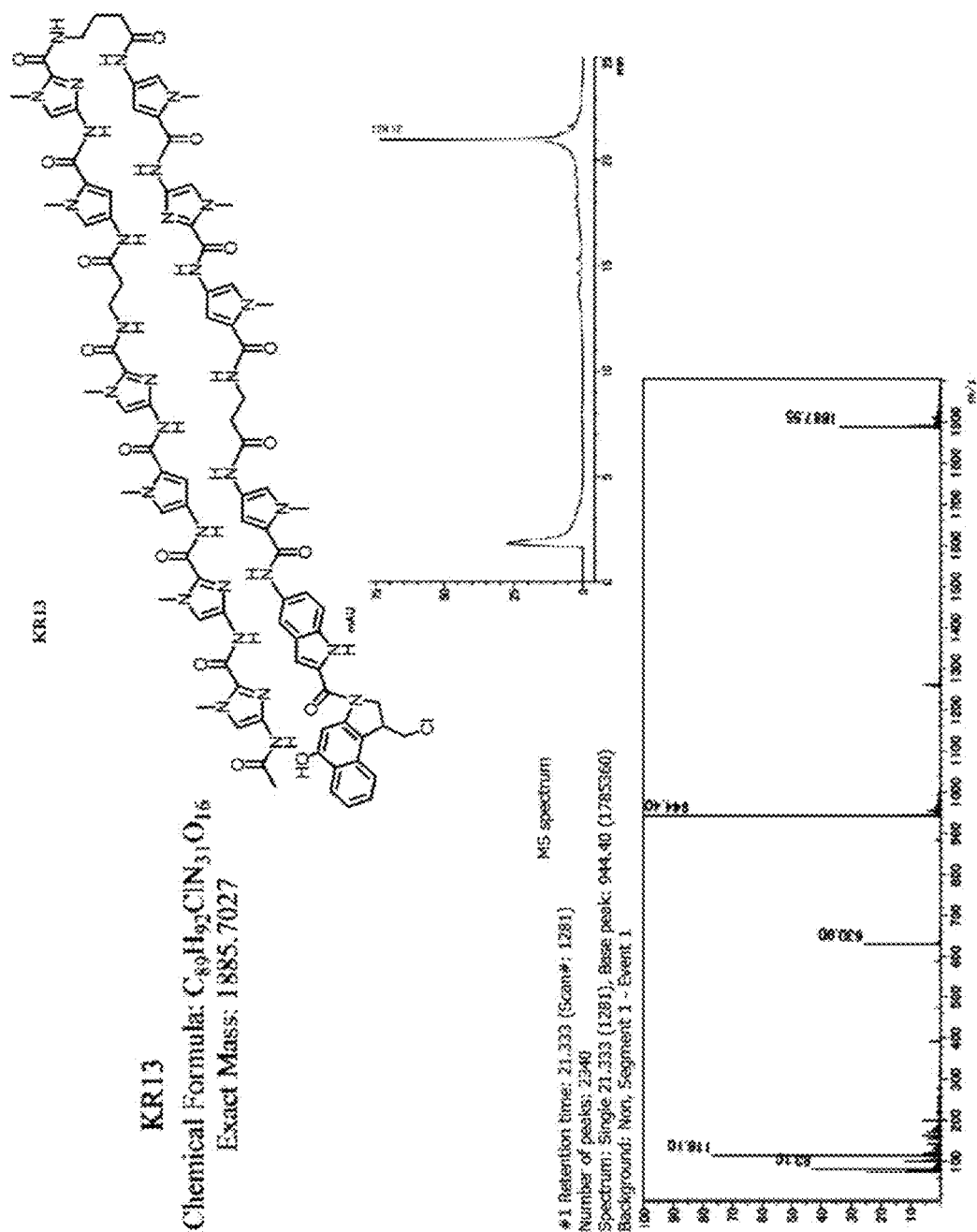
FIG. 4 is a view showing the chromatograms of HPLC and LC-MS, which are related to the synthesis of PIP (KR13) that alkylates the codon 13 mutation of the KRAS gene.
Figure 5:
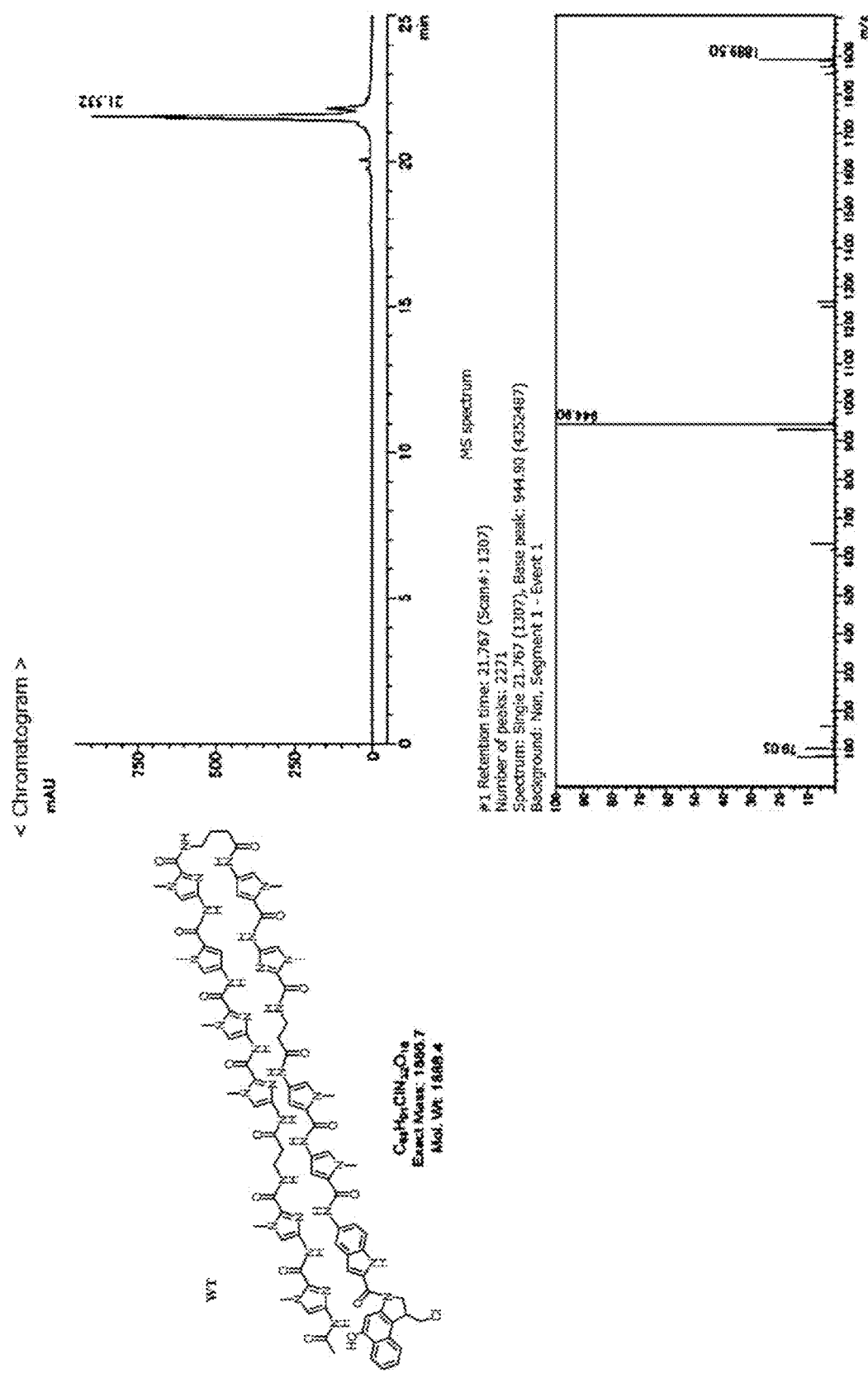
FIG. 5 is a view showing the chromatograms of HPLC and LC-MS, which are related to the synthesis of PIP (WT) recognizing the nucleotide sequence of the wild-type codon 12 of the KRAS gene.
Figure 6:
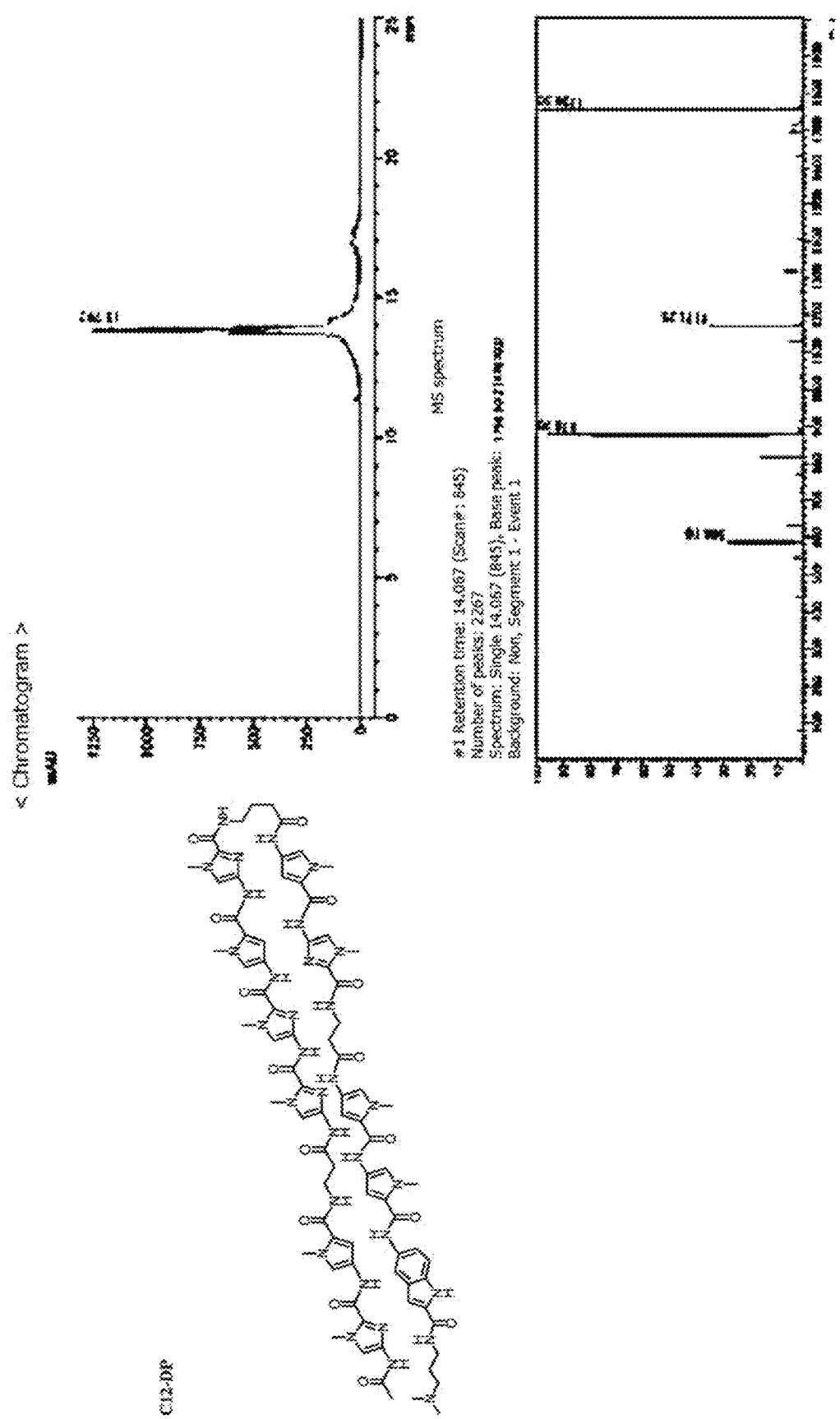
FIG. 6 is a view showing the chromatograms of HPLC and LC-MS, which are related to the synthesis of PIP (C12-Dp), in which a CBI group having an alkylation ability has been removed from KR12.

Moreover, by applying the above-described method, PIP (KR13) represented by a chemical formula 15 as shown below, which alkylates a codon 13 mutation and does not recognize the codon 12 and the wild-type sequence of the KRAS gene, was also synthesized (FIG. 4). Furthermore, as shown in chemical formulae 16 and 17 below, WT recognizing the nucleotide sequence of the wild-type codon 12 of the KRAS gene (FIG. 5), and C12-Dp formed by removing a CBI group having an alkylation ability from KR12 (FIG. 6), were also synthesized.

[Formula 14]

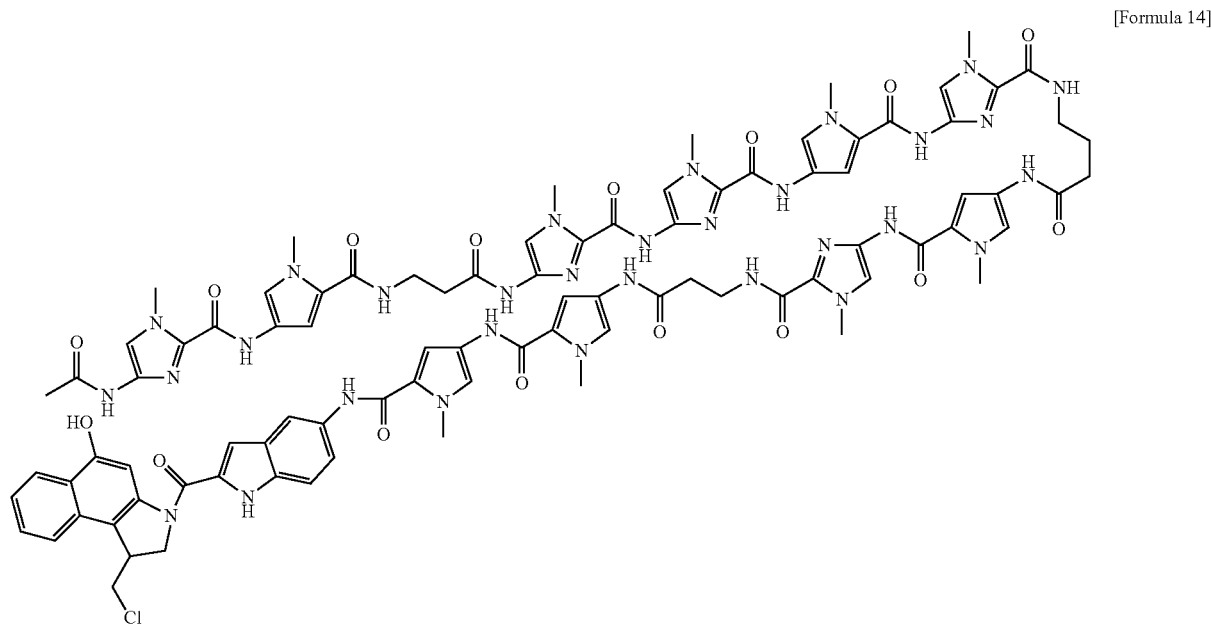

KR12

-continued
[Formula 15]
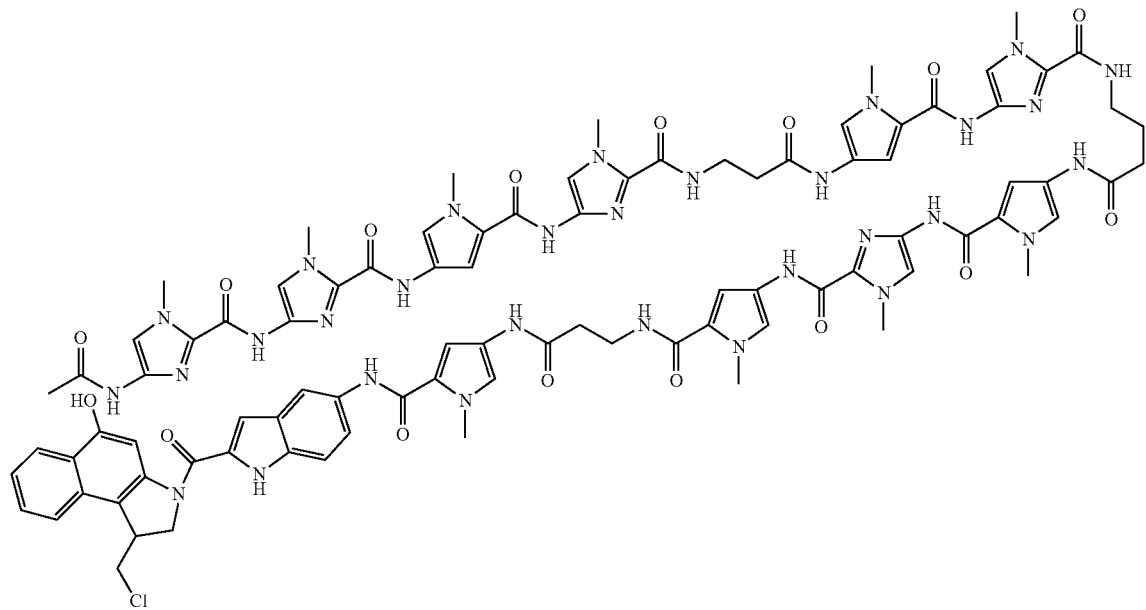
KR13
[Formula 16]
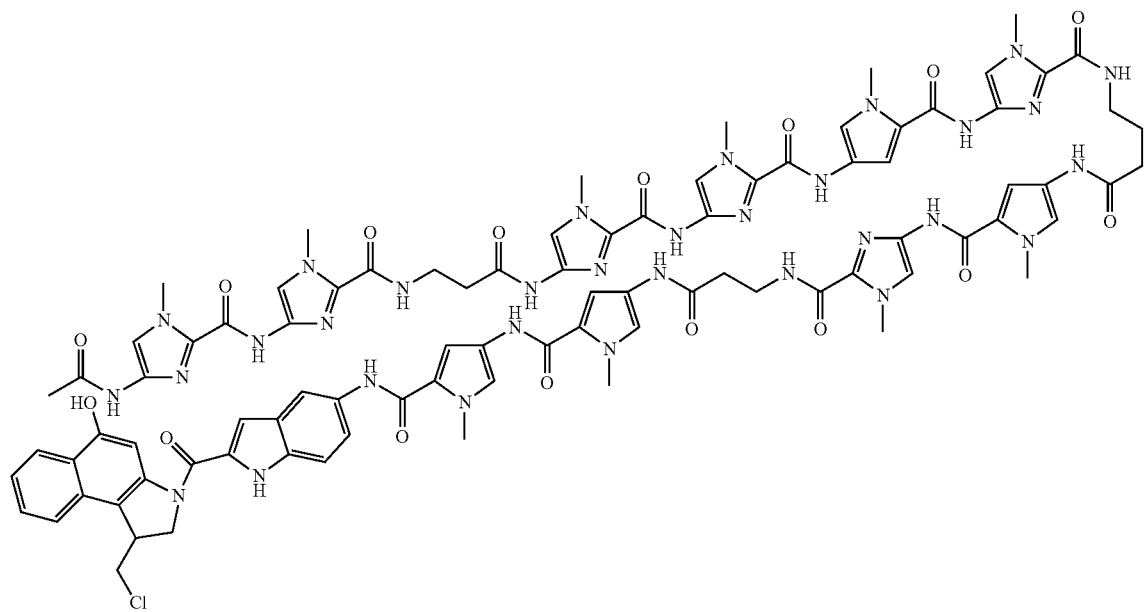
WT

[Formula 17]

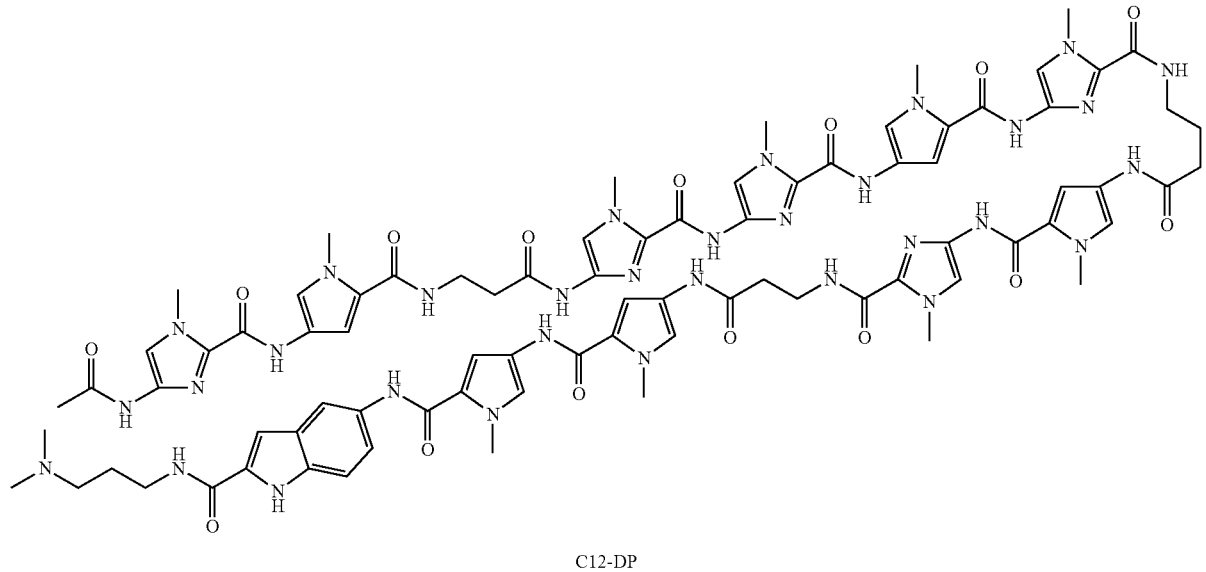

C12-DP

3. Confirmation of Alkylation of Gene Sequence of KRAS Gene Codon 12 Mutation (1) Cloning of Plasmid DNA A 25 µM pair of two fragments (5'-GCCTACGCCATCA-GCGCTGTTGGCGTAGGCA-3' (SEQ ID NO: 1) and 3'-ACGGATGCGGTAGTCGCGACAACCGCATCCG-5' (SEQ ID NO: 2)) (final volume: 50 µL) was annealed to obtain a DNA fragment. The annealed fragment was ligated to a pGEM-T easy vector manufactured by Sigma-Aldrich. Thereafter, *Escherichia coli* (JM109) competent cells manufactured by Promega were transformed with the obtained product, and the resulting cells were then cultured at 37° C. overnight in a plate comprising an LB medium containing 100 µg/mL ampicillin. A transformed white colony of interest was identified by colony direct PCR using a 500 nM primer set (T7: 5'-TAATACGACTCACTATAGG-3' (SEQ ID NO: 3); and sp6: 5'-CATACGATTTAGGTGACAC-TATAG-3' (SEQ ID NO: 4)) and 10 µL of a reaction solution containing 1 U GoTaq® Green Master Mix manufactured by Promega. The following amplification cycle was applied. After the reaction solution had been incubated at 95° C. for 2 minutes, a reaction cycle consisting of 95° C.-30 seconds, 55° C.-30 seconds, and 72° C.-30 seconds was repeated 30 times, and the final elongation reaction was carried out in a reaction cycle of 72° C.-7 minutes. The colony was transferred into 5 mL of an LB medium containing 100 µg/mL ampicillin, and it was then cultured at 37° C. overnight. The introduced plasmid was recovered using GenElute Plasmid miniprep kit manufactured by Sigma-Aldrich.

(2) High Resolution Gel Electrophoresis

A DNA fragment, 213 base pairs in length, the 5'-terminus of which had been labeled with Texas Red, was synthesized using the above-described plasmid and primers (sp6: 5'-A'TTTAGGTGACACTATAG-3' (SEQ ID NO: 5), and T7: 5'-TAATACGACTCACTATAGGG-3' (SEQ ID NO: 6), with 5'-terminus labeled with Texas Red). The obtained DNA fragment, the 5'-terminus of which had been labeled with Texas Red, was purified using PCR-Clean Up Kit manufactured by Sigma, and the concentration was then determined by UV absorption. 10 µL of the reaction solution comprising each type of alkylating PIP (a 10 nM double stranded DNA fragment, the 5'-terminus of which had been labeled with Texas Red, and a 5 mM sodium phosphate buffer (pH 7.0)) was incubated at 23° C. for 17 hours. After completion of the reaction, excessive alkylation PIP was removed using 10 mg/mL calf thymus DNA (1 µL), and DNA at the target alkylation site was then cleaved by heating at 95° C. for 10 minutes. The solvent was removed by vacuum distillation, and 7 µL of loading dye was then added to the residue. The obtained sample was heated at 95° C. for 25 minutes, and then, it was promptly cooled on ice. Thereafter, 1.2 µL of the sample was subjected to electrophoresis on 6% denaturing polyacrylamide gel, using Hitachi 5500-S DNA Sequencer (FIG. 7).

The experimental results are shown in FIG. 7. FIG. 7A shows the results of SW480 cells (colon cancer) with a mutated KRAS sequence, and FIG. 7B shows the results of AsPC-1 cells (pancreatic cancer) with a mutated KRAS sequence. Thus, it was found that KR12 specifically induced concentration-dependent alkylation of the gene sequence of the codon 12 mutation of the KRAS gene in both SW480 cells (G12V) and AsPC-1 cells (G12D).

4. Cytotoxicity Test Performed on Colon Cancer Cells LS180, and Measurement of 50% Inhibitory Concentration (IC50)

Using LS180 colon cell line, the cells were seeded in each well of a 96-well microplate, resulting in a cell density of 3000 to 5000 cells/well, and they were then cultured overnight. On the following day, KR12 recognizing a codon 12 mutation, WT recognizing wild-type KRAS, and C12-Dp having the same structure as that of KR12, to which an alkylating agent had not been added, were each added to the cultured cells in concentrations of 1 nM, 10 nM, 30 nM, 100 nM, 300 nM, and 1 µM, and were then treated for 48 hours. Thereafter, a WST-8 reagent was added to each well, using cell counting kit-8 (DOJINDO), and the obtained mixture was then reacted for 2 hours. After that, the number of cells was counted at a wavelength of 450 nm according to a colorimetric analysis method using a microplate reader. The method of counting the number of cells comprises: 1) obtaining the mean value of the medium alone, 2) subtracting the mean value of the medium from each well, 3) obtaining the mean value of DMSO, 4) dividing the medium-subtracted value by the mean value of DMSO and then multiplying by 100, 5) obtaining the mean value of each treatment group and a standard deviation, and then preparing a graph. The calculation formula of IC50 is the following: IC50=10 (LOG (A/B)×(50−C)/(D−C)+LOG (B)), wherein A: a higher concentration of two concentrations sandwiching 50%, B: a lower concentration of two concentrations sandwiching 50%, C: inhibitory percentage at B, and D: inhibitory percentage at A.

Figure 8:
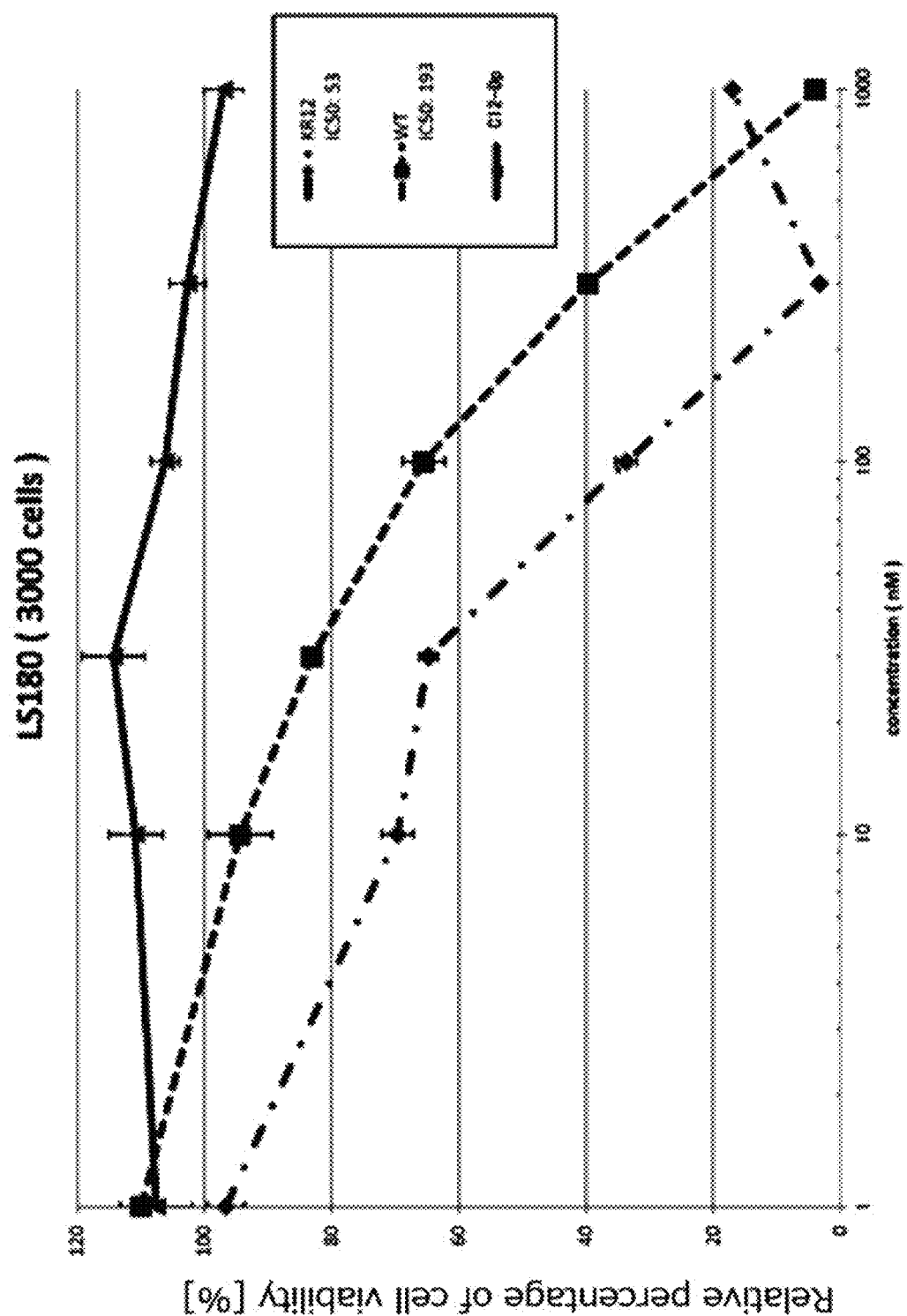
FIG. 8 is a view showing the results obtained by measuring the cell growth of LS180 cells, which have been treated with KR12, WT and non-alkylated C12-DP according to WST assay, and then measuring IC50 (50% inhibitory concentration).

The experimental results are shown in FIG. 8. The IC 50 of the LS180 cells treated with KR12 was the lowest (53 nM), and the IC 50 of the LS180 cells treated with WT was 193 nM. On the other hand, in the case of the LS180 cells treated with C12-Dp that is a PIP compound having the same DNA recognition ability as that of KR12 and does not have an alkylating agent, suppression of the cell growth was not observed.

5. Cytotoxicity Test Performed on Various Cancer Cells, and Measurement of 50% Inhibitory Concentration (IC50)

Using colon cancer and pancreatic cancer cell lines, the cells were seeded in each well of a 96-well microplate, resulting in a cell density of 3000 to 5000 cells/well, and they were then cultured overnight. On the following day, the cells of each type were treated with KR12 recognizing a codon 12 mutation in concentrations of 1 nM, 10 nM, 30 nM, 100 nM, 300 nM, and 1 μM for 48 hours. Thereafter, a WST-8 reagent was added to each well, using cell counting kit-8, and the obtained mixture was then reacted for 2 hours. After that, the number of cells was counted at a wavelength of 450 nm according to a colorimetric analysis method using a microplate reader. The method of counting the number of cells comprises: 1) obtaining the mean value of the medium alone, 2) subtracting the mean value of the medium from each well, 3) obtaining the mean value of DMSO, 4) dividing the medium-subtracted value by the mean value of DMSO and then multiplying by 100, 5) obtaining the mean value of each treatment group and a standard deviation, and then preparing a graph. The calculation formula of IC50 is the following: IC50=10 (LOG (A/B)×(50−C)/(D−C)+LOG (B)), wherein A: a higher concentration of two concentrations sandwiching 50%, B: a lower concentration of two concentrations sandwiching 50%, C: inhibitory percentage at B, and D: inhibitory percentage at A.

The cells used in the aforementioned experiment are human cancer cell lines SW480, SW620, SNU-C2B, LS180, SW1463, DLD-1, HT29, and Caco-2 (purchased from European Collection of Cell Cultures (ECACC)).

Figure 9:
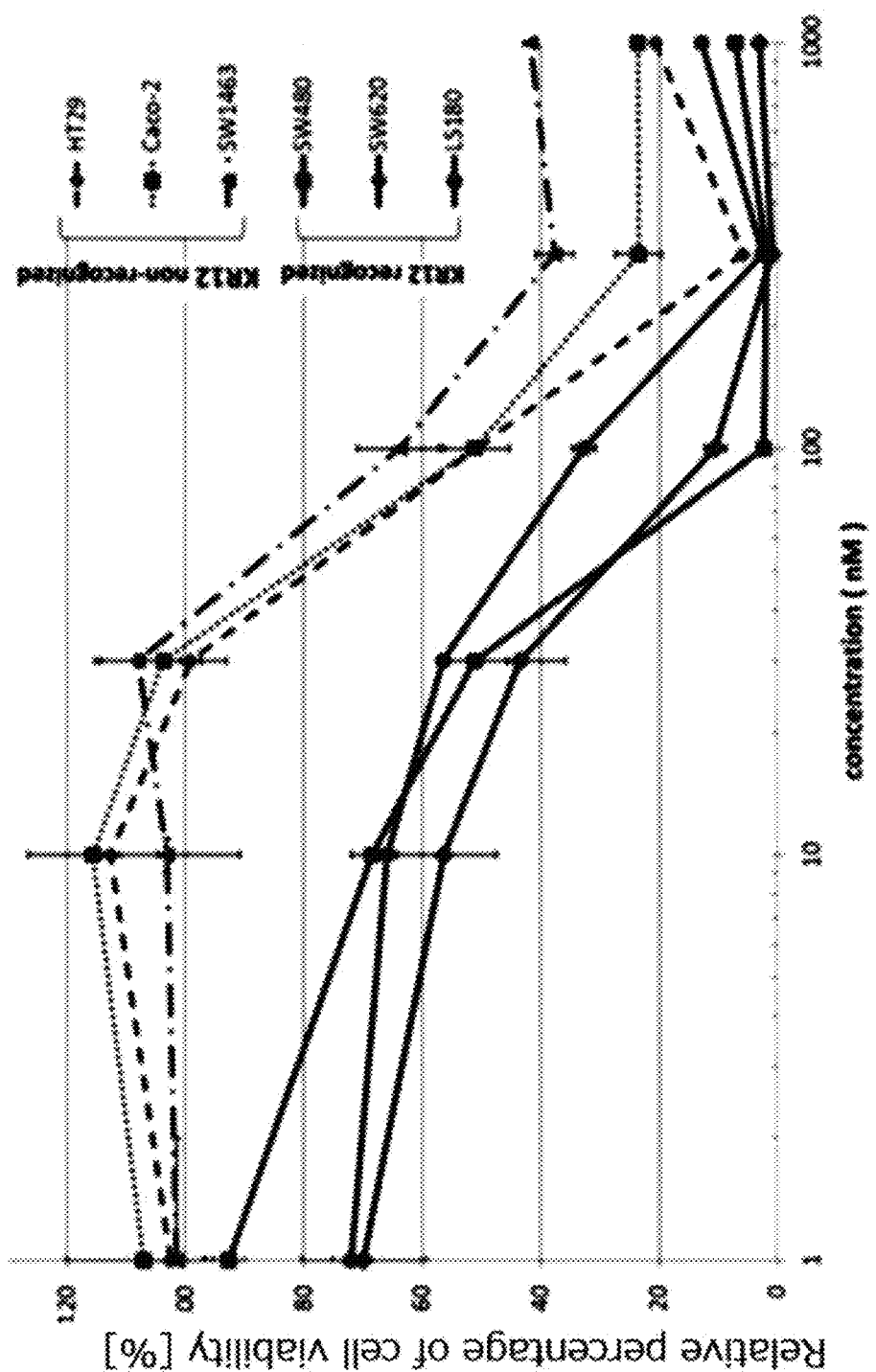
FIG. 9 is a view showing the results obtained by measuring the cell growth of six types of cells after completion of the treatment with KR12 according to WST assay, and then measuring IC50 (50% inhibitory concentration).

The experimental results are shown in Table 1. Regarding IC50 to KR12, SW480, SW620, SNU-C2B, LS180 and HCT116 exhibited low values, whereas SW1463, DLD-1, HT29 and Caco-2 exhibited high values. That is, the cell lines having a codon 12 mutation, which is recognized by KR12, exhibited a low 1050 value of 100 nM or less. SW1463, DLD-1, HT-29 and Caco-2 are all cell lines, which do not have such a codon 12 mutation recognized by KR12, and these cell lines exhibited an IC50 value of 100 nM or more. FIG. 9 is a graph showing the concentration-dependent cell growth-suppressing effects of the cell lines HT29, Caco-2 and SW1463, not having a codon 12 mutation recognized by KR12, and the cell lines SW480, SW620 and LS180 having such a mutation.

TABLE 1

| Cell | KRAS status | KRAS (glycine) | codon 12 (GGT) | codon 13 (GGC) | KRAS allele | KR12 IC$_{50}$ (nM) |
|---|---|---|---|---|---|---|
| SW480 | Mutant | G12V | GTT | GGC | Homo | 31 |
| SW620 | Mutant | G12V | GTT | GGC | Homo | 17 |
| SNU-C2B | Mutant | G12D | GAT | GGC | Hetero | 57 |
| LS180 | Mutant | G12D | GAT | GGC | Hetero | 42 |
| PANC-1 | Mutant | G12D | GAT | GGC | Hetero | 81 |
| K375 | Mutant | G12D | GAT | | Hetero | 78 |
| SW1463 | Mutant | G12C | TGT | GGC | Homo | 178 |
| DLD-1 | Mutant | G13D | GGT | GAC | Hetero | 153 |
| HT-29 | Wild type | WT | GGT | GGC | | 102 |
| Caco-2 | Wild type | WT | GGT | GGC | | 105 |

6-1. Analysis of Change in Cell Cycle

In order to observe a cell cycle, treated cells and untreated cells were each washed with DNase-free PBS twice, and were then immobilized with 70% ethanol (frozen). The immobilized cells were treated with PBS containing 10 g/mL RNaseA and 50 g/mL propidium iodide, while they were left in a dark place at room temperature for 30 minutes. Using an FL-2H filter of FACS Calibur flowcytometer (Becton Dickinson, USA), fluorescence intensity was measured. The rate of cell cycle was determined by analyzing the obtained data using Cell Quest software (Becton Dickinson, USA). Regarding the treatment of cells, LS180 was treated with 50 nM KR12 or KR13 (dissolved in 0.125% DMSO) for 72 hours, and as a long-term treatment experiment, a culture experiment was carried out for 14 days. As a control, the cells were cultured in an MEM medium containing 10% FBS and 0.125% DMSO for 14 days.

Figure 10:
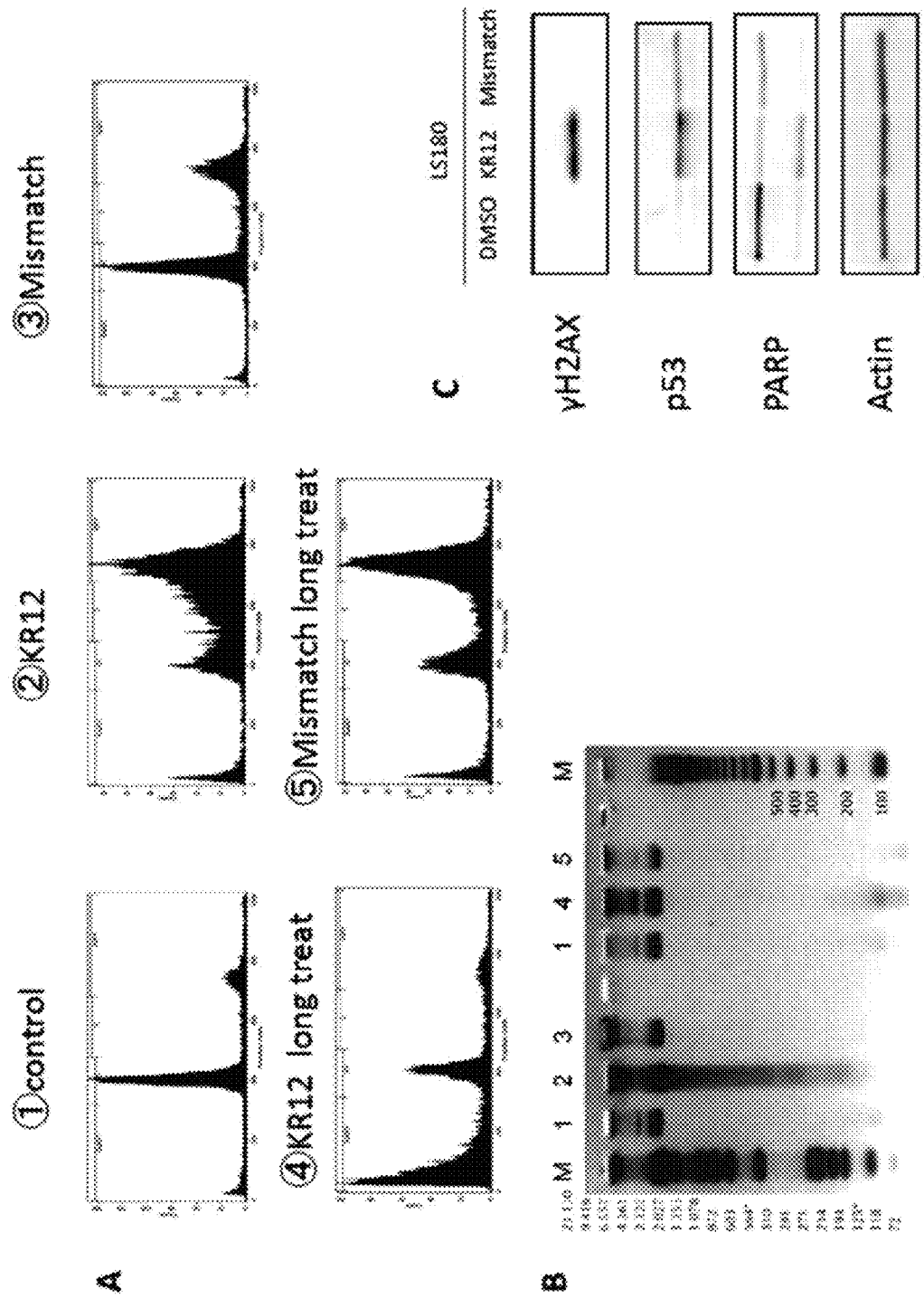
FIG. 10 is a view showing the results obtained by performing a change in the cell cycle of KR12-treated cancer cells, confirmation of a DNA ladder caused by induction of cell death, cell damage, and the protein analysis of a marker of apoptosis.

The experimental results are shown in FIG. 10A. When the LS180 cells were treated with 50 nM KR12, the LS180 cells at the S stage were increased. When the LS180 cells were treated with KR12 for long period of time, the cells at the Sub G1 stage were significantly increased. The S stage and the G2M stage indicate termination of the cell cycle, and the Sub G1 stage indicates cell death. Accordingly, it was found that KR12 induces LS180 cells to termination of the cell cycle, and then to the cell death, as the concentration of the KR12 is increased. In a case where the LS180 cells were treated with KR13 that does not recognize a codon 12 mutation (Mismatch), the cells at the S phase and the G2M phase were slightly increased. However, an increase in the cell at the Sub G1 phase was not significant, even when the cells were treated with KR13 for a long period of time.

6-2. Confirmation of Cell Death (Apoptosis) by Fragmentation of DNA

Regarding the treatment of cells, the LS180 cells were cultured at a cell density of $1.0 \times 10^5$ cells/30 mm dish in a culture media of MEM (gibco)+10% FBS (gibco)+100 units/ml Penicillin+100 μg/ml Streptmycin (gibco). Thereafter, the cultured cells were treated with 50 nM KR12 or KR13 (dissolved in 0.125% DMSO) for 72 hours, and also, as a long-term experiment, the cells were treated with KR 12 or KR13 for 14 days. Thereafter, the cells of different groups were treated with a control MEM medium containing 10% FBS and 0.125% DMSO for 11 days. At the same time, as a control group, the LS180 cells were treated with 10% FBS and 0.125% DMSO for 14 days. Thereafter, the cells of the different groups were treated with trypsin, and were then recovered. The recovered cells were stirred in 50 µl of a PBS solution, and 3 µl of 1.5% Triton X (in water) and 3 µl of an RNase (1 mg/ml in water) were then added to the reaction solution. The mixed solution was treated at 37° C. for 30 minutes. Subsequently, 3 µl of proteinase K (1 mg/ml) was added to the reaction solution, and the obtained mixture was then treated at 37° C. for 30 minutes. Subsequently, 12 µl of 6× loading buffer was further added to the reaction solution, and the obtained mixture was treated at 65° C. for 10 minutes. Immediately after the treatment, 20 µl of the reaction solution was electrophoresed on 2% agarose gel in TBE at 100 V, and the gel was then stained with ethidium.

The experimental results are shown in FIG. 10B. In the case of the long-term treatment, DNA fragmentation was not observed in a control group (lane 1) and a KR13-treated group (lane 3). However, in a KR12-treated group (lane 2), DNA fragmentation induced by cell death was observed. In the 72-hour-treated groups, DNA fragmentation was not observed in both groups treated with KR12 and KR13 (lanes 4 and 5). These results suggest that cell death (apoptosis) in the LS180 cells would be induced by a short-term treatment with KR12, but that such cell death would not be induced by long-term and short term treatments with KR13.

6-3. Studies of Markers Inducing DNA Damage and Repair and Cell Death (Apoptosis) by Western Analysis LS180 cells, which had been subjected to a long-term treatment experiment and had been treated with 50 nM KR12 or KR13 (dissolved in 0.125% DMSO) for 14 days, were dissolved in a 1×SDS-sample buffer. The obtained solution was treated at 100° C. for 5 minutes. The protein amount was estimated using Bradford reagent (Bio-Rad, CA), and was then electrophoresed by 10% SDS-PAGE. After that, the protein was transferred onto polyvinylidene difluoride membranes (Millipore, Mass.), and using 5% dry milk in Tris-buffered saline (TBS) plus 0.1% Tween 20 as a blocking agent, anti-γH2AX (2F3, BioLegend, CA), anti-p53 (DO-1, Santa Cruz Biotechnology, CA), anti-PARP (Cell Signaling Technologies, MA), or anti-actin antibody (20-33, Sigma, MO) was added to lanes, and the protein was further treated with HRP-conjugated anti-mouse IgG or anti-rabbit IgG (Cell Signaling Technologies, MA). Before the treatment with a secondary antibody, the primary antibody was washed, as appropriate. Thereafter, the protein was washed with TBS plus 0.1% Tween 20, and it was then identified by electrogenerated chemiluminescence (ECL) (Amersham Biosciences, NJ).

The experimental results are shown in FIG. 10C. A DNA damage marker, γH2AX, was induced by a long-term treatment with KR12, and induction of p53 was also observed. Further, since the cleavage of the PARP protein was observed, it was found that cell death (apoptosis) was induced. On the other hand, significant induction of DNA damage and cell death was not observed in the cases of the treatments with the control and KR13. The actin band for the protein was seen. These results suggest that DNA damage would be induced to the colon cancer cell line by the long-term treatment with KR12 and cell death would also be induced.

7. Semi-Quantitative Analysis of Gene Expression by RT-PCR

HT29 and LS180 were each cultured in a 12-well plate. On the following day, the cells were treated with 50 nM KR12 or KR13, and were then cultured for 48 hours. Thereafter, the cultured cells were harvested, and RNA was then extracted. For the extraction, RT-PCR was carried out using RNeasy mini kit (Qiagen, CA). Subsequently, using the extracted RNA as a template, cDNA for reverse transcription was prepared by employing Super Script VILO cDNA Synthesis Kit (Invitrogen, CA). Using the prepared cDNA as a template, PCR was carried out. After a reaction had been carried out at 94° C. for 5 minutes, a reaction cycle of 94° C.-30 seconds, 55° C.-30 seconds, and 72° C.-30 seconds was repeated 20 times. Finally, an elongation reaction was carried out at 72° C. for 7 minutes. The PCR product was subjected to electrophoresis on 2% agarose gel. The amount of the PCR product was calculated using a photograph of a band stained with ethidium bromide.

The below-mentioned primer set was used in PCR.

A forward primer (sense) and a reverse primer (antisense), which amplify both mutant and wild-type KRAS genes, and a forward primer (sense) and a reverse primer (antisense) for an RPS18 (ribosomal protein S18) gene used as an internal standard are shown below.

```
KRAS gene
Forward primer (sense):
5'-GGAGAGAGGCCTGCTGAA-3'         (SEQ ID NO: 7)

Reverse primer (antisense):
5'-TGACCTGCTGTGTCGAGAAT-3'       (SEQ ID NO: 8)

RPS18 (internal standard)
Forward primer (sense):
5'-GAGGATGAGGTGGAACGTGT-3'       (SEQ ID NO: 9)

Reverse primer (antisense):
5'-TCTTCAGTCGCTCCAGGTCT-3'       (SEQ ID NO: 10)
```

Figure 11:
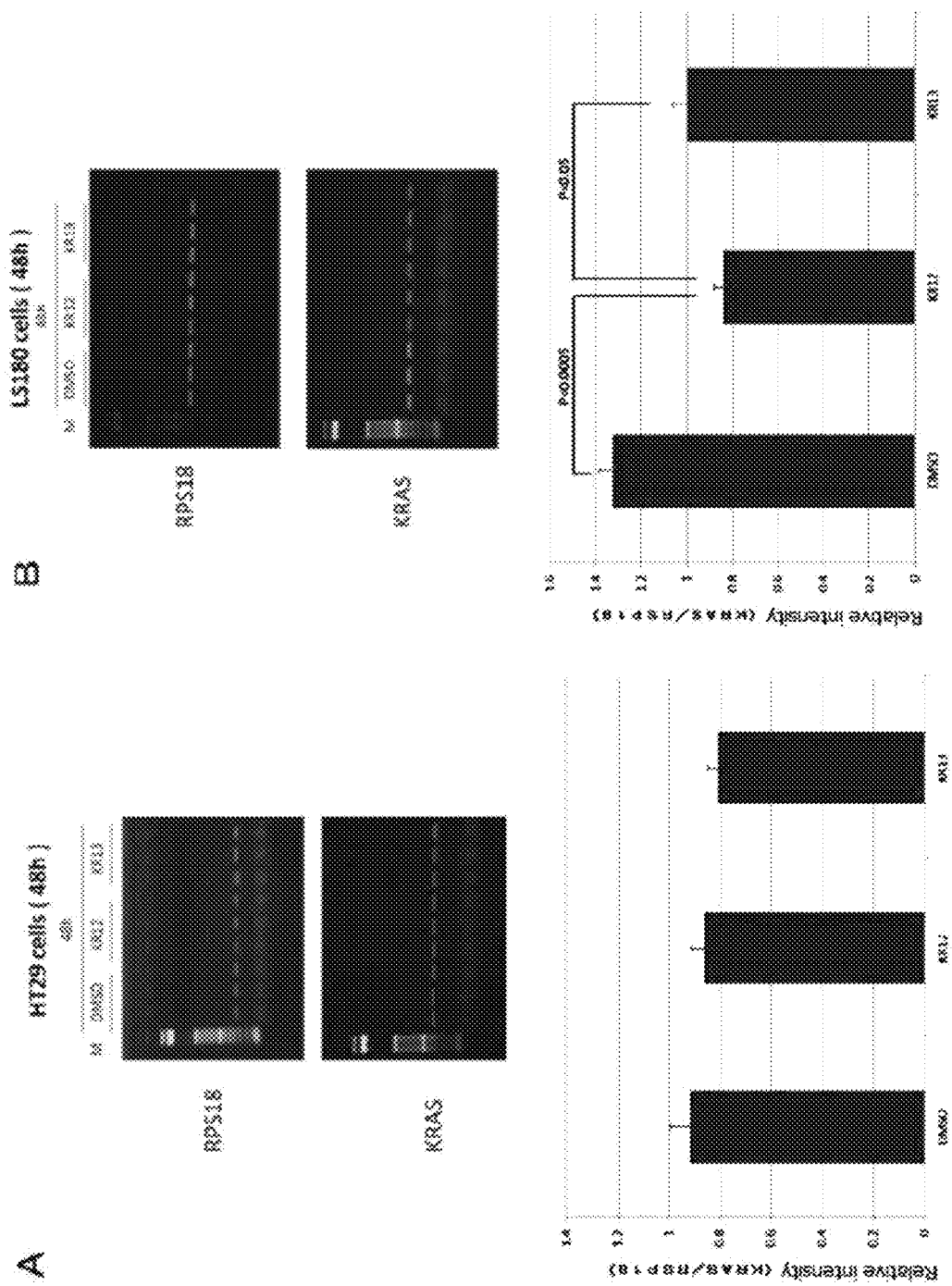
FIG. 11 is a view showing the semi-quantitative analysis of relative KRAS gene expression of KR12-treated cancer cells (RT-PCR).

The experimental results are shown in FIG. 11. In the case of HT29 (a wild type having no KRAS gene codon 12 mutations), the expression of the KRAS gene was not changed by KR12 (FIG. 11A). On the other hand, in the case of LS180 (having a KRAS gene codon 12 mutation), the expression of the KRAS gene was significantly suppressed by administration of KR12 (FIG. 11B).

8. Colony Sequence

The cells ($6.5×10^4$) were seeded and were then cultured overnight. Thereafter, the cultured cells were treated with 50 nM KR12 or KR13, and were then cultured for 48 hours. After that, the cultured cells were harvested, and RNA was then extracted. For the extraction, RT-PCT was carried out using RNeasy mini kit (Qiagen, CA). Subsequently, using the extracted RNA as a template, cDNA for reverse transcription was prepared by employing Super Script VILO cDNA Synthesis Kit (Invitrogen, CA). Using the prepared cDNA as a template, PCR was carried out using the primers shown in SEQ ID NO: 7 and SEQ ID NO: 8. After a reaction had been carried out at 94° C. for 5 minutes, a reaction cycle of 94° C.—30 seconds, 55° C.—30 seconds, and 72° C.—30 seconds was repeated 20 times. Finally, an elongation reaction was carried out at 72° C. for 7 minutes. The PCR product was cloned using pGEM-T Easy vector (Promega, Wis.). Thereafter, *Escherichia coli* DH5a competent cells (Toyobo, Japan) were transformed with the clone, and the obtained transformant was then cultured at 37° C. overnight in an LB plate containing 50 μg/mL ampicillin, 1 mg of X-gal and 1 mg of isopropyl-β-thiogalactopyranoside. White colonies were identified by colony direct PCR. Regarding the PCR reaction cycle, after a reaction had been carried out at 94° C. for 5 minutes, a reaction cycle of 94° C.—30 seconds, 55° C.—30 seconds, and 72° C.—30 seconds was repeated 30 times. Finally, an elongation reaction was carried out at 72° C. for 7 minutes. The following primer set, namely, an M13-F1 primer and an M13-R1 primer were used for amplification. The sequence of the amplified DNA was decoded using a sequencing primer KRAS-2R, and the KRAS gene mutation site in each colony was then identified.

```
M13-F1 primer:
5'-CGCCAGGGTTTTCCCAGTCACGAC-3'  (SEQ ID NO: 11)

M13-R1 primer:
5'-GGAAACAGCTATGACCATGATTAC-3'  (SEQ ID NO: 12)

Sequencing primer KRAS-2R:
5'-TGACCTGCTGTGTCGAGAAT-3'      (SEQ ID NO: 13)
```

9. Colony PCR

Using primers that specifically amplify the GAT mutant gene of KRAS codon 12 (KRAS-MUT-F and KRAS-MUT-R) and the wild-type genes thereof (KRAS-WT-F and KRAS-WT-R), PCR was carried out directly on the *Escherichia coli* cells in the above-described white colonies. Whether each colony was a mutant KRAS gene or a wild-type KRAS gene was determined, depending on by which primer set the band of interest was amplified.

```
Allele specific primers (recognizing GAT mutation)
KRAS-WT-F:
5'-CTTGTGGTAGTTGGAGCTCG-3'      (SEQ ID NO: 14)

KRAS-WT-R:
5'-TCCAAGAGACAGGTTTCTCCA-3'     (SEQ ID NO: 15)

KRAS-MUT-F:
5'-CTTGTGGTAGTTGGAGCTCA-3'      (SEQ ID NO: 16)

KRAS-MUT-R:
5'-CATGTACTGGTCCCTCATTGC-3'     (SEQ ID NO: 17)
```

The experimental results are shown in Tables 2-4. KR12, which was considered to specifically alkylate the KRAS mutant codon 12 gene, was administered to a heterozygous colon cancer cell line LS180 having both a mutant codon 12 KRAS gene and a wild-type KRAS gene. Forty-eight hours later, RNA was extracted, and the KRAS gene was then quantitatively amplified. The amplified gene was cloned into a plasmid, using a TA cloning kit, and the obtained plasmid was then introduced into competent cells. Thereafter, by performing blue-white selection using an LB/amp/IPTG/X-Gal plate, white colonies having inserts were picked up, and then, the presence or absence of a colon 12 mutation in each colony was examined by direct sequencing or by a colony PCR method. It was found by the colony sequence method that, in the case of LS180 cells, mutant genes and wild-type genes were equally amplified in DMSO by administration of KR12, but that the number of mutant gene colonies was a half of the number of wild-type gene colonies in the KR12 administration group, and the number of mutant genes was rather increased in the KR13 administration group (Table 2). Likewise, it was confirmed also by the colony PCR that the expression levels of mutant cancer genes were decreased by administration of KR12 (Table 3). Likewise, in the case of a heterozygous pancreatic cancer cell line PANC-1 as well, as shown in Table 4, the mutant KRAS genes were expressed 3-fold higher than the wild-type KRAS genes in the control group, but the expression levels of the mutant KRAS genes were decreased to the same levels of the wild-type KRAS genes by administration of KR12. It can be said that these results demonstrate that KR12 significantly suppresses the expression of mutant KRAS genes in cell lines having a heterozygous mutation in the codon 12 of the KRAS gene.

TABLE 2

|      | WT | MUT |
|------|----|-----|
| DMSO | 19 | 19  |
| KR12 | 29 | 14  |
| KR13 | 15 | 22  |

TABLE 3

|      | WT | MUT |
|------|----|-----|
| DMSO | 16 | 11  |
| KR12 | 27 | 11  |
| KR13 | 14 | 13  |

TABLE 4

|      | WT | MUT |
|------|----|-----|
| DMSO | 13 | 33  |
| KR12 | 21 | 24  |
| KR13 | 8  | 18  |

10. Measurement of RAS Activity

Cells (the number of cells: 2×10$^6$ cells/100 mm plate or 1×10$^6$ cells/100 mm plate) were cultured in a complete nutrient medium, and on the following day, the cultured cells were treated with 50 nM KR12 or KR13, followed by culture for 48 hours. Thereafter, the resulting cells were dissolved in a magnesium lysis buffer (MLB), and a RAS activity level was then measured using a RAS activation assay kit (Millipore, Mass.).

Figure 12:
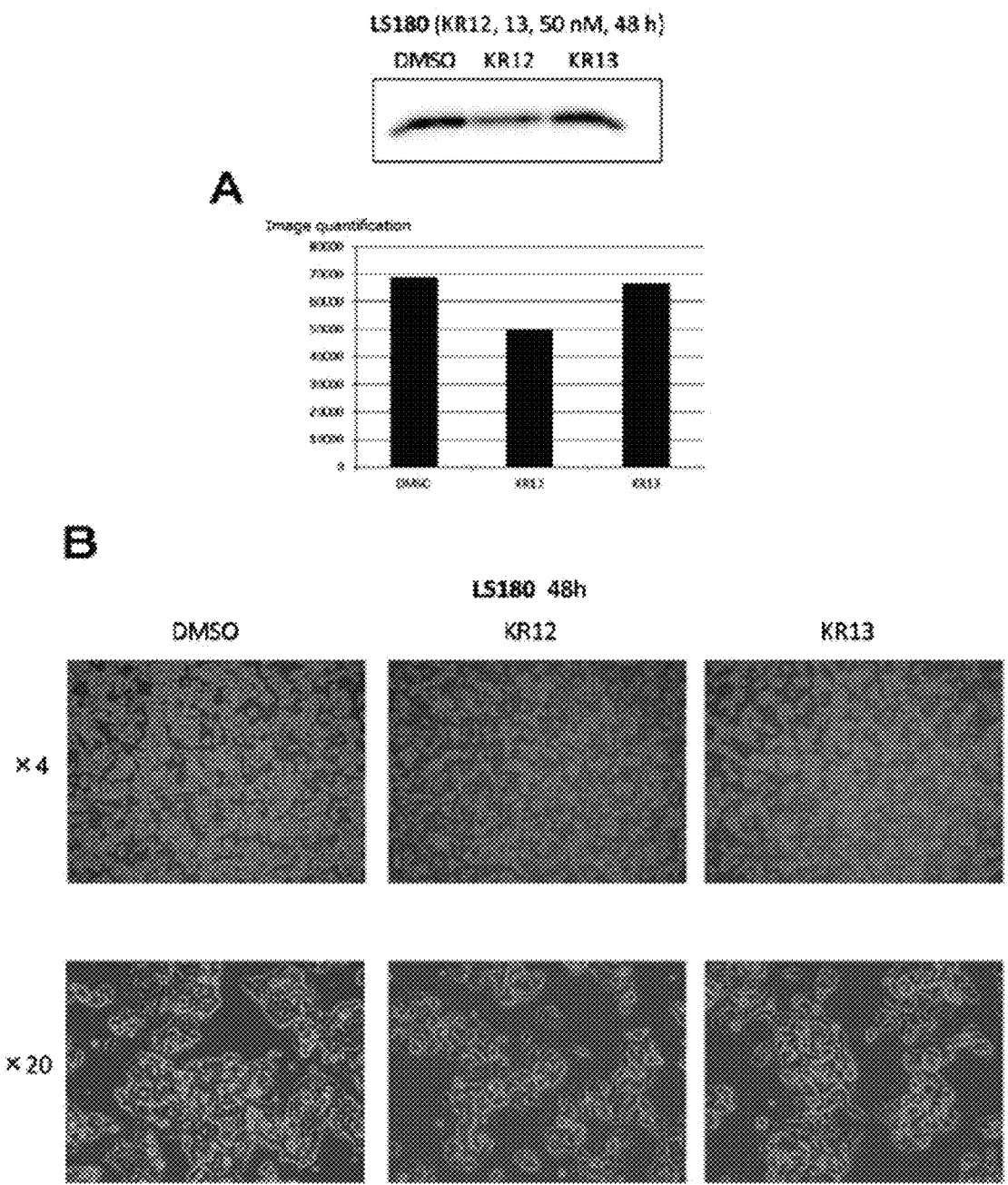
FIG. 12 is a view showing the results of the measurement of RAS activity of KR12-treated LS180 cells.
Figure 13:
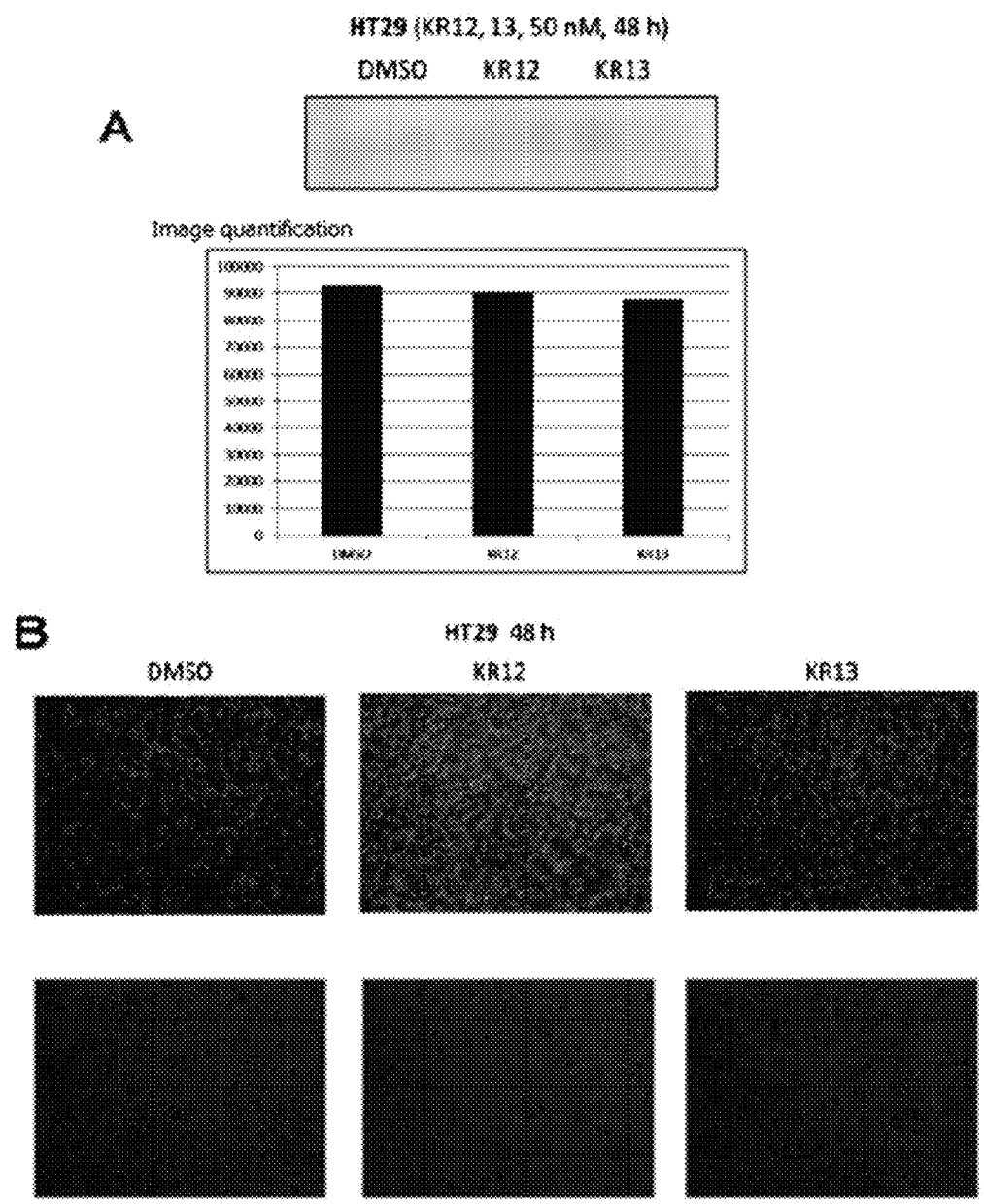
FIG. 13 is a view showing the results of the measurement of RAS activity of KR12-treated HT29 cells.

The experimental results are shown in FIG. 12 and FIG. 13. In HT29 (a wild-type cell line having no mutations in KRAS gene codon 12), active-type KRAS proteins (p21-ras proteins) could be hardly detected (FIG. 13A). On the other hand, in LS180 (with a KRAS gene codon 12 mutation), active-type KRAS proteins could be detected (FIG. 12A). Moreover, the activity of the detected KRAS protein was decreased by KR12 (FIG. 12A), and the cell growth was also suppressed by KR12 (FIG. 12B). It is considered that these results demonstrate that active-type KRAS proteins were constantly expressed by the codon 12 mutation of the KRAS gene in the LS180 cells, but that the expression of the mutant gene was suppressed by administration of KR12, the active-type KRAS proteins were thereby decreased, and induction of the cell death was thereby promoted.

11. Experiment for Evaluating Suppression of Tumor Growth by KR12 in Nude Mice, into which HT29, SW480 or LS180 had been Transplanted The below-mentioned 3 types of PBS solutions containing each type of cells were subcutaneously transplanted into the femurs of nude mice (i.e., HT29 into 7 mice, LS180 into 7 mice, and SW480 into 6 mice), and thereafter, at a time point in which a tumor adhered to the living body of each mouse and the tumor volume became approximately 100 mm$^3$, a drug was prepared with a composition of 3.4 mmol KR12 (1.36 mM KR12 dissolved in 2.5 µL of DMSO and 197.5 µL of PBS), or of a DMSO/PBS control (2.5 µL of DMSO and 197.5 µL of PBS). The prepared drug was subjected to sonication for 10 minutes, and 200 µL of the drug was administered to each mouse via the caudal vein thereof. The body weight and the tumor size were measured once three days, and the size of the tumor was measured by the method of 0.52×L×W×D (⅙×π× L× W× D).

The details of the cell lines transplanted into nude mice are as follows. HT29 (KRAS-WT): (transplanted in an amount of 2×10$^6$ cells/100 µl PBS into the subcutis of each mouse; a wild-type KRAS codon 12 cell line having no codon 12 mutations)
SW480 (KRAS-MUThomo): (transplanted in an amount of 5×10$^6$ cells/100 µl PBS into the subcutis of each mouse; a cell line having a heterozygous KRAS gene codon 12 mutation G12V)
LS180 (KRAS-MUThetero): (transplanted in an amount of 3×10$^6$ cells/100 µl PBS into the subcutis of each mouse; a cell line having a heterozygous KRAS gene codon 12 mutation G12D)

Figure 14:
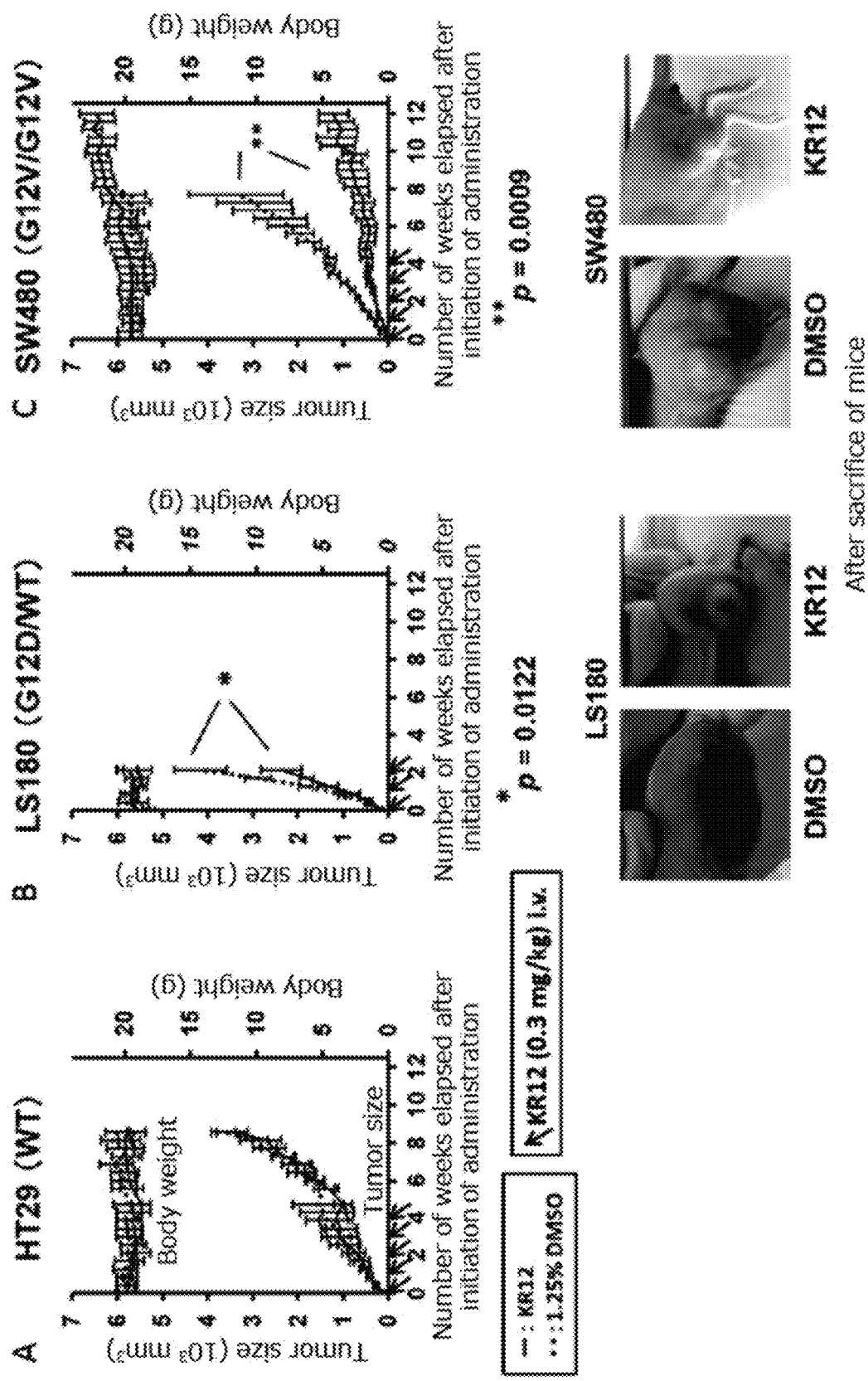
FIG. 14 is a view showing the results of an experiment for evaluating tumor growth suppression, using nude mice.

The experimental results are shown in FIG. 14. As a result, the tumor growth in nude mice, into which HT29 cells having no codon 12 mutations had been transplanted, could not be suppressed by administration of KR12 (FIG. 14A), but the tumor size in nude mice, into which SW480 cells having a homozygous codon 12 mutation had been transplanted, was significantly reduced by administration of KR12 (FIG. 14C). Also, the tumor growth in nude mice, into which LS180 cells heterozygously having a KR12 mutant allele and a wild-type allele had been transplanted, was significantly suppressed by administration of KR12 (FIG. 14B). When the DMSO/PBS control was administered to nude mice, into which SW480 cells had been transplanted, the size of tumor was continuously enlarged. However, if KR12 was administered to the mice, the size of the tumor was significantly reduced 2 months after the administration, and the tumor became an extremely small and hard induration 3 months after the administration (FIGS. 14A-C, photographs taken upon autopsy (3 months later, or at the time in which the tumor had a diameter of 2 cm or more)).

Figure 15:
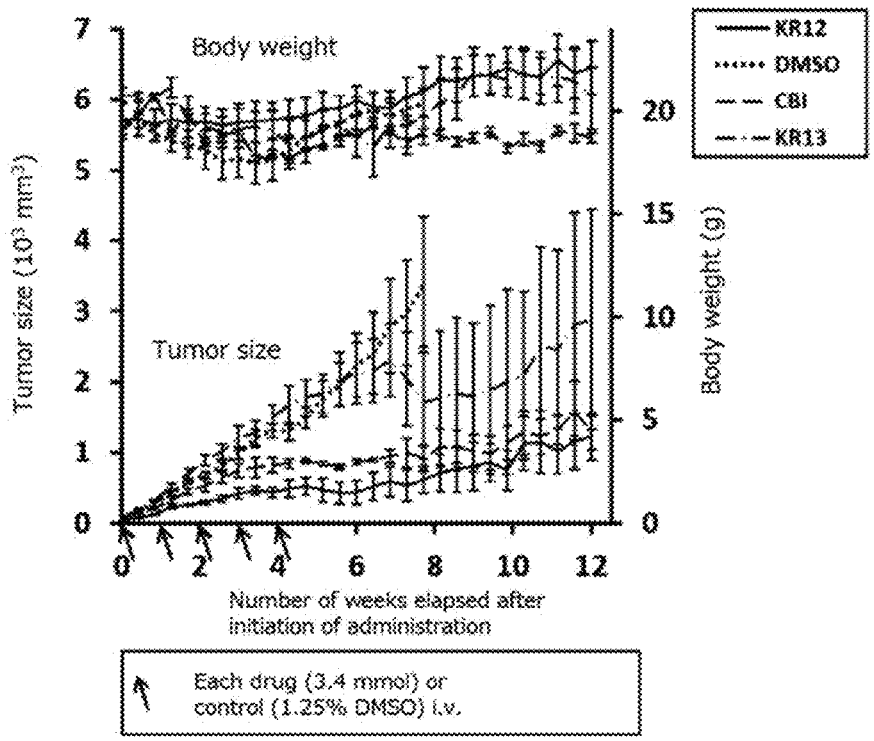
FIG. 15 is a view showing the results of a comparative experiment regarding CBI administration and KR13 administration and an experiment for evaluating tumor growth suppression by a single administration, in which nude mice have been used.
Figure 15:
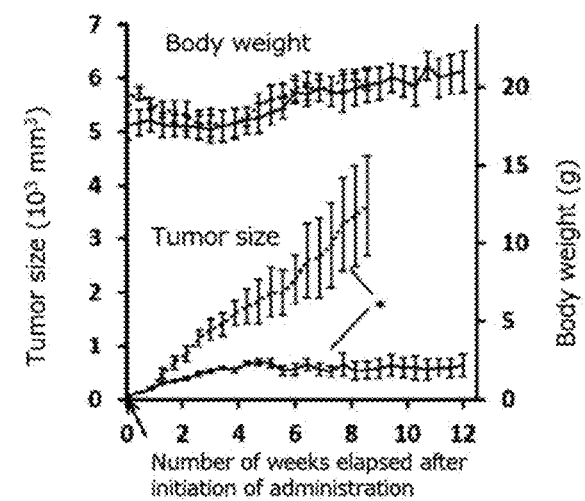
Figure 15:
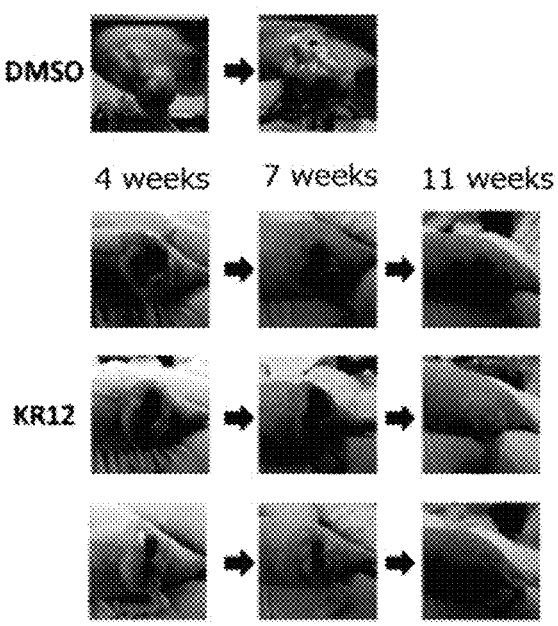

Using, as controls, PIP-indole-seco-CBI (KR13) not recognizing a codon 12 mutation and 8.4 mmol seco CBI (3.36 mM CBI dissolved in 2.5 µL of DMSO and 197.5 µL of PBS), instead of the DMSO/PBS control, an experiment was carried out by the same method as that of the above section 11. The results are shown in FIG. 15. KR12 exhibited a cancer tumor-inhibitory effect on nude mice into which SW480 cells had been transplanted, wherein the cancer tumor-inhibitory effect was significantly higher than in the case of administration of KR13. Moreover, the tendency of body weight reduction, which was observed in the case of administration of seco-CBI, was not observed in the cases of administration of KR12 and KR13. That is to say, these results demonstrate that KR12 enables tumor growth suppression, which is impossible for KR13 not recognizing a G12D mutation sequence, and that KR12 does not cause side effects such as body weight reduction or abnormal health condition. Furthermore, rough hair coat, stop eating, less active, abnormal behavior and the like were not found in nude mice, to which KR12 had been administered.

12. Analysis of Cellular Localization

Into the N-terminus of C12DP, β alanine was introduced, and then, the coupling of FITC was carried out. The coupling of FITC was carried out by passing 4-fold excessive fluorescein (0.40 mmol), DIEA and HCTU, which had been dissolved in DMF, through a column, and then stirring it for 60 minutes. LS180 cells were cultured in a culture media of MEM (gibco)+10% FBS (gibco)+100 units/ml Penicillin+ 100 g/ml Streptmycin (gibco). When the cells became approximately 50% confluent, FITC-labeled KR12 (1 µmol) was added thereto, and two hours later, the cells were mounted in VECTASHIELD (VECTOR). Nuclear staining was carried out using DAPI, and the resultant was then observed under a confocal microscope (Leica, TCS-SPE).

Figure 16:
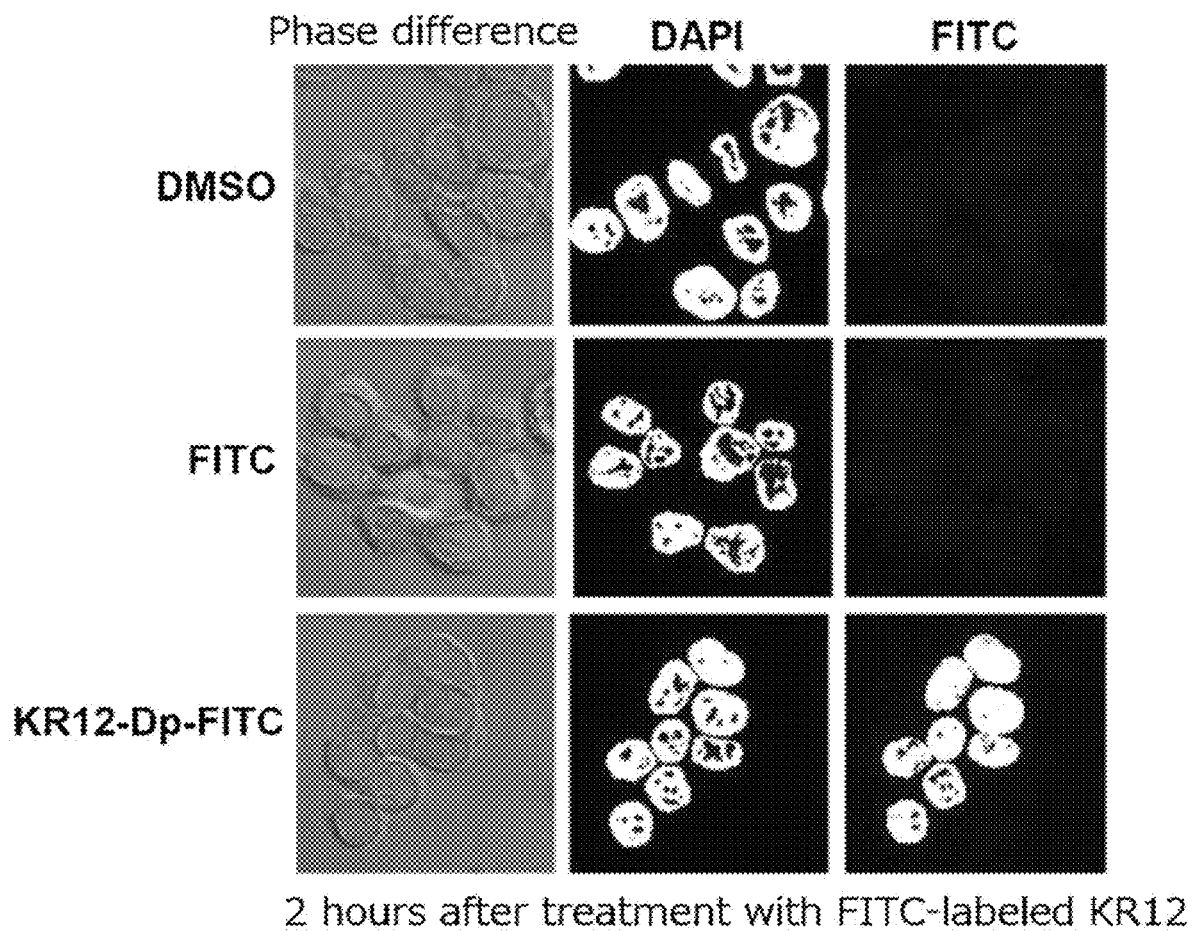
FIG. 16 is a view showing intracellular localization of KR12 in LS180 cells.

The experimental results are shown in FIG. 16. Two hours after the administration of the FITC-labeled KR12 (1 µmol) into the culture medium of LS180 cells, the resulting cells were observed. As a result, fluorescence was accumulated in the nucleus of the LS180 cells, and thus, it was confirmed that KR12 moved into the nucleus of the cultured colon cancer cells, and was localized therein.

13. Test Regarding Targeting Ability to Cancer Stem Cells

An experiment was carried out using two types of colon cancer cell lines SW480 cells and LoVo cells. The cells of each type (2×10$^5$ cells) were cultured in a sphere forming medium (SFM, which was a culture media prepared by adding B27 (Miltenyi, 2%), EGF (20 ng/mL) and FGF2 (20 ng/mL) to a DMEM/Ham's F-12 culture media). On the 4th day, FITC-labeled KR12 (1 µmol) or doxisorbicin (1 µmol) was added to the culture, and one hour later, the reaction mixture was washed with PBS twice. The resultant was cultured again in SEM, and the obtained culture was mounted at 0, 4, and 24 hours after initiation of the culture (Invitrogen: ProLong® Gold Antifade Reagent (With DAPI)). The resultant was observed under a confocal microscope (Leica, TCS-SPE).

Figure 17:
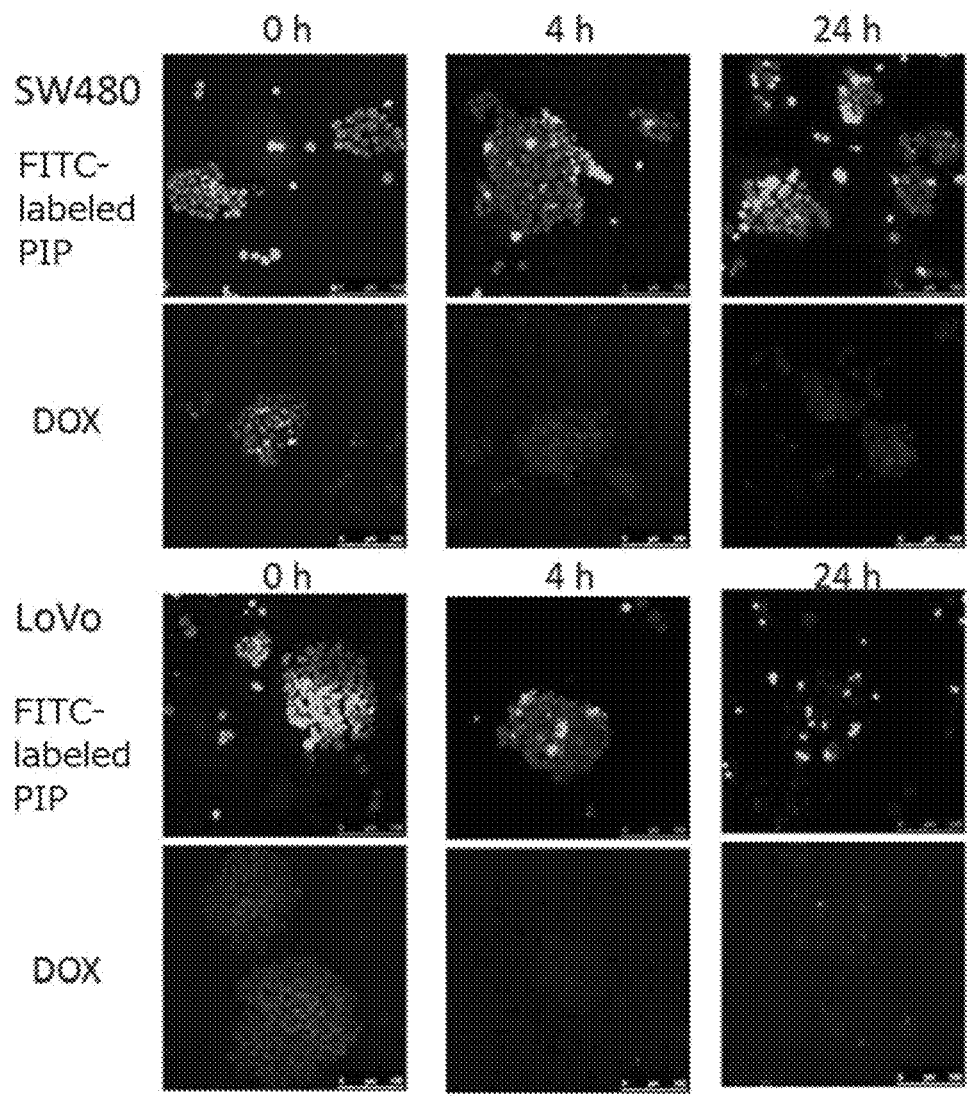
FIG. 17 is a view showing intracellular localization of KR12 in sphere-forming colon cancer cells.

The experimental results are shown in FIG. 17. The FITC-labeled KR12 (1 µmol) was administered to colon cancer forming a sphere as a model of cancer stem cells, and as a result, fluorescence was observed in the nucleus of cells in the sphere. The fluorescence was continuously observed even 24 hours after initiation of the observation. It has been known that a low-molecular-weight compound such as doxorubicin is quickly discharged from sphere-forming colon cancer cells comprising activated ABC transporters. In contrast, the results regarding KR12 demonstrate that KR12 has remained in the nucleus of the cell for a long period of time without being discharged therefrom. The results suggest that KR12 would be hardly influenced by a drug excretion mechanism that is based on the mechanism of drug resistance because it reaches the inside of the nucleus of a cancer stem cell, and thus that KR12 would be also effective for the treatment of cancer stem cells. KR12 moves into the nucleus of a cell because of its properties that the lipid-soluble portion of the PIP structure is easily incorporated into the cell and the KR12 promptly moves into the nucleus through cytoplasm and binds to DNA. Therefore, the aforementioned results demonstrate that the complex used in the present invention does not particularly need a drug delivery system, DDS, because of the function of PIP, and the results also attest that the PIP itself can be DDS for delivering various low-molecular-weight compounds to a specific genome.

14. Test Regarding Property of Accumulating in Tumor

Figure 18:
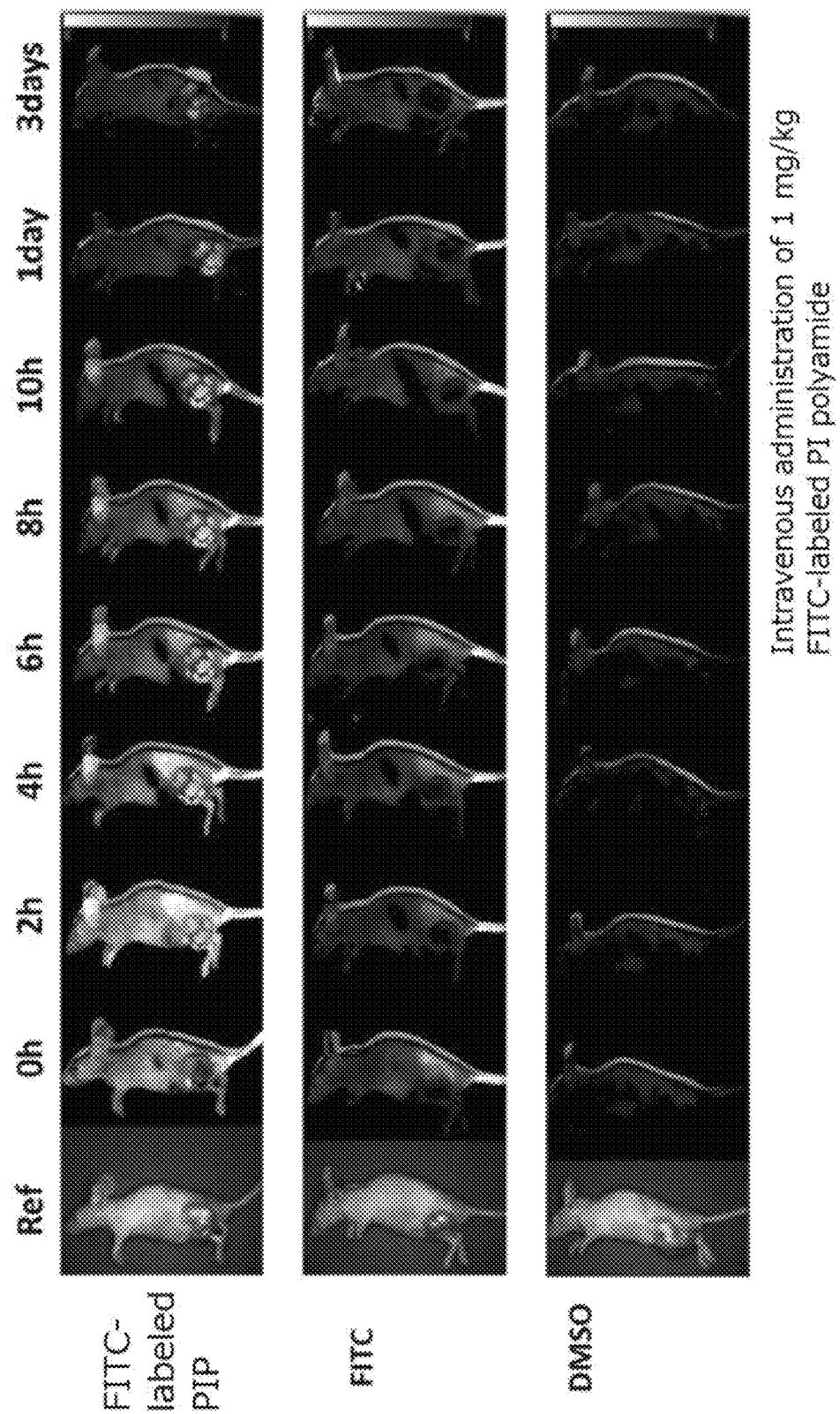
FIG. 18 is a view showing observation of the pharmacokinetics of KR12 in cancer-bearing nude mice.
Figure 19:
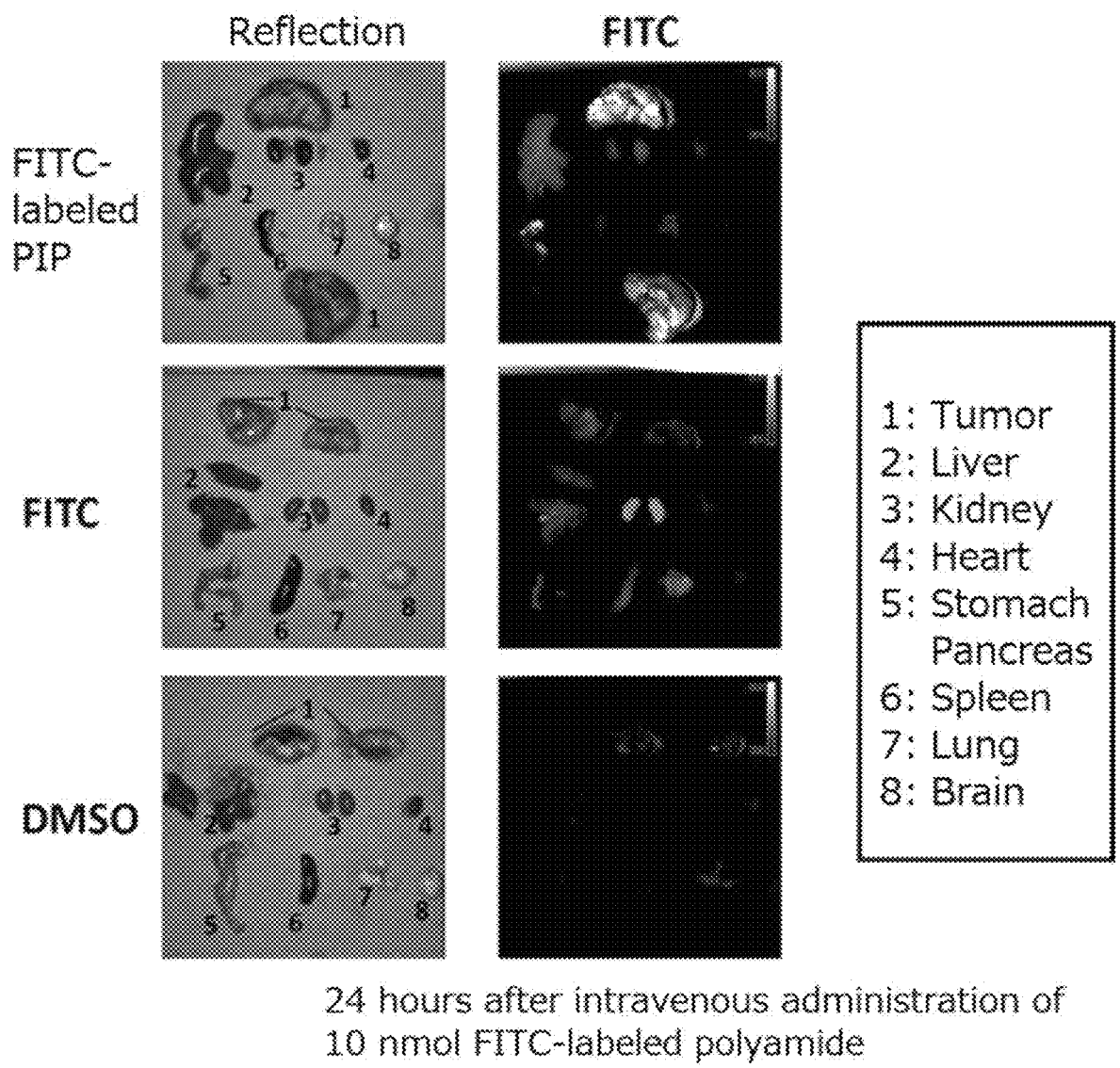
FIG. 19 is a view showing observation of accumulation of KR12 in various types of organs.

Into 5-week-old female BALB/c (nu/nu) mice, which had been purchased when they had been 4 weeks old, $5\times10^6$ SW480 cells were subcutaneously transplanted. Thereafter, when the diameter of a tumor became 15 mm, FITC-labeled KR12 (10 nmol dissolved in 1.25% DMSO (200 μl)), or FITC (1 mg/kg FITC dissolved in 1.25% DMSO (200 μl)), or 200 μl of 1.25% DMSO, was administered to each mouse via the caudal vein thereof. From hour 0 (zero) to hour 10, the image of an individual mouse was photographed at intervals of 2 hours, using an in vivo imaging system (NIPPON ROPER: Lumazone FA), and even 1 day and 3 days later, the fluorescent level and the individual mouse were photographed (FIG. 18). Furthermore, 24 hours later, mice, which had been subjected to the same treatment as described above, were dissected, and organs and tumors were then removed from the individual mice. The removed organs and tumors were photographed using an in vivo imaging system (NIPPON ROPER: Lumazone FA) (FIG. 19). Further, the same human colon cancer cells as described above were transplanted into the subcutis of several mice, and 1 mg/kg FITC-labeled KR12 (dissolved in 1.25% DMSO (200 μl)) or 200 μl of 1.25% DMSO was then administered to the mice via the caudal vein thereof. Twenty-four hour later, tumor was excised from each mouse, and was then embedded in OCT compound, followed by freeze-drying. A freeze-dried section (10 microns) was produced using LEICA CM1510S, and it was then observed under a confocal microscope (Leica, TCS-SPE) (FIG. 20).

Figure 20:
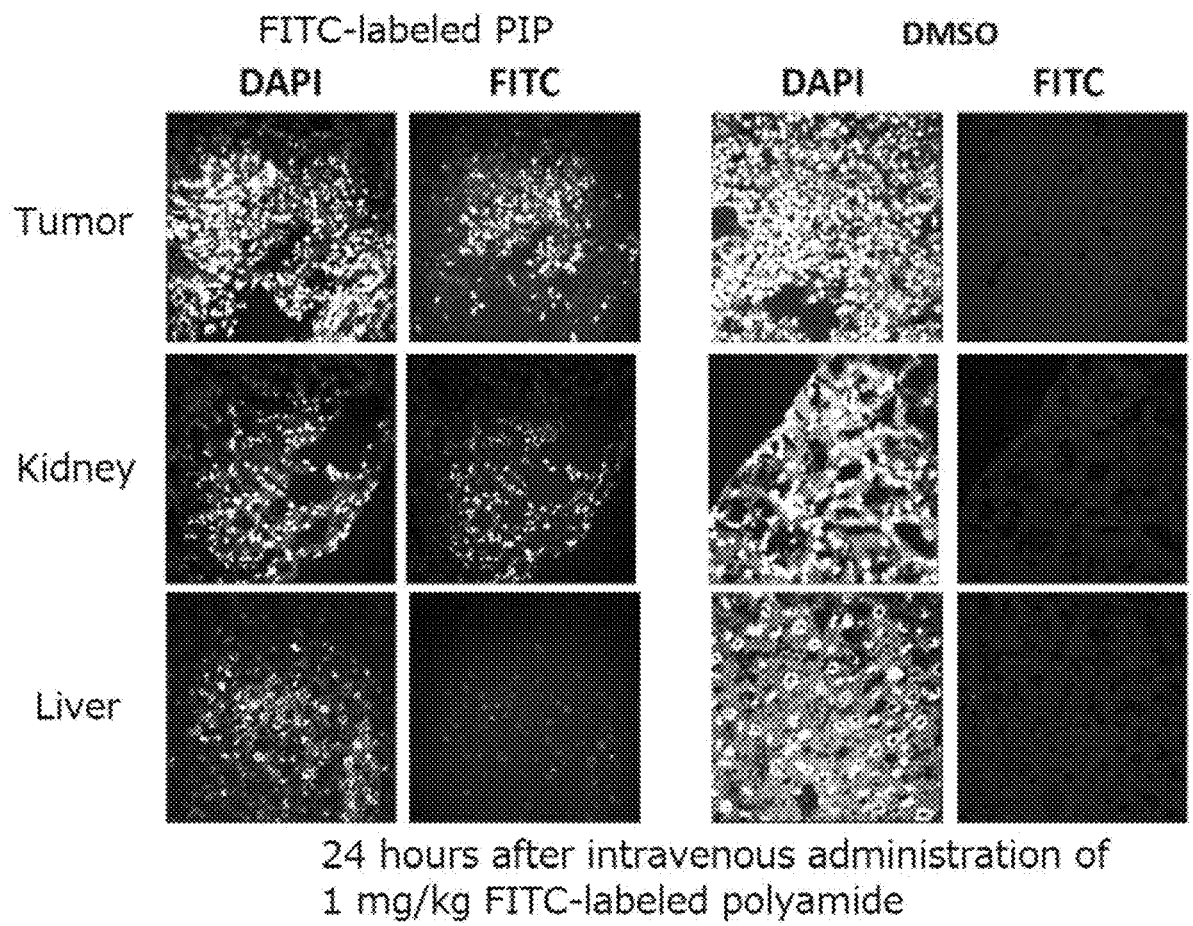
FIG. 20 is a view showing observation of the intracellular localization of KR12 in tumor, liver, and kidney cells.

The experimental results are shown in FIG. 18 to FIG. 20. The FITC-labeled KR12 (10 nmol) was administered into the vein of nude mice, into which SW480 cells had been transplanted, and thereafter, their fluorescent image was observed over time. As a result, KR12 showed the property of accumulating in tumor, by which the KR12 was distributed to the entire body, was accumulated in the tumor, and was gradually discharged from the liver and the kidney (FIG. 18). Moreover, after completion of the intravenous injection, the KR12 distributed over the entire body was accumulated in the tumor over time, and even 3 days after the administration, fluorescence was observed in the tumor. Thereafter, twenty-four hours after the administration, the mice were dissected, and incorporation of FITC into various organs was observed. As a result, the strongest fluorescence was found in the tumor, and such fluorescence was not observed, or was hardly observed in other organs (i.e., heart, stomach, pancreas, spleen, lung, and brain), and thus, a majority of KR12 was discharged (FIG. 19). Furthermore, localization of KR12 in the cells of tumor, liver, and kidney was observed under a fluorescence microscope. As a result, fluorescence was found in the nucleus (FIG. 20). The presence of absence of HR12 and a decomposed product thereof in mouse urine and mouse bile was examined by mass spectrometry. As a result, KR12 was discharged in a state in which it was not subjected to metabolic degradation. In the case of tumor cells, lipids are required for the synthesis of a cell membrane or the like, together with cell division, and thus, in general, incorporation of lipids is increased. In addition, excretion via the lymphatics is undeveloped. It is thereby considered that the property of KR12 of specifically accumulating in tumor is caused by the phenomenon that a lipid-soluble portion of PIP possessed by KR12 promotes incorporation of the KR12 into cancer cells and prevents the excretion of the KR12 from the tumor. Such accumulation of KR12 in the liver and the kidney is observed even in normal cells. However, since KR12 cannot retain in the cells, it is discharged into bile and/or urine, and is then excreted from these organs. That is, KR12 has excellent effects that it is promptly discharged from normal cells and retains in cancer cells for a long period of time.

Example 2

1. Overview

Figure 21:
FIG. 21 is a view showing the F1174L mutation of the ALK gene and the designing of PIP.
Figure 21:
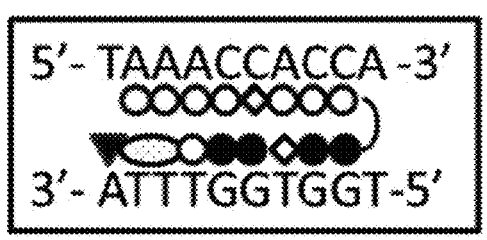

The ALK gene is a driver oncogene, which forms a fusion gene causing lung cancer, or has a point mutation constantly activating in neuroblastoma, thereby promoting canceration. It has been known that an ALK inhibitor is effective for cancer cells having an ALK gene mutation. However, in many cases, the cancer cells become resistant to such an ALK inhibitor and the cancer often recurs. The ALK gene mutation F1174L (3522C>A) in neuroblastoma is found in the neuroblastoma cells SK-N-SH, SMS-SAN, KELLY, and LAN-1. Hence, a ten-nucleotides-recognizing PIP-indole-secoCBI compound, ALK-FL-1, which specifically recognizes this mutated sequence, was synthesized by the same method as that applied to the synthesis of KR12 (FIG. 21).

2. Synthesis of ALK Gene-Alkylating PIP (ALK-FL-1)

Figure 22:
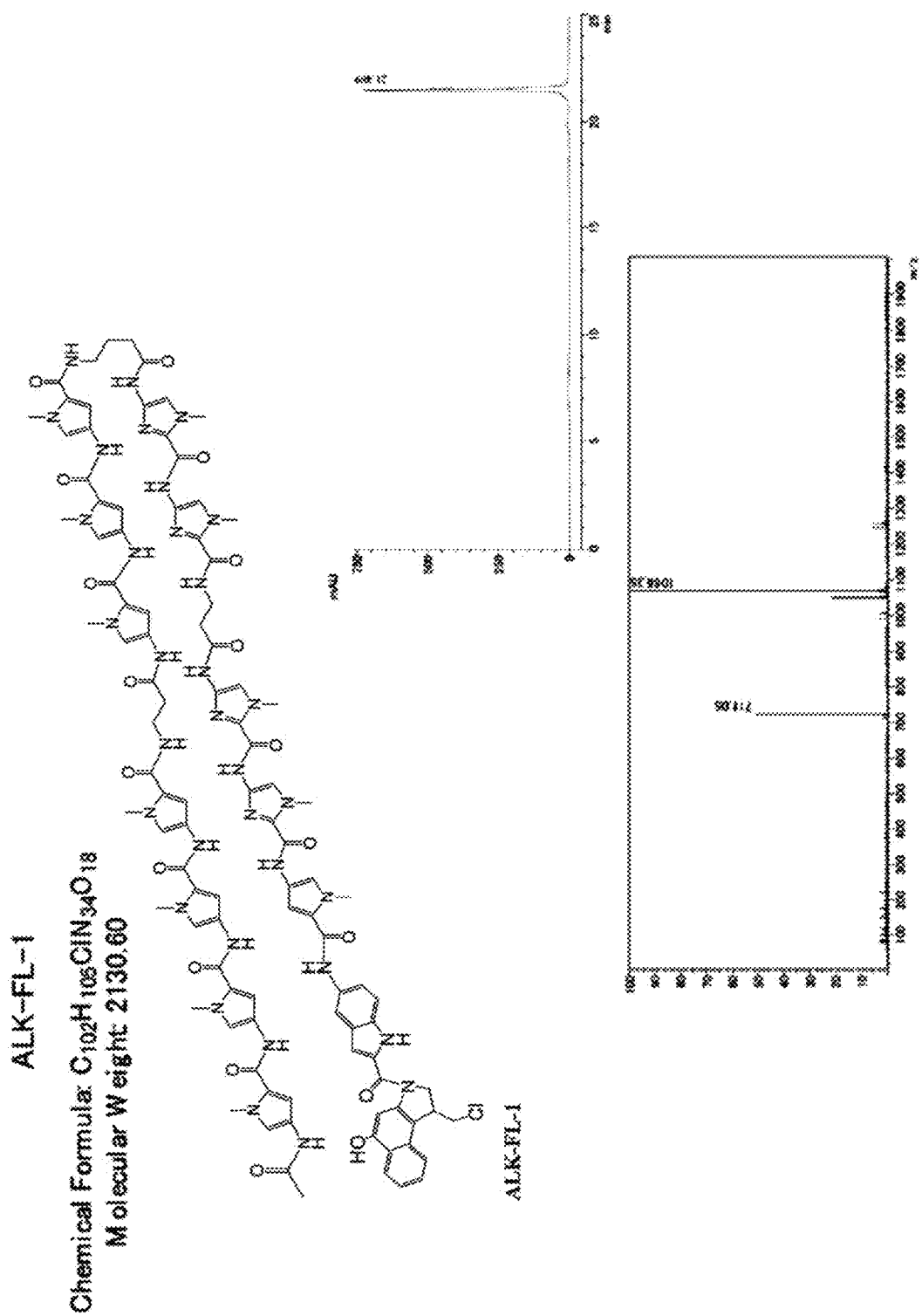
FIG. 22 is a view showing the chromatograms of HPLC and LC-MS, which are related to the synthesis of PIP (ALK-FL-1) that alkylates the F1174L mutation of the ALK gene.

The chemical structure of the ALK gene-alkylating PIP (ALK-FL-1) is represented by a chemical formula as shown below (FIG. 22). A method for producing the compound of the present invention is as follows. The F1174L (3522C>A) mutation was designed as a ten-nucleotides-recognizing PIP-indole-secoCBI compound that is allowed to recognize the mutated 5'-TGGTGGTTTA-3, which is formed by disposing a pyrrole that cannot recognize the guanine at position 2 from the 3'-terminal side of the wild-type 5'-TGGTG-GTTGA-3 sequence, to a ten-nucleotides-recognizing PIP-indole-secoCBI compound.

[Formula 18]

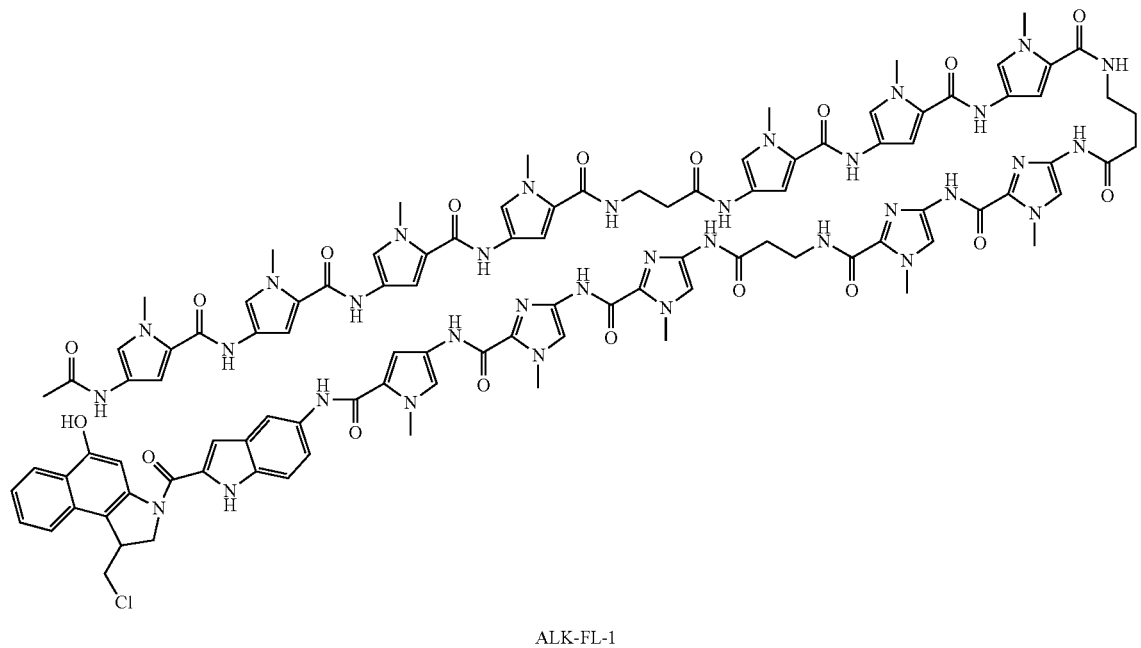

ALK-FL-1

3. Cytotoxicity Test Performed on Neuroblastoma Cells and Breast Cancer Cells, and Measurement of 50% Inhibitory Concentration (IC50)

The experiment was carried out in the same manner as that in the case of using KR12. The cells used in the experiment were Kelly cells, SK-N-SH cells, IMR-32 cells, SK-N-AS cells, and MDA-MB-231 cells. These cells were cultured in a DMEM, 10% FBS and 1% Pen/St medium, and in an RPMI1640, 10% FBS and 1% Pen/St medium, respectively. The cells of each type were seeded in each well of a 96-well plate at a cell density of 1000 cells/50 μl/well, and were then cultured under conditions of 37° C., 5% CO2, and saturated humidity for 24 hours. Thereafter, a reagent was diluted with a medium (final concentration: 1, 3, 10, 30, and 100 nM), and the diluted reagent was then added to the cultured cells in an amount of 50 μl/well, and the obtained mixture was then blended. The thus obtained mixture was cultured again under conditions of 37° C., 5% CO2, and saturated humidity for 72 hours. Thereafter, Cell Counting Kit-8 (DOJINDO) was added to the obtained culture in an amount of 10 μl/well, and the thus obtained mixture was blended and was then cultured under conditions of 37° C., 5% CO2, and saturated humidity for 2 hours. The absorbance was measured using Microplate Reader MTP-310 Lab (COLONA ELECTORIC), and the IC50 value was then calculated.

Figure 23:
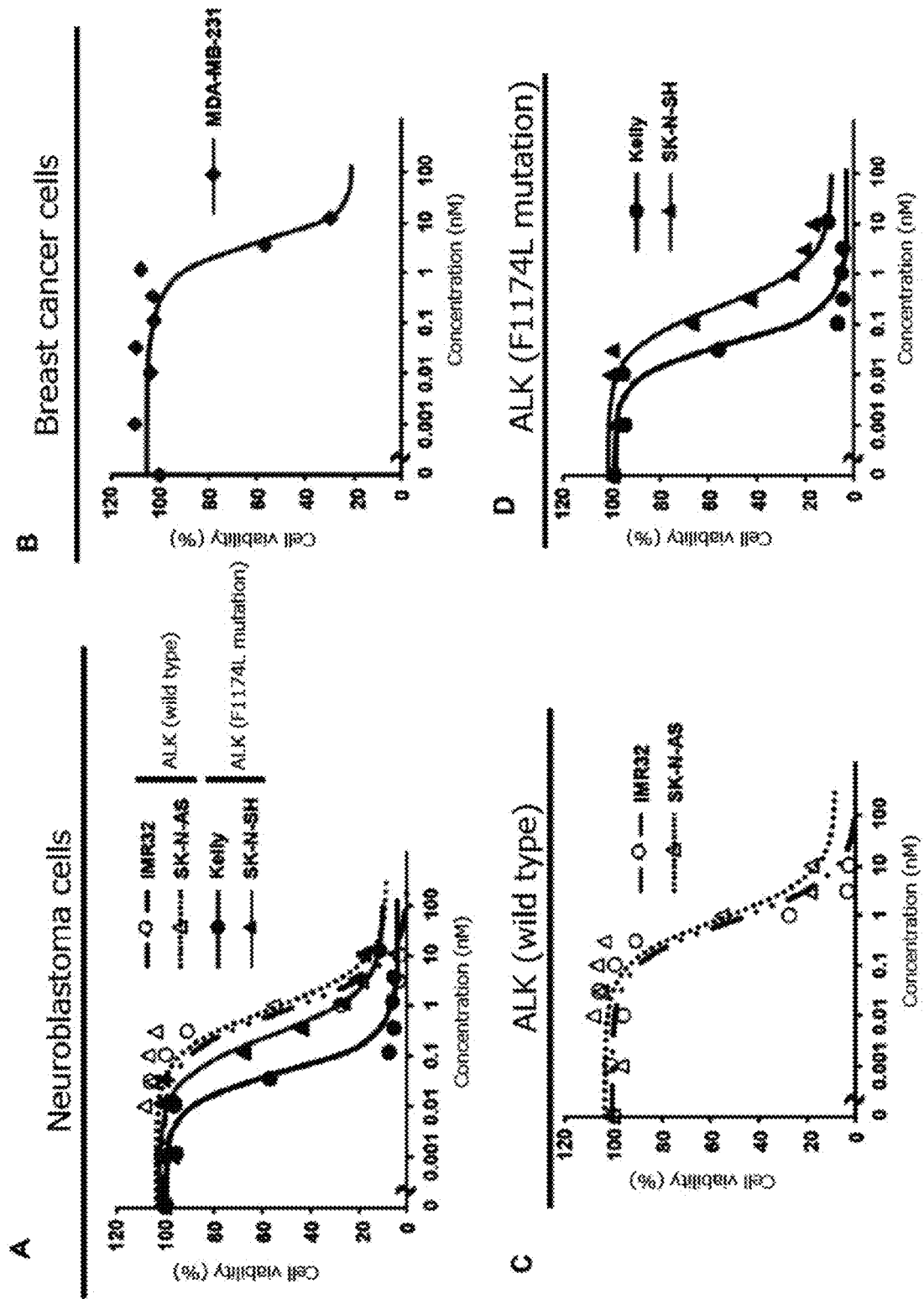
FIG. 23 is a view showing the results obtained by measuring the cell growth of neuroblastoma cells and breast cancer cells, which have been treated with ALK-FL-1 according to WST assay, and then measuring IC50 (50% inhibitory concentration).

The experimental results are shown in FIG. 23 and Table 5. When ALK-FL-1 was administered to the cells of each type, it exhibited a high effect of suppressing cell grown on neuroblastoma cells having an F1174L mutation (FIG. 23A). Specifically, the IC 50 of ALK-FL-1 was 0.09 nM to the Kelly cell line, and it was 0.13 nM to the SK-N-SH cell line. On the other hand, the IC50 of ALK-FL-1 was 0.46 nM to the IMR-32 cell line, and 2.6 nM to the SK-N-AS cell line, both of which are wild-type neuroblastoma cell lines. Also, the IC50 of ALK-FL-1 was 7.5 nM to the MDA-MB-231 cell line that is a breast cancer cell line not having an F1174L mutation (wild-type ALK gene) (FIGS. 23A-D and Table 5). From these results, it was found that ALK-FL-1 exhibits stronger growth suppression specifically to neuroblastoma cell lines having an F1174L mutation.

TABLE 5

| ALK-FL-1 | IMR32 | SK-N-AS | Kelly | SK-N-SH | MDA-MB-231 |
|---|---|---|---|---|---|
| $IC_{50}$ | 0.46 | 2.6 | 0.09 | 0.13 | 7.5 |

Concentration (nM)

Example 3

1. Overview

Figure 24:
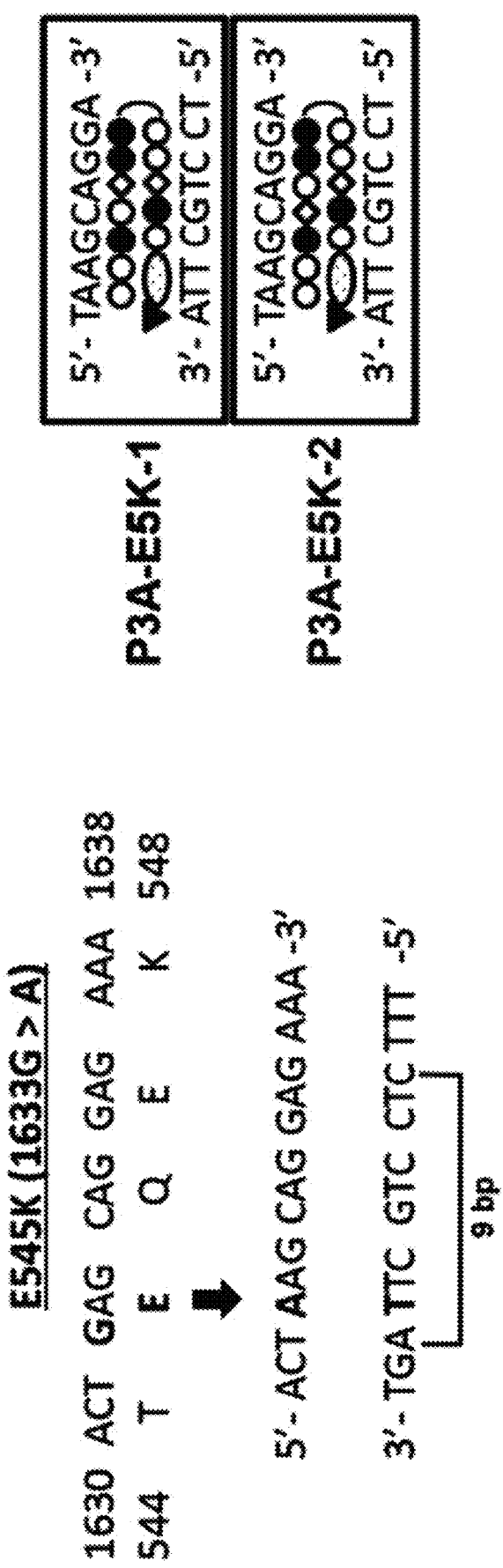
FIG. 24 is a view showing the E545K mutation of the PIK3CA gene and the designing of PIP.

Regarding the PIK3CA gene, it has been reported that mutations are concentrated in three hot spots, namely, the helical domains of exon 10, E545K and E542K, and the kinase domain of exon 21, H1047R, and that these mutations occur at high frequencies in breast cancer, colon cancer, endometrial cancer, liver cancer, and brain glioblastoma. On the other hand, the amplification of the PIK3CA gene not involving point mutation has been observed in cervical cancer, lung cancer, stomach cancer, ovarian cancer, and head and neck cancer. Since the PIK3CA gene serves as a driver oncogene in the PI3 kinase-Akt pathway, a PI3K inhibitor has been developed, targeting the PIK3CA gene. However, due to problems regarding toxicity and the like, the developed PI3K inhibitor has not yet been applied in clinical sites under the current circumstance. The E545K (1633G>A) mutation of the PIK3CA gene has been found in the breast cancer cell line MCF7. Hence, nine-nucleotidesrecognizing PIP-indole-secoCBI compounds P3A-E5K-1 and P3A-E5K-2, which specifically recognize the aforementioned mutated sequence, were synthesized by the same method as in the case of the synthesis of KR12 (FIG. 24).

2. Synthesis of PIK3CA Gene-Alkylating PIP (P3A-E5K-1)

Figure 25:
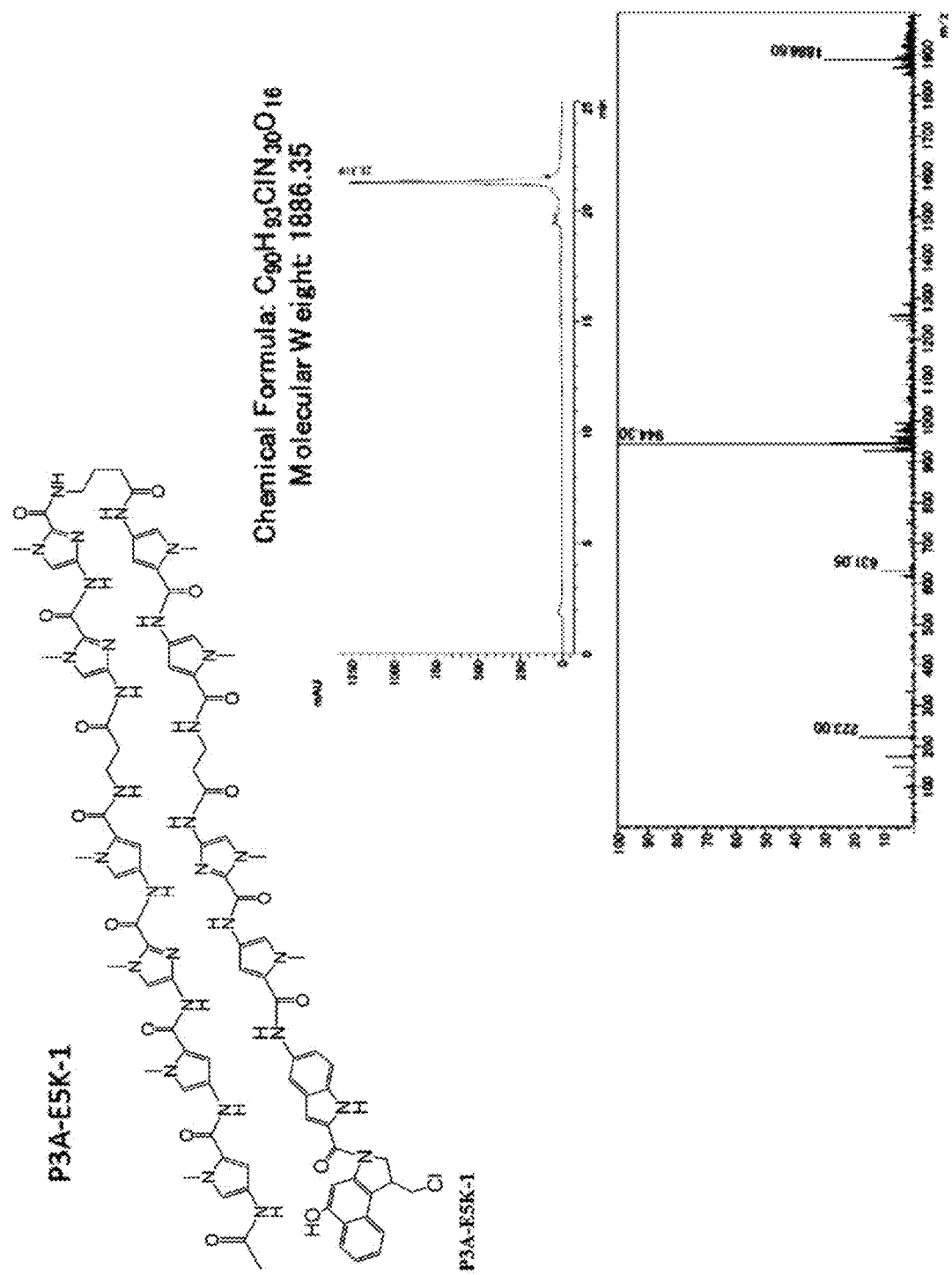
FIG. 25 is a view showing the chromatograms of HPLC and LC-MS, which are related to the synthesis of PIP (P3A-E5K-1) that alkylates the E545K mutation of the PIK3CA gene.
Figure 26:
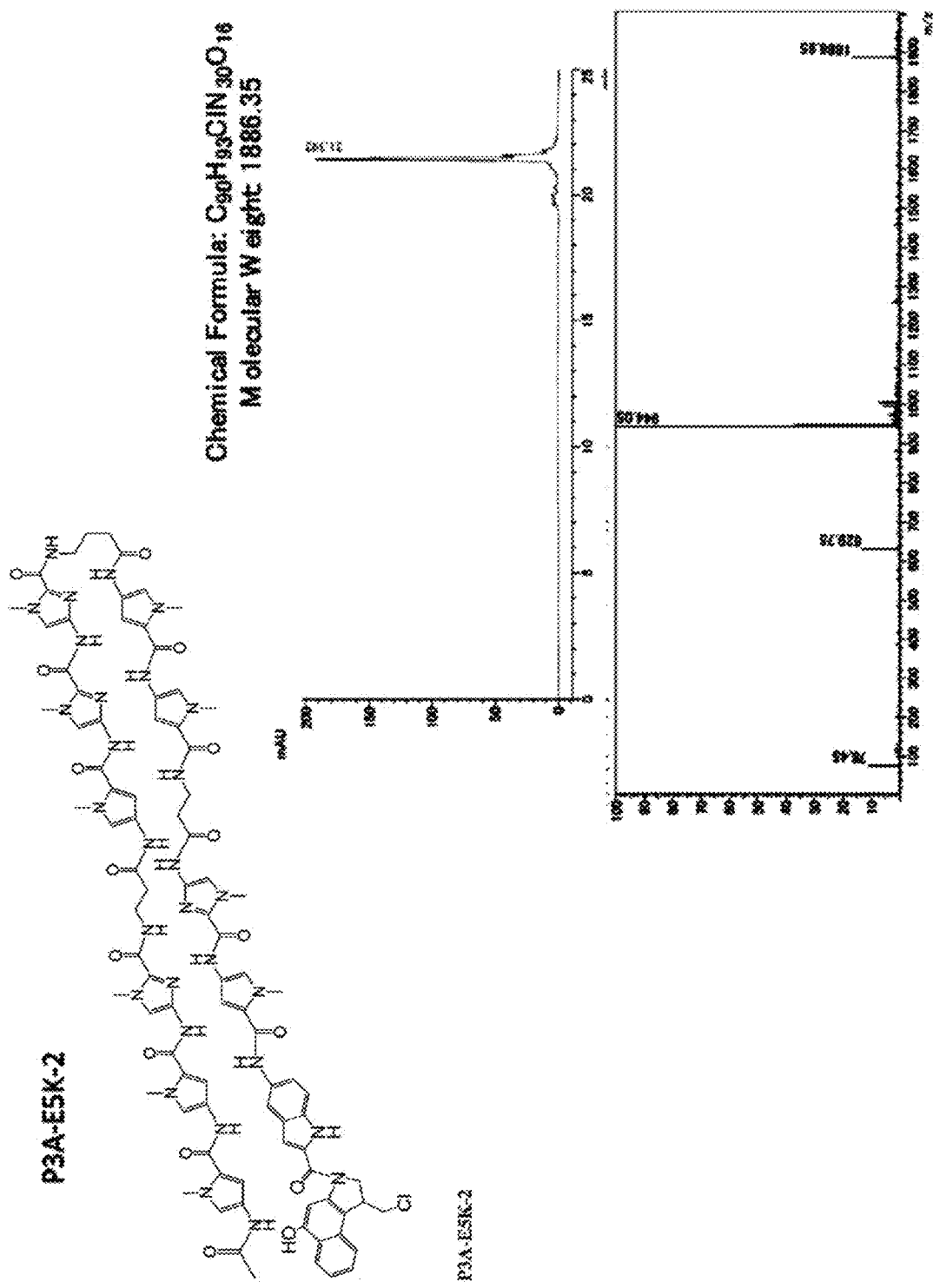
FIG. 26 is a view showing the chromatograms of HPLC and LC-MS, which are related to the synthesis of PIP (P3A-E5K-2) that alkylates the E545K mutation of the PIK3CA gene.

The chemical structure of the PIK3CA gene-alkylating PIP (P3A-E5K-1) is represented by a chemical formula as shown below. A method for producing the compound of the present invention is as follows (FIGS. 25 and 26). For recognition of the E545K (1633G>A) mutation, PIP-Indole-seco-CBI that recognizes 5'-CTCCTGCTTA-3' was designed. This compound was designed, such that it could not recognize the cytosine at position 2 from the 3'-terminus of the wild-type 5'-CTCCTGCTCA-3' and could not alkylate the adenine at the 3'-terminus, but it could alkylate it in the mutated sequence.

[Formula 19]

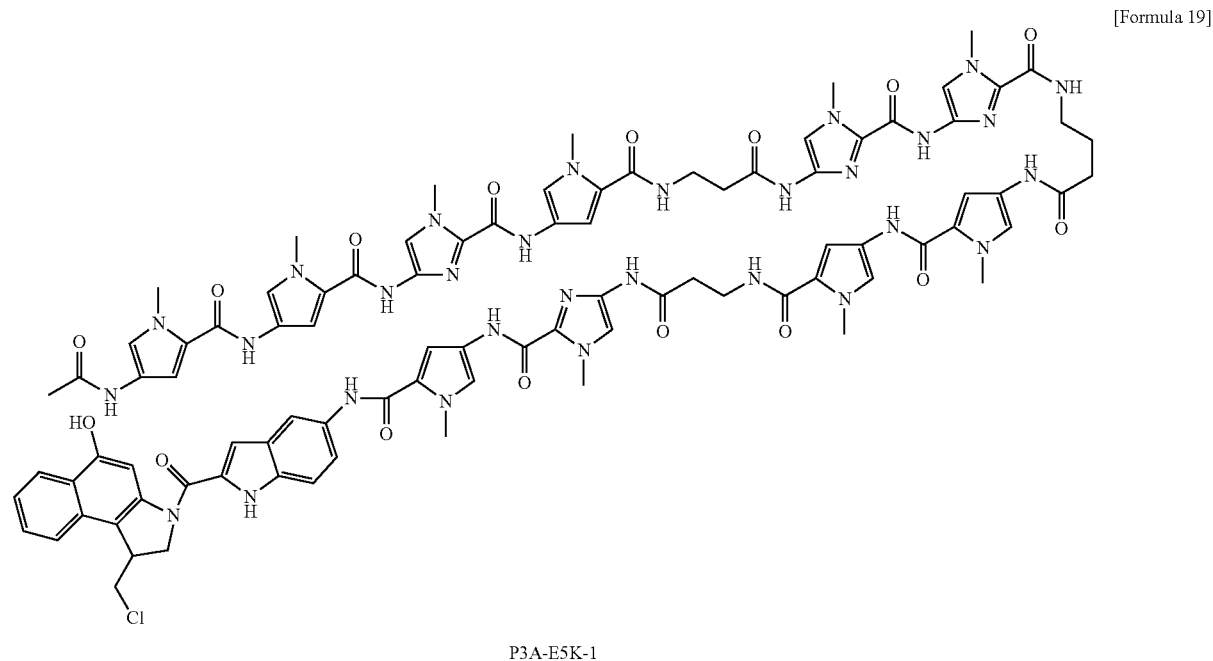

P3A-E5K-1

[Formula 20]

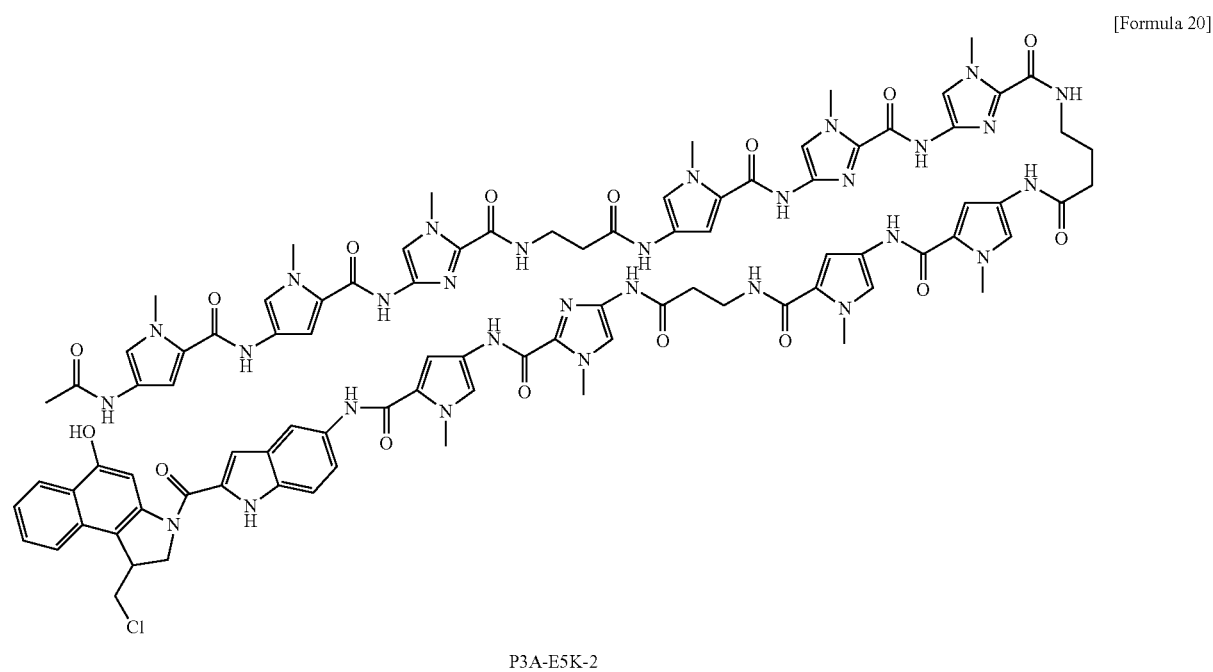

P3A-E5K-2

3. Cytotoxicity Test Performed on Breast Cancer Cells, and Measurement of 50% Inhibitory Concentration (1050)

The experiment was carried out in the same manner as that in the case of using KR12. The cells used in the experiment were MCF7 cells and MDA-MB-231 cells. These cells were cultured in a DMEM, 10% FBS and 1% Pen/St medium, and in an RPMI1640, 10% FBS and 1% Pen/St medium, respectively. The cells of each type were seeded in each well of a 96-well plate at a cell density of 1000 cells/50 μl/well, and were then cultured under conditions of 37° C., 5% CO2, and saturated humidity for 24 hours. Thereafter, a reagent was diluted with a medium (final concentration: 1, 3, 10, 30, and 100 nM), and the diluted reagent was then added to the cultured cells in an amount of 50 μl/well, and the obtained mixture was then blended. The thus obtained mixture was cultured again under conditions of 37° C., 5% CO2, and saturated humidity for 72 hours. Thereafter, Cell Counting Kit-8 (DOJINDO) was added to the obtained culture in an amount of 10 μl/well, and the thus obtained mixture was blended and was then cultured under conditions of 37° C., 5% CO2, and saturated humidity for 2 hours. The absorbance was measured using Microplate Reader MTP-310 Lab (COLONA ELECTORIC), and the IC50 value was then calculated.

Figure 27:
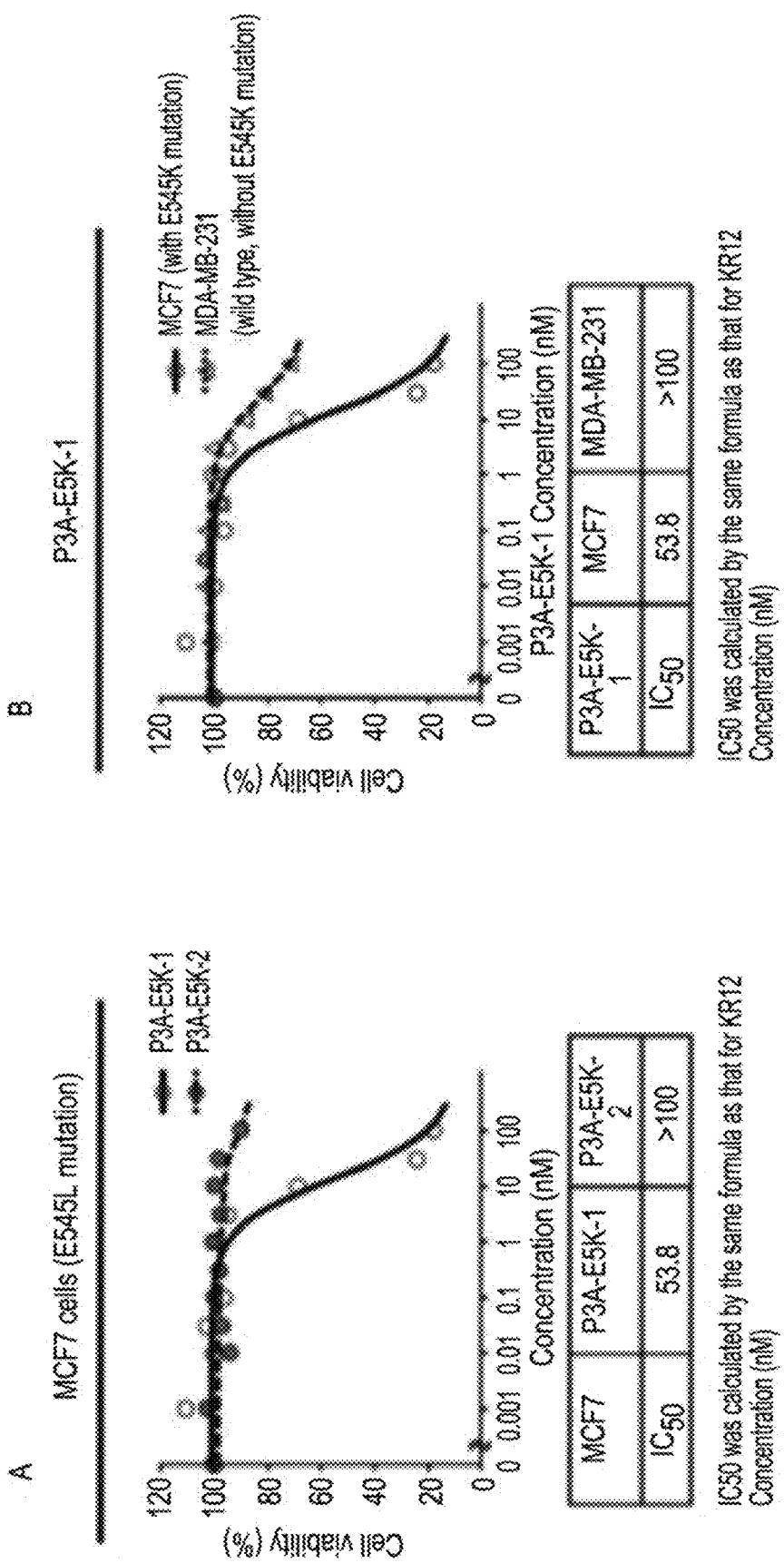
FIG. 27 is a view showing the results obtained by measuring the cell growth of breast cancer cells, which have been treated with P3A-E5K-1 and P3A-E5K-2 according to WST assay, and then measuring IC50 (50% inhibitory concentration).

The experimental results are shown in FIG. 27. The IC50 of P3A-E5K-1 was 53.8 nM to MCF7 as a breast cancer cell line having the E545K (1633G>A) mutation of the PIK3CA gene, and the IC50 of P3A-E5K-2 was >100 nM to the same above cell line (FIG. 27A). The IC50 of P3A-E5K-1 was >100 nM to MDA-MB-231 as a breast cancer cell line having a wild-type PIK3CA gene (FIG. 27B). From these results, it has been revealed that the P3A-E5K-1 produced against cancer cell lines having a PIK3CA gene E545K mutation has a significantly stronger tumor growth-suppressing effect on breast cancer cell lines having such an E545K mutation than on breast cancer cell lines not having such a mutation.

Example 4

1. Overview

Figure 28:
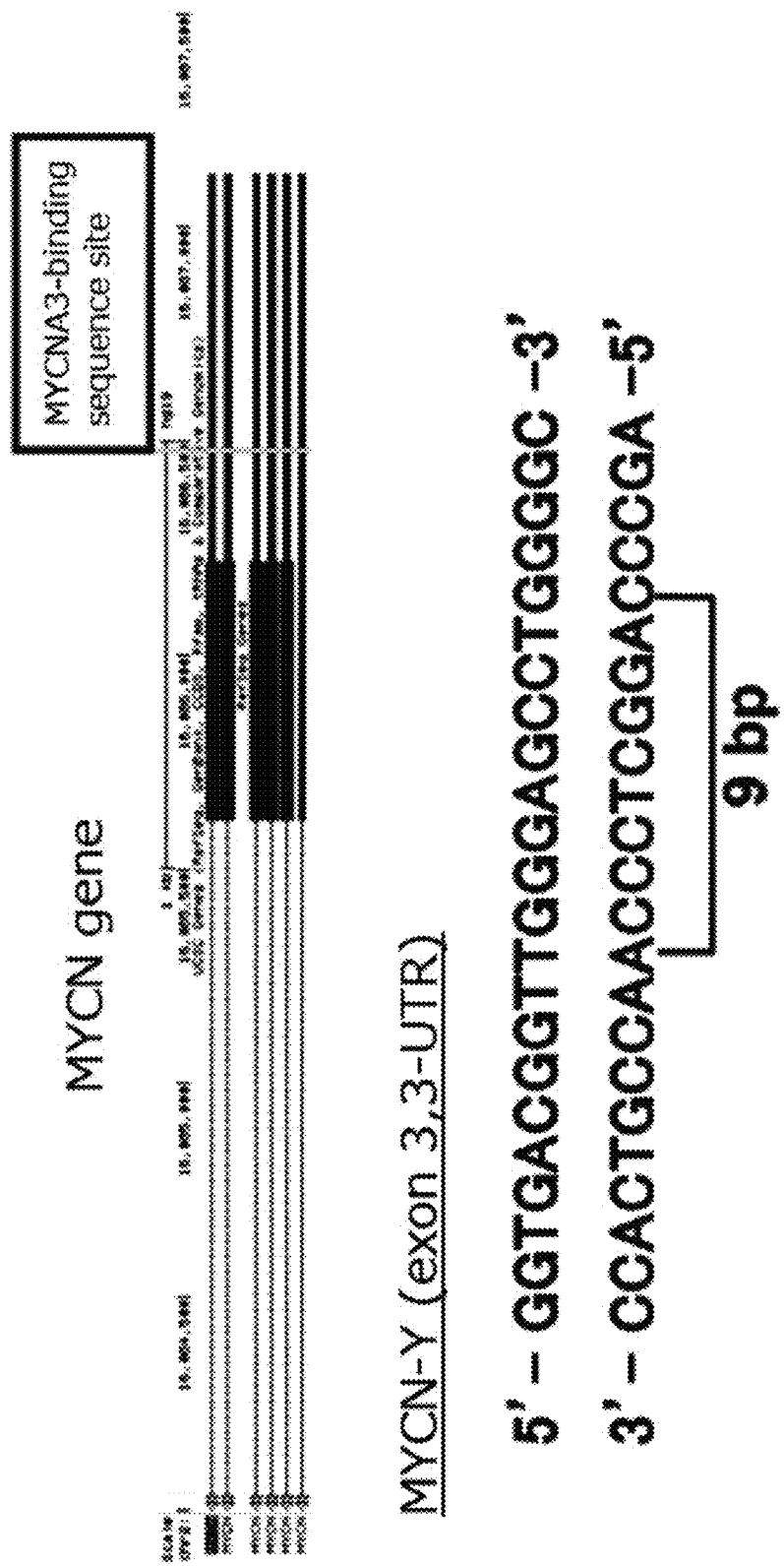
FIG. 28 is a view showing the binding site of the exon 3 of the MYCN gene with MYCN3.

As a cancer cell-specific mutation, there is a genetic amplification, which is not point mutation or translocation and is not attended with a change in the gene sequence. This mutation is referred to as a copy number change mutation. A specific cancer-related gene region is amplified, and as a result, the expression level of the oncogene is increased, and canceration is thereby promoted. We have considered that a compound alkylating a specific genomic sequence, such as the compound of the present invention, would exhibit its effects, even in a case where the compound is produced, targeting a gene, the copy number of which has been increased as a result of amplification, and we have synthesized MYCN-alkylating PIPs (MYCNA1, MYCNA2, and MYCNA3) targeting MYCN that is amplified in infant neuroblastoma and the like at high frequencies and becomes a poor prognostic factor. MYCN gene is a gene that is amplified at a high frequency in neuroblastoma, and this gene is considered to be a driver oncogene of neuroblastoma. With respect to this MYCN gene, eight-nucleotides-recognizing PIP-indole-secoCBI compounds (MYCNA1 and MYCNA2), and a nine-nucleotides-recognizing PIP-indole-secoCBI compound (MYCNA3) that specifically recognizes the sequence of exon 3 (FIG. 28), were synthesized by the same method as in the case of the synthesis of KR12, as shown in FIG. 2.

2. Synthesis of MYCN Gene-Alkylating PIPs (MYCNA1, MYCNA2, and MYCNA3)

Figure 29:
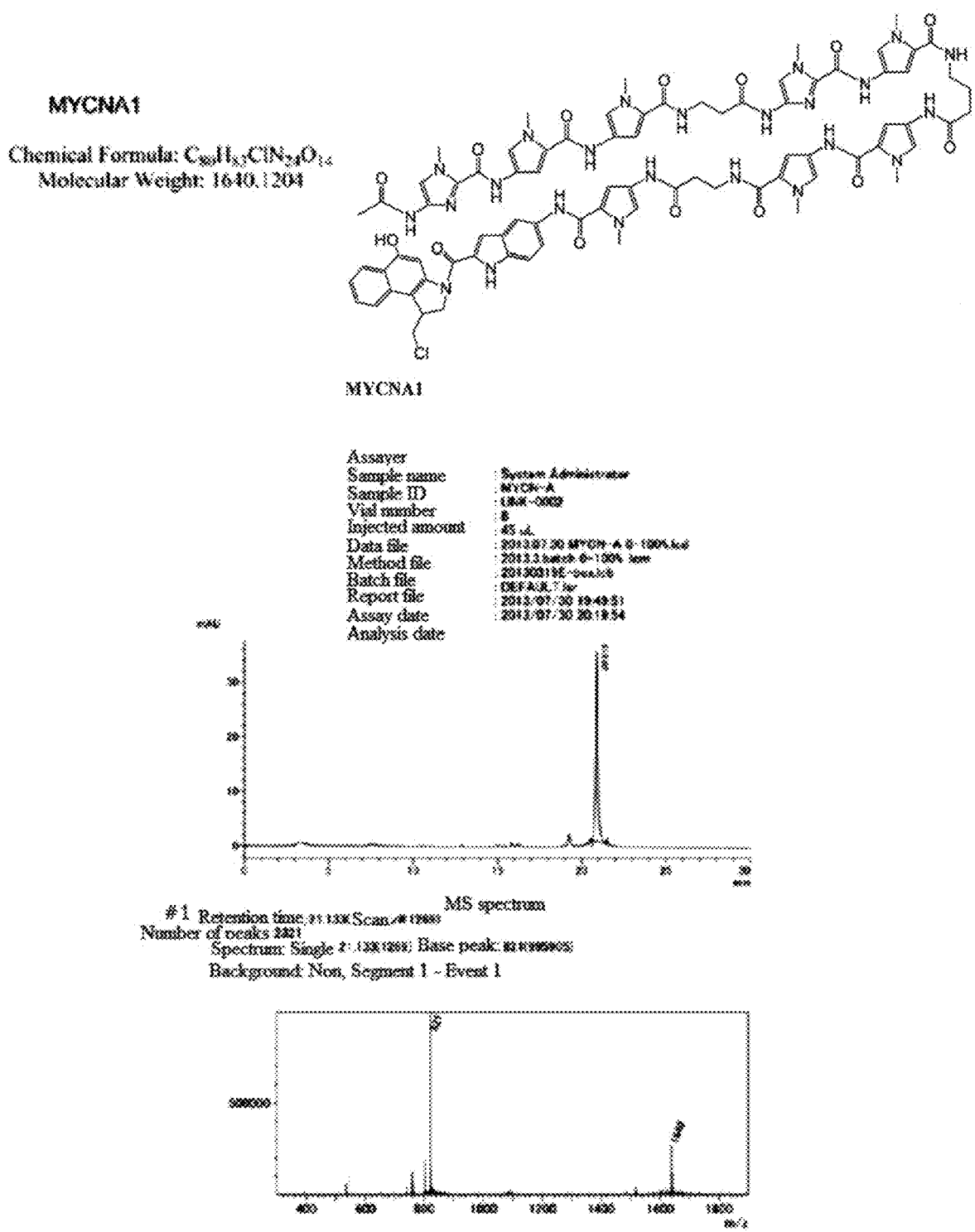
FIG. 29 is a view showing the chromatograms of HPLC and LC-MS, which are related to the synthesis of PIP (MYCNA1) that alkylates the MYCN gene.
Figure 30:
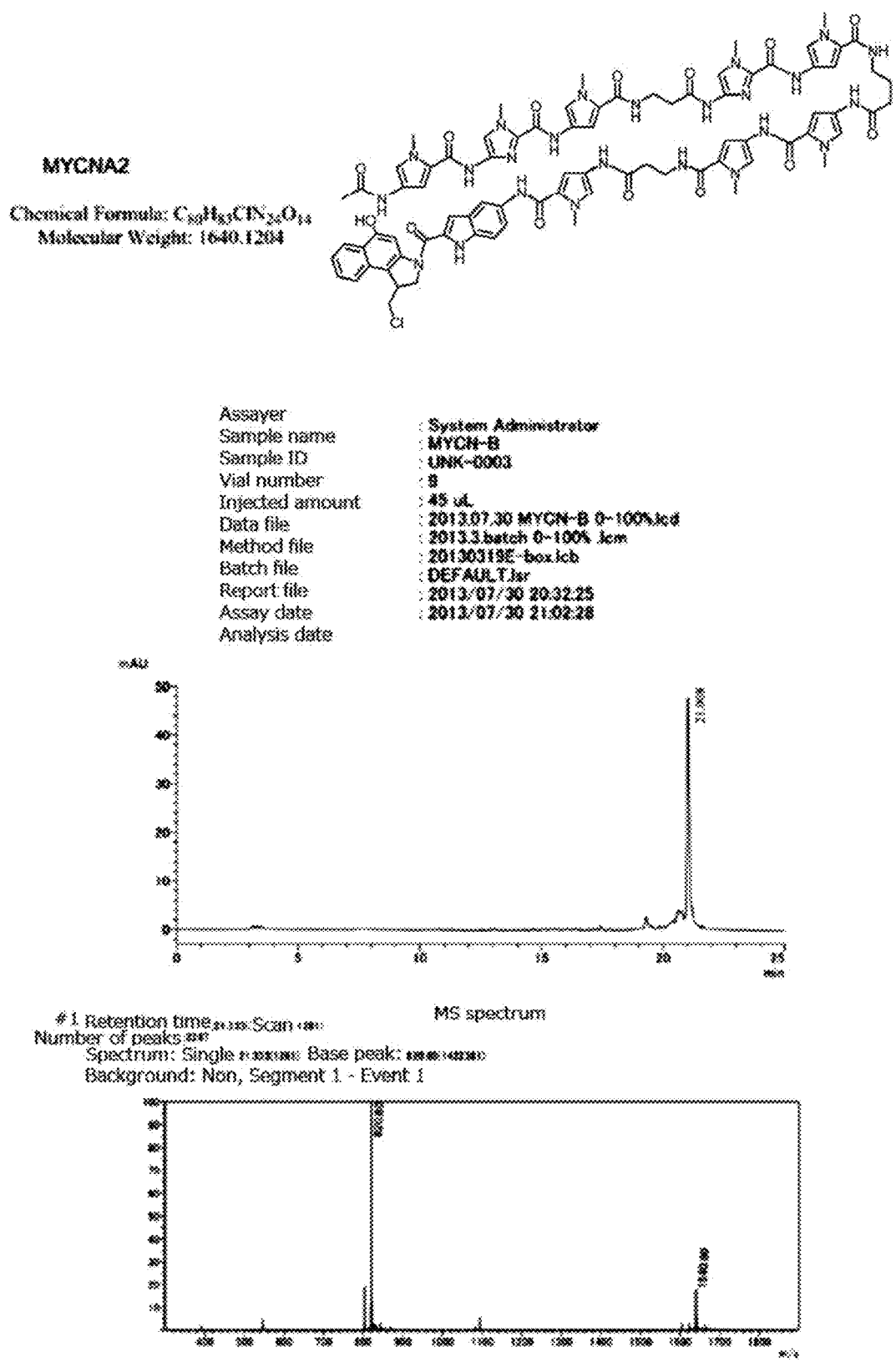
FIG. 30 is a view showing the chromatograms of HPLC and LC-MS, which are related to the synthesis of PIP (MYCNA2) that alkylates the MYCN gene.
Figure 31:
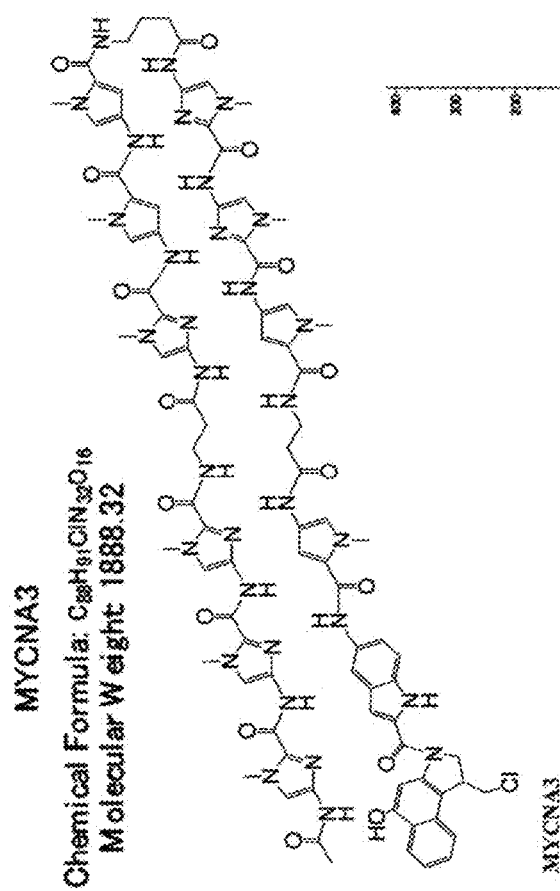
FIG. 31 is a view showing the chromatograms of HPLC and LC-MS, which are related to the synthesis of PIP (MYCNA3) that alkylates the MYCN gene.
Figure 31:
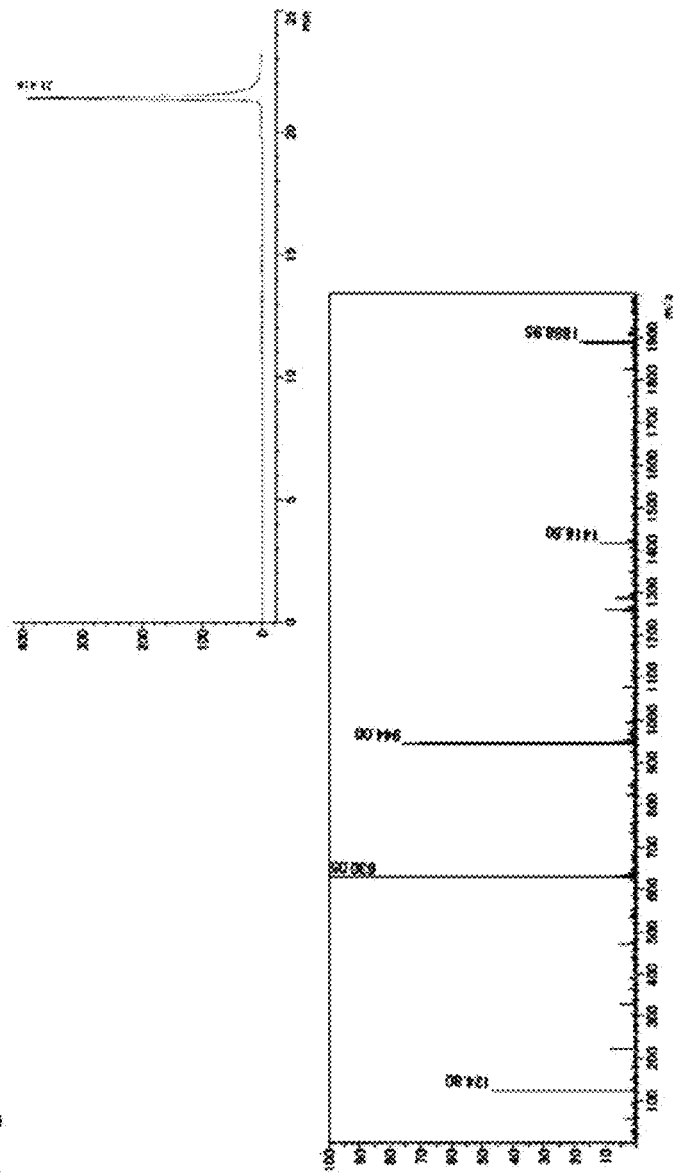

The chemical structures of the MYCN gene-alkylating PIPs (MYCNA1, MYCNA2, and MYCNA3) are represented by chemical formulae as shown below. A method for producing the compounds of the present invention is as follows. PIP having a carboxylic acid terminus was dissolved in 100 μL of DMF, and iPr2NEt (0.5 μL, 2.86 μmol) and Py BOP (1.0 mg, 1.95 μmop were then added to the above solution. While stirring, the reaction solution was reacted at room temperature for 2 hours. Thereafter, formation of an active form of 1-hydroxybenzotriazole ester was confirmed by HPLC. After the formation had been confirmed, $NH_2$-indole seco-CBI (0.6 mg, 1.58 μmol) was added to the reaction vessel, and the mixture was then stirred at room temperature in a nitrogen atmosphere overnight. Thereafter, DMF used as a solvent was removed, and the residue was subjected to liquid separation using dichloromethane and diethyl ether. The layer of reaction product was purified by HPLC (0.1% TFA/CH3CN, 30%-75% linear gradient, 0 to 30 minutes), and was then freeze-dried, so as to obtain a compound of interest, alkylating PI polyamide, MYCNA1, in the form of white powders (FIG. 29). MYCNA2 and MYCNA3 were also obtained by the same method as described above (FIGS. 30 and 31). A method of designing PIPs targeting MYCN is shown in FIG. 2.

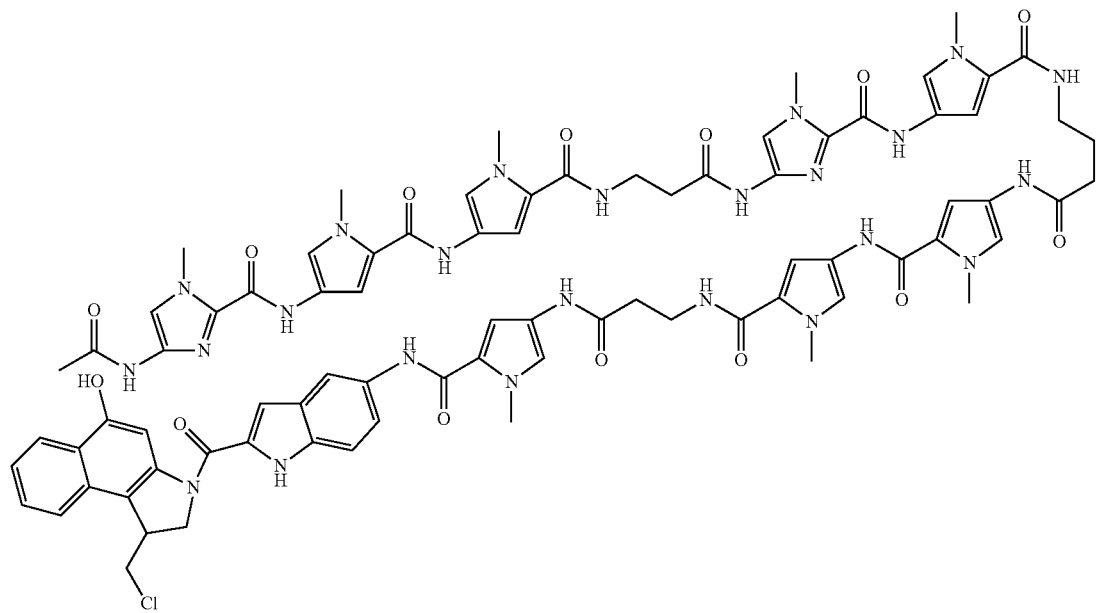
MYCNA1
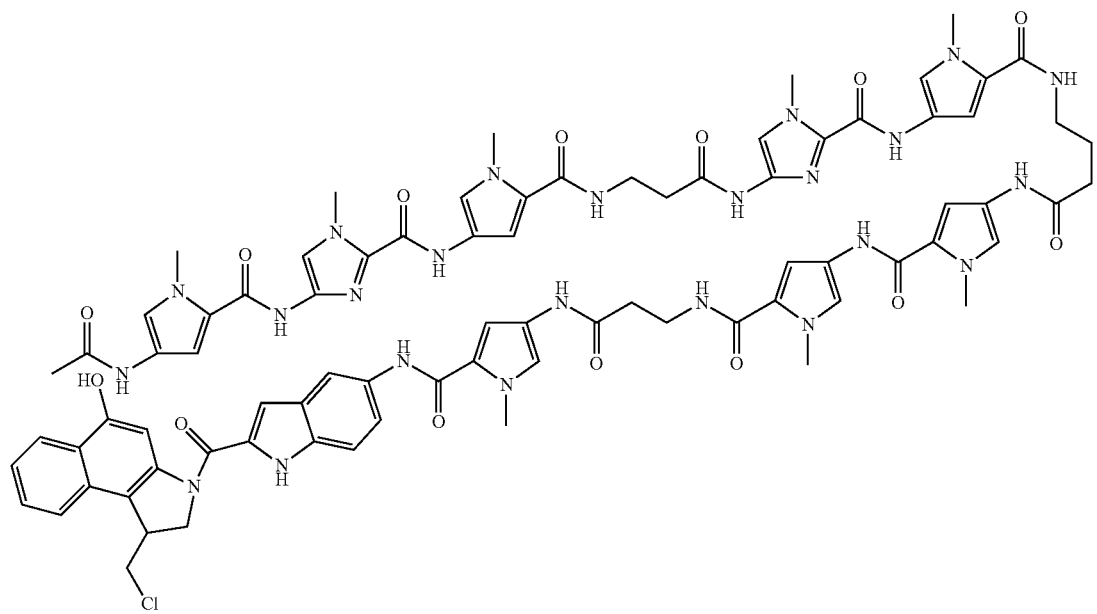
MYCNA2

-continued

[Formula 23]

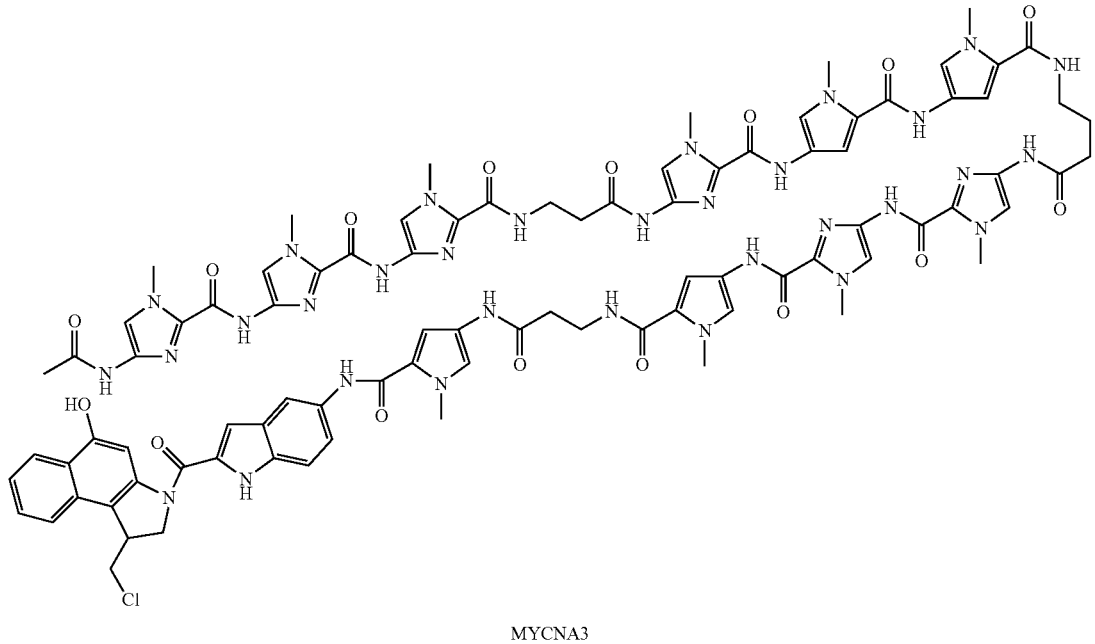

MYCNA3

3. Conformation of Cell Growth and Cell Shape Using Incucyte Culture Time-Lapse Microscope The cells were seeded in each well of a 96-well plate at a cell density of 1000 cells/50 μl/well, and were then cultured under conditions of 37° C., 5% CO2, and saturated humidity for 24 hours. On the following day, the culture media was replaced with a culture media, to which a DMSO control, or 1 nM, 3 nM, 10 nM, 30 nM or 100 nM MYCNA1 had been added, and the resulting cells were then observed under an Incucyte culture time-lapse microscope (Essen Instruments, Ann Arbor, Mich.) every 6 hours. A growth curve was produced from an imaging plate using Incucyte system (Essen Instruments, Ann Arbor, Mich.). The cells used in the experiment were neuroblastoma cell lines having MYCN amplification, IMR-32 cells (MYCN, 25 copies) and TGW cells (MYCN, 60 copies). The cells of each type were cultured in a DMEM, 10% FBS and 1% Pen/St medium, and in an RPMI1640, 10% FBS and 1% Pen/St medium, respectively.

Figure 32:
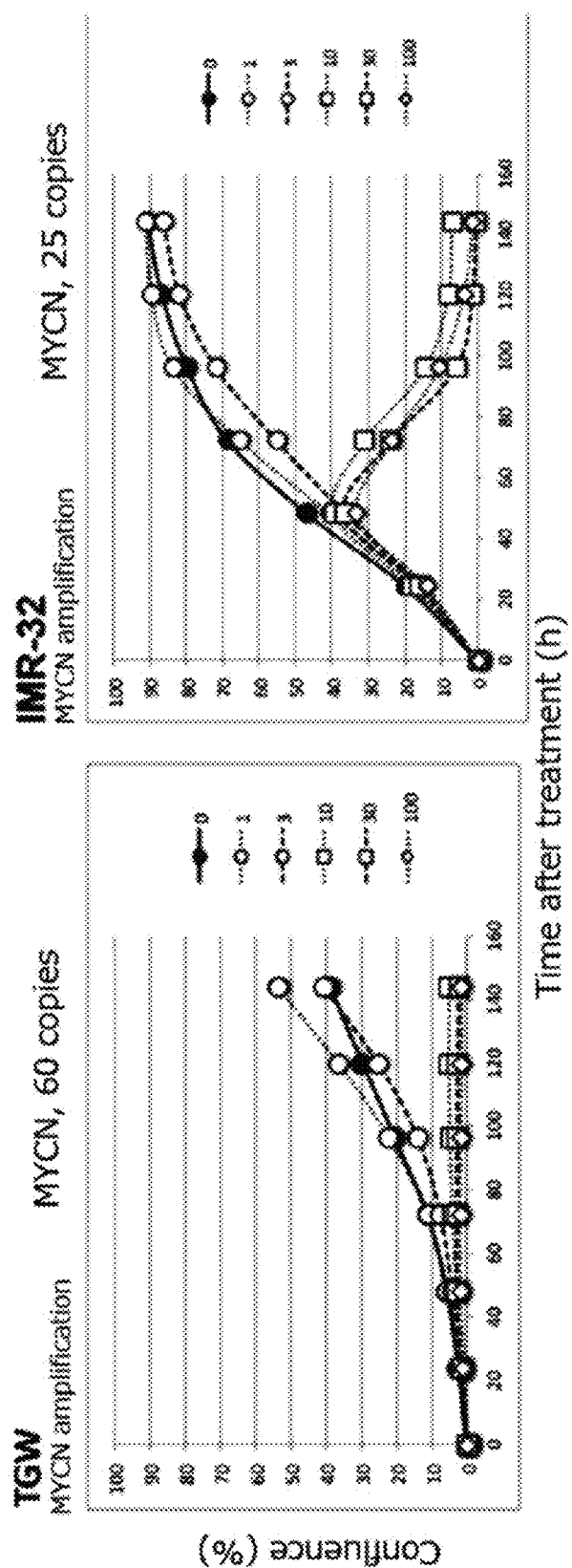
FIG. 32 is a view showing a cell growth curve produced by observing MYCNA1- and MYCNA2-treated cells under an Incucyte culture time-lapse microscope.

The results regarding the growth curves are shown in FIG. 32. It was found that the cell growth of the IMR-32 cells and the TGW cells, in which the MYCN gene was highly expressed, was suppressed by MYCNA1 in a concentration-dependent manner (FIG. 32).

4. Cytotoxicity Test Performed on Neuroblastoma Cells, and Measurement of 50% Inhibitory Concentration (IC50)

The experiment was carried out in the same manner as that in the case of using KR12. The cells used in the experiment were IMR-32 cells and TGW cells. These cells were cultured in a DMEM, 10% FBS and 1% Pen/St medium, and in an RPMI1640, 10% FBS and 1% Pen/St medium, respectively. The cells of each type were seeded in each well of a 96-well plate at a cell density of 1000 cells/50 μl/well, and were then cultured under conditions of 37° C., 5% CO2, and saturated humidity for 24 hours. Thereafter, a reagent was diluted with a medium (final concentration: 1, 3, 10, 30, and 100 nM), and the diluted reagent was then added to the cultured cells in an amount of 50 μl/well, and the obtained mixture was then blended. The thus obtained mixture was cultured again under conditions of 37° C., 5% CO2, and saturated humidity for 72 hours. Thereafter, Cell Counting Kit-8 (DOJINDO) was added to the obtained culture in an amount of 10 μl/well, and the thus obtained mixture was blended and was then cultured under conditions of 37° C., 5% CO2, and saturated humidity for 2 hours. The absorbance was measured using Microplate Reader MTP-310 Lab (COLONA ELECTORIC), and the IC50 value was then calculated.

Figure 33:
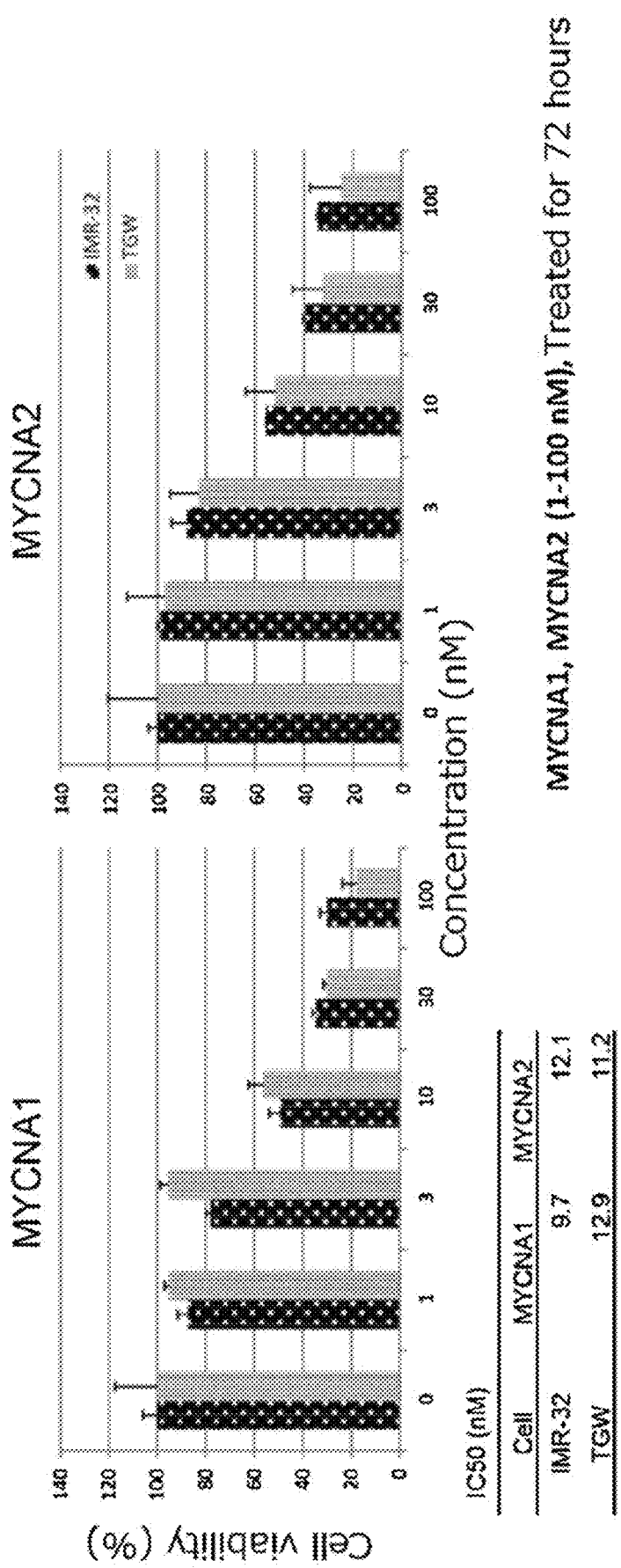
FIG. 33 is a view showing a cytotoxicity test using MYCNA1-treated neuroblastoma cells and the measurement results of the 50% inhibitory concentration (IC50).

The experimental results are shown in FIG. 33. The IC50 of MYCNA1 was 9.7 nM to the IMR-32 cells, and it was 12.9 nM to the TGW cells. The IC50 of MYCNA2 was 12.1 nM to the IMR-32 cells, and it was 11.2 nM to the TGW cells. That is to say, it is considered that MYCNA1 and MYCNA2 can induce suppression of the growth of cancer cells, in which the MYCN gene is highly expressed, even when they are used at low concentrations.

Figure 34:
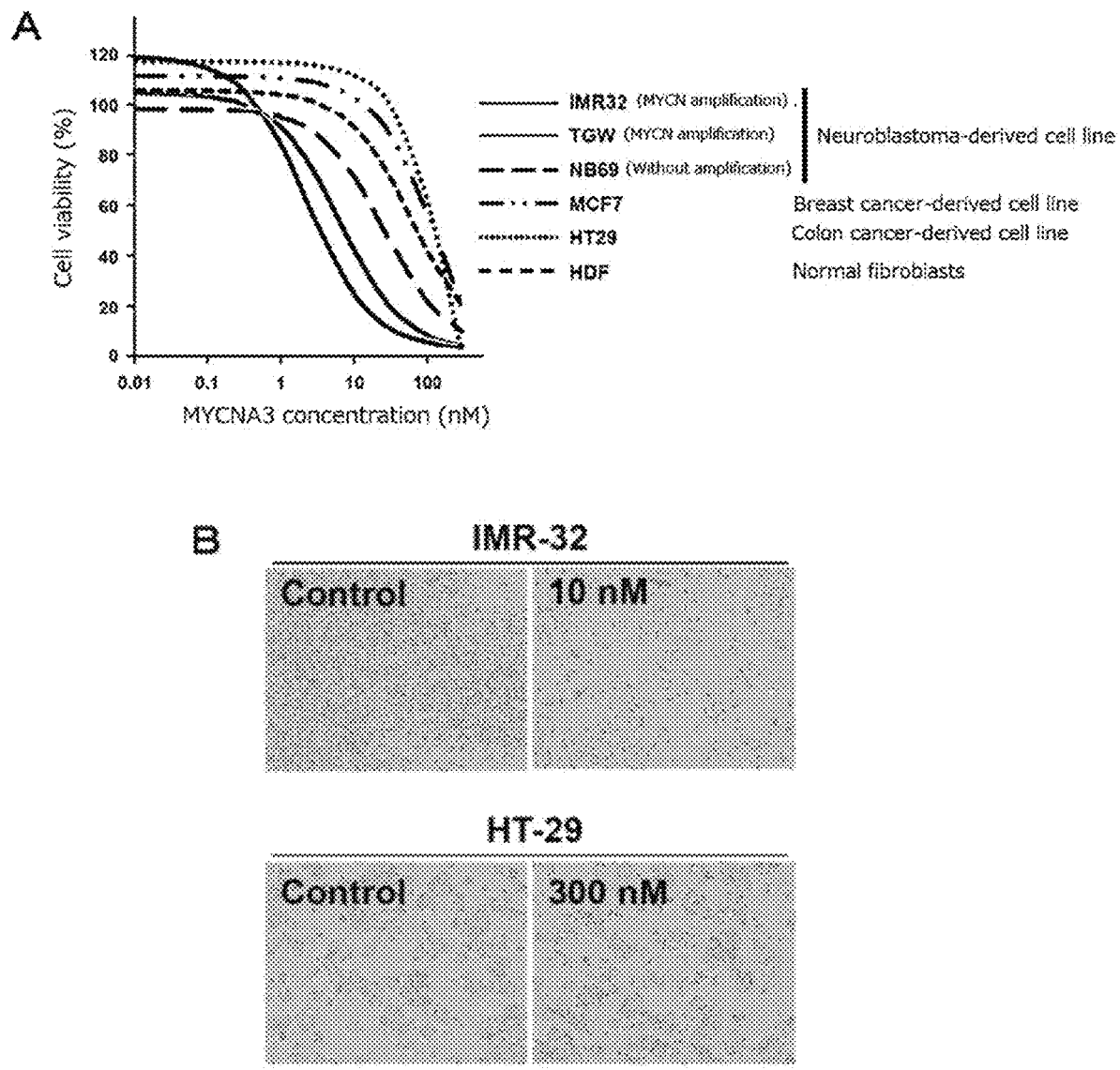
FIG. 34 is a view showing a cytotoxicity test, in which MYCNA3-treated neuroblastoma cells, breast cancer cells, colon cancer cells and normal fibroblasts have been used, and the measurement results of the 50% inhibitory concentration (IC50).

FIG. 34 shows the results obtained by measuring the 50% inhibitory concentration (IC50) of MYCNA3 to IMR-32 cells (with MYCN amplification, neuroblastoma cells), TGW cells (with MYCN amplification, neuroblastoma cells), NB69 cells (without MYCN amplification, neuroblastoma cells), MCF7 cells (breast cancer cells), HT29 cells (colon cancer cells) and HDF cells (corneal epithelial skin fibroblasts), and also, the results obtained by observing the cell growth under an Incucyte culture time-lapse microscope (Essen Instruments, Ann Arbor, Mich.) (at 72 hours after the cells had been treated with MYCNA3). Table 6 shows the results of a cell growth measurement test performed under conditions of 0.3 to 300 nM and a treatment for 72 hours. As a result, the IC50 of MYCNA3 to the IMR-32 cells was 1.1 nM, it was 3.7 nM to the TGW cells, it was 77.0 nM to the MB69 cells, it was 152.2 nM to the MCF7 cells, it was 239.6 nM to the HT29 cells, and it was 56.6 nM to the HDF cells. Thus, the results demonstrate that MYCNA3 suppressed the growth of neuroblastoma cells, and in particular, the growth of neuroblastoma cells attended with MYCN amplification. From these results, it was found that MYCNA3 has a particularly high effect of suppressing the cell growth of neuroblastoma cells attended with MYCN amplification, and that it has a low effect of suppressing cell growth on other types of cancer cells, neuroblastoma cells that are not attended with MYCN amplification, and cell lines derived from normal tissues (FIG. 34 and Table 6).

TABLE 6

| Cell | IC$_{50}$ (nM) |
|---|---|
| IMR32 | 1.1 |
| TGW | 3.7 |
| NB69 | 77.0 |
| MCF7 | 152.2 |
| HT29 | 239.6 |
| HDF | 56.6 |

SEQUENCE LISTING FREE TEXT

SEQ ID NO: 1: Synthetic DNA,
SEQ ID NO: 2: Synthetic DNA,
SEQ ID NO: 3: Synthetic DNA,
SEQ ID NO: 4: Synthetic DNA,
SEQ ID NO: 5: Synthetic DNA,
SEQ ID NO: 6: Synthetic DNA,
SEQ ID NO: 7: Synthetic DNA,
SEQ ID NO: 8: Synthetic DNA,
SEQ ID NO: 9: Synthetic DNA,
SEQ ID NO: 10: Synthetic DNA,
SEQ ID NO: 11: Synthetic DNA,
SEQ ID NO: 12: Synthetic DNA,
SEQ ID NO: 13: Synthetic DNA,
SEQ ID NO: 14: Synthetic DNA,
SEQ ID NO: 15: Synthetic DNA,
SEQ ID NO: 16: Synthetic DNA, and
SEQ ID NO: 17: Synthetic DNA.

The invention claimed is:

1. A complex of an alkylating agent conjugated with DNA-binding compound specifically binding to the genetic mutation site of a driver oncogene, wherein the driver oncogene is at least one selected from among KRAS, HRAS, NRAS, BCR-ABL, EGFR, c-KIT, BRAF, PI3K, ALK, PIK3CA, FLT3, MET, BCL2, EML4-ALK, APC, BRCA1/2, TP53, MSH2, MLH1, MSH6, PMS2, RBI, PTEN, VHL, P16, MEN1, RET, CDH1, STK11, PTCH, Her2/neu, EGFR, MYC, MYCN and MET, and also among genes registered in the database of cancer gene mutation;

and the complex is represented by the following formula:

[Formula 28]

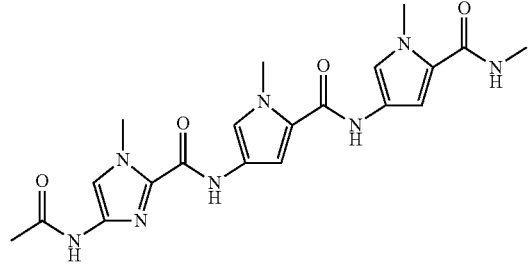

-continued

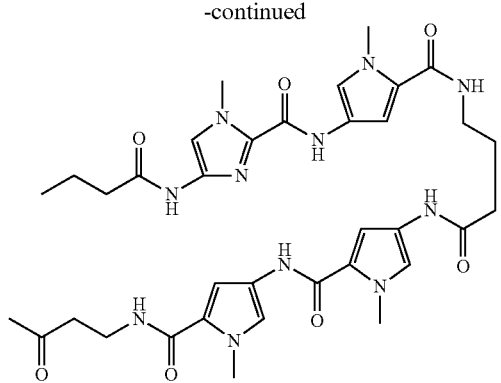

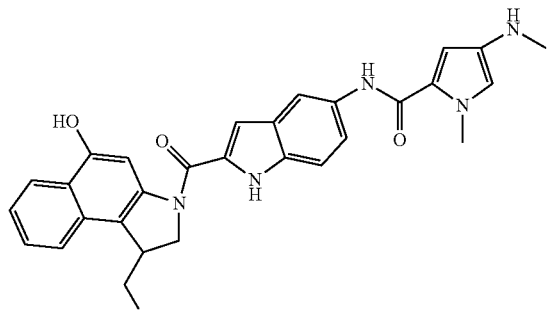

MYCNA1 or is represented by the following formula:

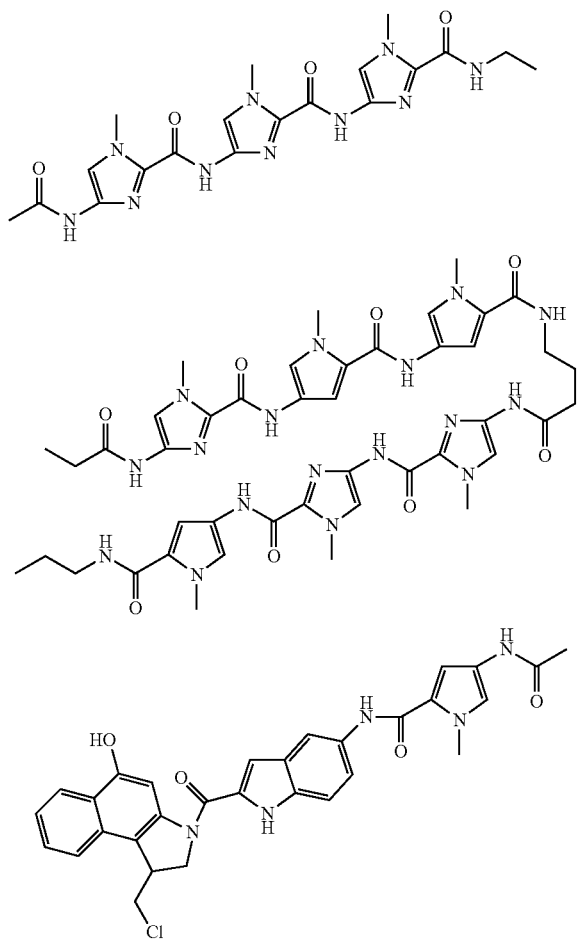

[Formula 29]

MYCNA3

2. The complex according to claim 1, wherein the genetic mutation site is a change in the gene sequence and/or a change in the gene copy number.

3. The complex according to claim 1, wherein the DNA-binding compound is any one of bridged nucleic acid, locked nucleic acid (LNA), PNA, pyrrole-imidazole polyamide (PIP), a pyrrole-imidazole polyamide (PIP) modified product, a DNA-binding protein, and a DNA-binding protein complex.

4. The complex according to claim 1, wherein the alkylating agent is a compound having a functional group with an alkylation ability on a specific nucleotide(s) of DNA.

5. The complex according to claim 4, wherein the alkylating agent is secoCBI.

6. A driver oncogene mutation-specific alkylating agent comprising the complex according to claim 1.

7. A MYCN gene amplification mutation-alkylating agent comprising the complex according to claim 1.

8. A pharmaceutical composition comprising the complex according to claim 1.

9. The pharmaceutical composition according to claim 8, which is an anticancer agent.

10. A kit comprising the complex according to claim 1.

11. A research reagent kit comprising the complex according to claim 1.

12. A therapeutic kit comprising the complex according to claim 1.

13. A method for producing a complex according to claim 1 that specifically alkylates the genetic mutation site of a driver oncogene, which comprises:
(1) designing a DNA-binding compound, such that it can specifically bind to the genetic mutation site of a driver oncogene; and
(2) binding the designed DNA-binding compound to an alkylating agent.

14. The method according to claim 13, wherein the genetic mutation site is a change in the gene sequence or a change in the gene copy number.

15. The method according to claim 13, wherein the DNA-binding compound is any one of bridged nucleic acid, locked nucleic acid (LNA), PNA, pyrrole-imidazole polyamide (PIP), a pyrrole-imidazole polyamide (PIP) modified product, a DNA-binding protein, and a DNA-binding protein complex.

16. The method according to claim 13, wherein the alkylating agent is a compound having a functional group with an alkylation ability on a specific nucleotide sequence of DNA.

17. The method according to claim 16, wherein the alkylating agent is secoCBI.

* * * * *